US007259166B2

(12) United States Patent
Corbett et al.

(10) Patent No.: US 7,259,166 B2
(45) Date of Patent: Aug. 21, 2007

(54) SUBSTITUTED-CYCLOALKYL AND OXYGENATED-CYCLOALKYL GLUCOKINASE ACTIVATORS

(75) Inventors: Wendy Lea Corbett, Randolph, NJ (US); Joseph Samuel Grimsby, Morganville, NJ (US); Nancy-Ellen Haynes, Cranford, NJ (US); Robert Francis Kester, West Orange, NJ (US); Paige Erin Mahaney, Pottstown, PA (US); Jagdish Kumar Racha, Iselin, NJ (US); Ramakanth Sarabu, Towaco, NJ (US); Ka Wang, Wayne, NJ (US)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 11/402,167

(22) Filed: Apr. 10, 2006

(65) Prior Publication Data

US 2006/0178429 A1    Aug. 10, 2006

Related U.S. Application Data

(62) Division of application No. 10/421,109, filed on Apr. 23, 2003, now Pat. No. 7,105,671.

(60) Provisional application No. 60/376,161, filed on Apr. 26, 2002.

(51) Int. Cl.
*C07D 241/20* (2006.01)
*C07D 213/75* (2006.01)
*C07D 277/46* (2006.01)
*C07D 409/12* (2006.01)

(52) U.S. Cl. ............... 514/255.05; 514/336; 514/371; 514/459; 514/460; 514/471; 544/336; 546/282.1; 548/195; 549/419; 549/493; 549/494; 549/495; 549/496

(58) Field of Classification Search ............... 549/419, 549/493, 494, 495, 496; 548/195; 546/282.1; 544/336; 514/255.05, 336, 371, 459, 460, 514/471
See application file for complete search history.

(56) References Cited

U.S. PATENT DOCUMENTS 3,431,301 A    3/1969  Focella et al.
3,776,917 A   12/1973  Mann et al.
5,113,013 A    5/1992  Powell et al.
5,169,951 A   12/1992  Sutter et al.
5,556,859 A    9/1996  Johnson

FOREIGN PATENT DOCUMENTS

| DE | 249 241 | 7/1912 |
| EP | 0566138 | 10/1993 |
| ES | 1436502 | 5/1976 |
| WO | WO 00/26202 | 5/2000 |
| WO | WO 00 58293 | 10/2000 |
| WO | WO 02 08209 | 1/2002 |

OTHER PUBLICATIONS

Colowick, S.P., The Enzymes, vol. 9 (P. Boyer, ed.) Academic Press, New York, NY, p. 1-48 (1973).
Chipkin, et. al., in Joslin's Diabetes (C.R. Kahn and G.C. Wier, eds.), Lea and Febiger, Philadelphia, PA, p. 97-115 (1994).
Printz, et. al., Ann. Rev. Nutrition, vol. 13 (R.E. Olson, D.M. Bier, and D.B. McCormick, eds.) Annual Review Inc, Palo Alto, CA pp. 463-496 (1993).
Meglasson, et al., Amer. J. Physiol., 246, E1-E13 (1984).
Grupe, et al., Cell 83, 69-78, (1995).
Ferre, et al., FASEB J., 10, 1213-1218 (1996).
Liang, et al., Biochem. J. 309, 167-173 (1995).
Glaser, et al. New England J. Med. 338, 226-230 (1998).
Rodier, et. al., Acta Crystallogr., C46 (1990) pp. 154-156.
Robert, J. M. H., et. al., Eur J. Med. Chem. vol. 29, (1994), pp. 841-854.
Spickett, et. al., Eur. J. Med. Chem.-Chimica Therapeutica, vol. 11(1), (1976), pp. 7-12.
Bhat, A. R., et. al., J. Inst. Chemists (India), vol. 61, 1989, pp. 134-136.
Spielman, M.A., et. al., J. Am. Chem. Soc., 70 (1948), pp. 4189-4191.

*Primary Examiner*—Deepak Rao
(74) *Attorney, Agent, or Firm*—George W. Johnston; Dennis P. Tramaloni; Samuel H. Megerditchian

(57) ABSTRACT

2,3-Di-substituted N-heteroaromatic propionamides with said substitution at the 2-position being a substituted phenyl group and at the 3-position being a polar ring, said propionamides being glucokinase activators which increase insulin secretion in the treatment of type II diabetes.

48 Claims, No Drawings

SUBSTITUTED-CYCLOALKYL AND OXYGENATED-CYCLOALKYL GLUCOKINASE ACTIVATORS

CONTINUITY INFORMATION

This application is a division of U.S. application Ser. No. 10/421,109, filed Apr. 23, 2003, now U.S. Pat. No. 7,105,671; which claims the benefit of U.S. Provisional Application Ser. No. 60/376,161, filed Apr. 26, 2002. The entire contents of the above-identified applications are hereby incorporated by reference.

BACKGROUND OF THE INVENTION

Glucokinase (GK) is one of four hexokinases that are found in mammals [Colowick, S. P., in *The Enzymes*, Vol. 9 (P. Boyer, ed.) Academic Press, New York, N.Y., pages 1-48, 1973]. The hexokinases catalyze the first step in the metabolism of glucose, i.e., the conversion of glucose to glucose-6-phosphate. Glucokinase has a limited cellular distribution, being found principally in pancreatic β-cells and liver parenchymal cells. In addition, GK is a rate-controlling enzyme for glucose metabolism in these two cell types that are known to play critical roles in whole-body glucose homeostasis [Chipkin, S. R., Kelly, K. L., and Ruderman, N. B. in *Joslin's Diabetes* (C. R. Khan and G. C. Wier, eds.), Lea and Febiger, Philadelphia, Pa., pages 97-115, 1994]. The concentration of glucose at which GK demonstrates half-maximal activity is approximately 8 mM. The other three hexokinases are saturated with glucose at much lower concentrations (<1 mM). Therefore, the flux of glucose through the GK pathway rises as the concentration of glucose in the blood increases from fasting (5 mM) to postprandial (≈10-15 mM) levels following a carbohydrate-containing meal [Printz, R. G., Magnuson, M. A., and Granner, D. K. in *Ann. Rev. Nutrition* Vol. 13 (R. E. Olson, D. M. Bier, and D. B. McCormick, eds.), Annual Review, Inc., Palo Alto, Calif., pages 463-496, 1993]. These findings contributed over a decade ago to the hypothesis that GK functions as a glucose sensor in β-cells and hepatocytes (Meglasson, M. D. and Matschinsky, F. M. *Amer. J. Physiol.* 246, E1-E13, 1984). In recent years, studies in transgenic animals have confirmed that GK does indeed play a critical role in whole-body glucose homeostasis. Animals that do not express GK die within days of birth with severe diabetes while animals overexpressing GK have improved glucose tolerance (Grupe, A., Hultgren, B., Ryan, A. et al., *Cell* 83, 69-78, 1995; Ferrie, T., Riu, E., Bosch, F. et al., *FASEB J.*, 10, 1213-1218, 1996). An increase in glucose exposure is coupled through GK in β-cells to increased insulin secretion and in hepatocytes to increased glycogen deposition and perhaps decreased glucose production.

The finding that type II maturity-onset diabetes of the young (MODY-2) is caused by loss of function mutations in the GK gene suggests that GK also functions as a glucose sensor in humans (Liang, Y., Kesavan, P., Wang, L. et al., *Biochem. J.* 309, 167-173, 1995). Additional evidence supporting an important role for GK in the regulation of glucose metabolism in humans was provided by the identification of patients that express a mutant form of GK with increased enzymatic activity. These patients exhibit a fasting hypoglycemia associated with an inappropriately elevated level of plasma insulin (Glaser, B., Kesavan, P., Heyman, M. et al., *New England J. Med.* 338, 226-230, 1998). While mutations of the GK gene are not found in the majority of patients with type II diabetes, compounds that activate GK, and thereby increase the sensitivity of the GK sensor system, will still be useful in the treatment of the hyperglycemia characteristic of all type II diabetes. Glucokinase activators will increase the flux of glucose metabolism in β-cells and hepatocytes, which will be coupled to increased insulin secretion. Such agents would be useful for treating type II diabetes.

SUMMARY OF THE INVENTION

This invention provides a compound, comprising an amide of the formula:

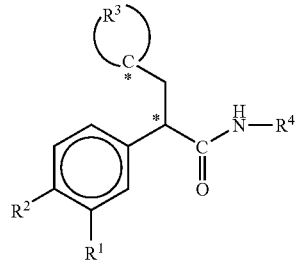

I wherein $R^1$ and $R^2$ are independently hydrogen, halo, amino, hydroxyamino, cyano, nitro, lower alkyl, —$OR^5$,

perfluoro-lower alkyl, lower alkyl thio, perfluoro-lower alkyl thio, lower alkyl sulfonyl, perfluoro-lower alkyl sulfonyl, lower alkyl sulfinyl, or sulfonamido;

$R^3$ is an unbranched alkyl chain of 4-5 carbon atoms or an unbranched heteroalkyl chain of 3-4 carbon atoms plus one oxygen or sulfur atom wherein the chain, in combination with the carbon atom it is bonded to, forms a five- or six-membered ring, and when the chain contains no heteroatoms, one carbon member of the chain is substituted with one moiety selected from the group consisting of hydroxy, oxo, hydroxyimino, methoxyimino, halo, methoxy, and acetoxy or one carbon member of the chain is disubstituted with one hydroxy and one lower alkyl or is disubstituted with halogen when the chain contains an O heteroatom, the chain is unsubstituted, and when the chain contains an S heteroatom, the chain is unsubstituted or the S heteroatom member of the chain is substituted by an oxo group;

$R^4$ is

an unsubstituted or mono-substituted five- or six-membered heteroaromatic ring connected by a ring carbon atom to the amine group shown, which five- or six-membered heteroaromatic ring contains from 1 to 3 heteroatoms selected from sulfur, oxygen or nitrogen, with one heteroatom being nitrogen which is adjacent to the connecting ring carbon atom; said mono-substituted heteroaromatic ring being mono-substituted at a position on a ring carbon atom other than adjacent to said connecting carbon atom with a substituent selected from the group consisting of lower alkyl, halo, nitro, cyano, perfluoro-lower alkyl, amidooxime, or

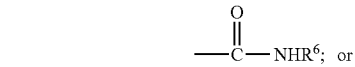
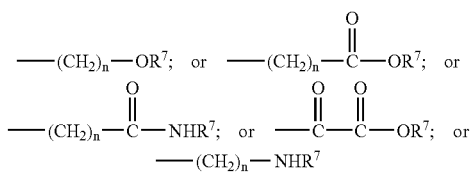

n is 0, 1, 2, 3 or 4;
$R^5$ is hydrogen, lower alkyl, or perfluoro-lower alkyl; $R^6$ is lower alkyl; and $R^7$ is hydrogen or lower alkyl;
* denotes an asymmetric carbon atom;

or a pharmaceutically acceptable salt thereof.

The compounds of formula I have been found to activate glucokinase in vitro. Glucokinase activators are useful for increasing insulin secretion in the treatment of type II diabetes.

DETAILED DESCRIPTION OF THE INVENTION

This invention provides a compound, comprising an amide of the formula:

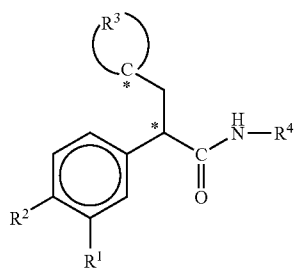

I wherein $R^1$ and $R^2$ are independently hydrogen, halo, amino, hydroxyamino, cyano, nitro, lower alkyl, —$OR^5$,

perfluoro-lower alkyl, lower alkyl thio, perfluoro-lower alkyl thio, lower alkyl sulfonyl, perfluoro-lower alkyl sulfonyl, lower alkyl sulfinyl, or sulfonamido; $R^3$ is an unbranched alkyl chain of 4-5 carbon atoms or an unbranched heteroalkyl chain of 3-4 carbon atoms plus one oxygen or sulfur atom, wherein the chain, in combination with the carbon atom it is bonded to, forms a five- or six-membered ring, and when the chain contains no heteroatoms, one carbon member of the chain is substituted with one moiety selected from the group consisting of hydroxy, oxo, hydroxyimino, methoxyimino, halo, methoxy, and acetoxy, or one carbon member of the chain is disubstituted with one hydroxy and one lower alkyl or is disubstituted with halogen when the chain contains an O heteroatom, the chain is unsubstituted, and when the chain contains an S heteroatom, the chain is unsubstituted or the S heteroatom member of the chain is substituted by an oxo group;

$R^4$ is

an unsubstituted or mono-substituted five- or six-membered heteroaromatic ring connected by a ring carbon atom to the amine group shown, which five- or six-membered heteroaromatic ring contains from 1 to 3 heteroatoms selected from sulfur, oxygen or nitrogen, with one heteroatom being nitrogen which is adjacent to the connecting ring carbon atom; said mono-substituted heteroaromatic ring being mono-substituted at a position on a ring carbon atom other than adjacent to said connecting carbon atom with a substituent selected from the group consisting of lower alkyl, halo, nitro, cyano, perfluoro-lower alkyl, amidooxime, or

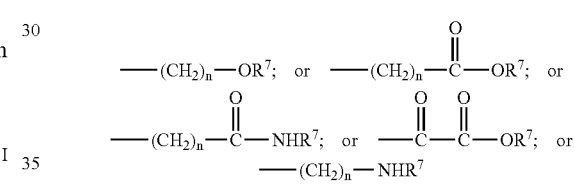

n is 0, 1, 2, 3 or 4;
$R^5$ is hydrogen, lower alkyl, or perfluoro-lower alkyl; $R^6$ is lower alkyl; and $R^7$ is hydrogen or lower alkyl;
* denotes a carbon atom that is asymmetric in all or most of the compounds of formula I;

or a pharmaceutically acceptable salt thereof.

In the compound of formula I, the "*" illustrates carbon atoms that are asymmetric in most or all of the species of formula I. The compound of formula I may be present either as a racemate or in isolated "R" or "S" configurations at the asymmetric carbons shown. The "R" enantiomers are preferred.

As used throughout this application, the term "lower alkyl" includes both straight chain and branched chain alkyl groups having from 1 to 7 carbon atoms, such as methyl, ethyl, propyl, isopropyl, preferably methyl and ethyl. As used herein, the term "halogen or halo" unless otherwise stated, designates all four halogens, i.e. fluorine, chlorine, bromine, and iodine. As used herein, "perfluoro-lower alkyl" means any lower alkyl group wherein all of the hydrogens of the lower alkyl group are substituted or replaced by fluoro. Among the preferred perfluoro-lower alkyl groups are trifluoromethyl, pentafluoroethyl, heptafluoropropyl, etc.

As used herein, the term "aryl" signifies aryl mononuclear aromatic hydrocarbon groups such as phenyl, tolyl, etc. which can be unsubstituted or substituted in one or more positions with halogen, nitro, lower alkyl, or lower alkoxy substituents and polynuclear aryl groups, such as naphthyl, anthryl, and phenanthryl, which can be unsubstituted or substituted with one or more of the aforementioned groups. Preferred aryl groups are the substituted and unsubstituted mononuclear aryl groups, particularly phenyl. As used herein, the term "lower alkoxy" includes both straight chain and branched chain alkoxy groups having from 1 to 7 carbon atoms, such as methoxy, ethoxy, propoxy, isopropoxy, preferably methoxy and ethoxy. The term "arylalkyl" denotes an alkyl group, preferably lower alkyl, in which one of the hydrogen atoms can be replaced by an aryl group. Examples of arylalkyl groups are benzyl, 2-phenylethyl, 3-phenylpropyl, 4-chlorobenzyl, 4-methoxybenzyl and the like.

As used herein, the term "lower alkanoic acid" denotes lower alkanoic acids containing from 2 to 7 carbon atoms such as propionic acid, acetic acid and the like. The term "lower alkanoyl" denotes monovalent alkanoyl groups having from 2 to 7 carbon atoms such as propionoyl, acetyl and the like. The term "aroic acids" denotes aryl alkanoic acids where aryl is as defined above and alkanoic contains from 1 to 6 carbon atoms. The term "aroyl" denotes aroic acids wherein aryl is as defined hereinbefore, with the hydrogen group of the COOH moiety removed. Among the preferred aroyl groups is benzoyl.

During the course of synthetic reactions, the various functional groups such as the free carboxylic acid or hydroxy groups may be protected via conventional hydrolyzable ester or ether protecting groups. As used herein, the term "hydrolyzable ester or ether protecting groups" designates any ester or ether conventionally used for protecting carboxylic acids or alcohols which can be hydrolyzed to yield the respective carboxy or hydroxy group. Exemplary ester groups useful for those purposes are those in which the acyl moieties are derived from a lower alkanoic, aryl lower alkanoic, or lower alkane dicarboxylic acid. Among the activated acids which can be utilized to form such groups are acid anhydrides, acid halides, preferably acid chlorides or acid bromides derived from aryl or lower alkanoic acids. Example of anhydrides are anhydrides derived from monocarboxylic acids such as acetic anhydride, benzoic acid anhydride, and lower alkane dicarboxylic acid anhydrides, e.g. succinic anhydride as well as chloro formates e.g. trichloromethyl chloroformate and ethyl chloroformate being preferred. A suitable ether protecting group for alcohols are, for example, the tetrahydropyranyl ethers such as 4-methoxy-5,6-dihydroxy-2H-pyranyl ethers. Others are aroylmethylethers such as benzyl, benzhydryl or trityl ethers or a-lower alkoxy lower alkyl ethers, for example, methoxymethyl or allylic ethers or alkyl silylethers such as trimethylsilylether.

The term "amino protecting group" designates any conventional amino protecting group which can be cleaved to yield the free amino group. The preferred protecting groups are the conventional amino protecting groups utilized in peptide synthesis. Especially preferred are those amino protecting groups which are cleavable under mildly acidic conditions from about pH 2 to 3. Particularly preferred amino protecting groups include t-butyl carbamate (BOC), benzyl carbamate (CBZ), and 9-flurorenylmethyl carbamate (FMOC).

The heteroaromatic ring defined by $R^4$ can be an unsubstituted or mono-substituted five- or six-membered heteroaromatic ring having from 1 to 3 heteroatoms selected from the group consisting of oxygen, nitrogen, or sulfur and connected by a ring carbon to the amine of the amide group shown. The heteroaromatic ring contains a first nitrogen heteroatom adjacent to the connecting ring carbon atom, and if present, the other heteroatoms can be sulfur, oxygen, or nitrogen. Such heteroaromatic rings include, for example, pyridazinyl, isoxazolyl, isothiazolyl, and pyrazolyl. Among the preferred heteroaromatic rings are pyridinyl, pyrazinyl, pyrimidinyl, thiazolyl, oxazolyl, and imidazolyl. These heteroaromatic rings which constitute $R^4$ are connected via a ring carbon atom to the amide group to form the amides of formula I. The ring carbon atom of the heteroaromatic ring which is connected via the amide linkage to form the compound of formula I cannot contain any substituent.

When $R^4$ is an unsubstituted or mono-substituted five-membered heteroaromatic ring, the preferred rings are those which contain a nitrogen heteroatom adjacent to the connecting ring carbon and a second heteroatom adjacent to the connecting ring carbon or adjacent to said first heteroatom. The preferred five-membered heteroaromatic rings contain 2 or 3 heteroatoms with thiazolyl, imidazolyl, oxazolyl, and thiadiazolyl being especially preferred. When the heteroaromatic ring is a six-membered heteroaromatic, the ring is connected by a ring carbon to the amine group shown, with one nitrogen heteroatom being adjacent to the connecting ring carbon atom. The preferred six-membered heteroaromatic rings include, for example, pyridinyl, pyrimidinyl, pyrazinyl, pyridazinyl, and triazinyl.

The term "pharmaceutically acceptable salts" as used herein include any salt with both inorganic or organic pharmaceutically acceptable acids such as hydrochloric acid, hydrobromic acid, nitric acid, sulfuric acid, phosphoric acid, citric acid, formic acid, maleic acid, acetic acid, succinic acid, tartaric acid, methanesulfonic acid, paratoluene sulfonic acid and the like. The term "pharmaceutically acceptable salts" also includes any pharmaceutically acceptable base salt such as amine salts, trialkyl amine salts and the like. Such salts can be formed quite readily by those skilled in the art using standard techniques.

The five- or six-membered ring formed by the combination of $R^3$ and the carbon atom $R^3$ is attached to, hereinafter referred to as —CH<$R^3$, is a polar group. The five- or six-membered ring may consist of all carbon atoms or contain one heteroatom selected from oxygen or sulfur. If the five- or six-membered ring contains a heteroatom, all of the carbon atoms in the ring will be saturated with hydrogen atoms. If the heteroatom is S, then the S atom is optionally substituted with an oxo group. If the five- or six-membered ring contains no heteroatoms, then one carbon atom in the $R^3$ chain is substituted with one moiety selected from hydroxy, oxo, hydroxyimino, methoxyimino, halogen, methoxy, and acetoxy, or one carbon atom of the chain is disubstituted with one hydroxy and one lower alkyl or is disubstituted with halogen. Such five- or six-membered rings include tetrahydro-furans, tetrahydro-pyrans, tetrahydro-thiopyrans, 1-oxo-tetrahydro-1-thiopyrans, keto-cycloalkyls, hydroxy-cycloalkyls, methoxy-cycloalkyls, hydroxyimino-cycloalkyls, methoxyimino-cycloalkyls, halo-cycloalkyls, and dihalo-cycloalkyls.

In accordance with one embodiment of the invention, called compound I-A,
$R^1$ is hydrogen, halo, or perfluoro-lower alkyl;
$R^2$ is halo or lower alkyl sulfonyl;
$R^3$ is as defined above;
$R^4$ is an unsubstituted or mono-substituted five- or six-membered heteroaromatic ring connected by a ring carbon atom to the amine group shown, which five- or six-membered heteroaromatic ring contains from 1 or 2 heteroatoms selected from sulfur or nitrogen, with one heteroatom being nitrogen which is adjacent to the connecting ring carbon atom; said mono-substituted heteroaromatic ring being mono-substituted at a position on a ring carbon atom other than adjacent to said connecting carbon atom with a substituent selected from the group consisting of lower alkyl, lower alkoxy, halo, nitro, cyano, perfluoro-lower alkyl, amidooxime, or

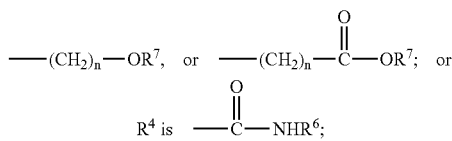

n is 0, 1, 2, 3 or 4; and
$R^6$ is lower alkyl; and $R^7$ is hydrogen or lower alkyl;
or a pharmaceutically acceptable salt thereof.

In other preferred embodiments of compound I-A, $R^4$ is —CO—NH—$R^6$ and $R^3$ is one of: a) a chain of 3 carbon atoms and one oxygen atom, b) a chain of 3 carbon atoms and one sulfur atom, c) a chain of 4 carbon atoms, d) a chain of 4 carbon atoms and one oxygen atom, e) a chain of 4 carbon atoms and one sulfur atom, or f) a chain of 5 carbon atoms. The group —CH<$R^3$ is optionally substituted as defined above.

In still other preferred embodiments of compound I-A, $R^4$ is an unsubstituted thiazoyl and $R^3$ is one of: a) a chain of 3 carbon atoms and one oxygen atom, b) a chain of 3 carbon atoms and one sulfur atom, c) a chain of 4 carbon atoms, d) a chain of 4 carbon atoms and one oxygen atom, e) a chain of 4 carbon atoms and one sulfur atom, or f) a chain of 5 carbon atoms. The group —CH<$R^3$ is optionally substituted as defined above.

In a further preferred embodiments of compound I-A, $R^4$ is an unsubstituted or mono-substituted pyrazinyl and $R^3$ is one of: a) a chain of 3 carbon atoms and one oxygen atom, b) a chain of 3 carbon atoms and one sulfur atom, c) a chain of 4 carbon atoms, d) a chain of 4 carbon atoms and one oxygen atom, e) a chain of 4 carbon atoms and one sulfur atom, or f) a chain of 5 carbon atoms. The group —CH<$R^3$ is optionally substituted as defined above.

In yet further preferred embodiments of compound I-A, $R^4$ is a substituted pyridinyl and $R^3$ is one of: a) a chain of 3 carbon atoms and one oxygen atom, b) a chain of 3 carbon atoms and one sulfur atom, c) a chain of 4 carbon atoms, d) a chain of 4 carbon atoms and one oxygen atom, e) a chain of 4 carbon atoms and one sulfur atom, or f) a chain of 5 carbon atoms. The group —CH<$R^3$ is optionally substituted as defined above.

The compound of formula I can be prepared starting from the compound of formula V by the following Reaction Scheme:

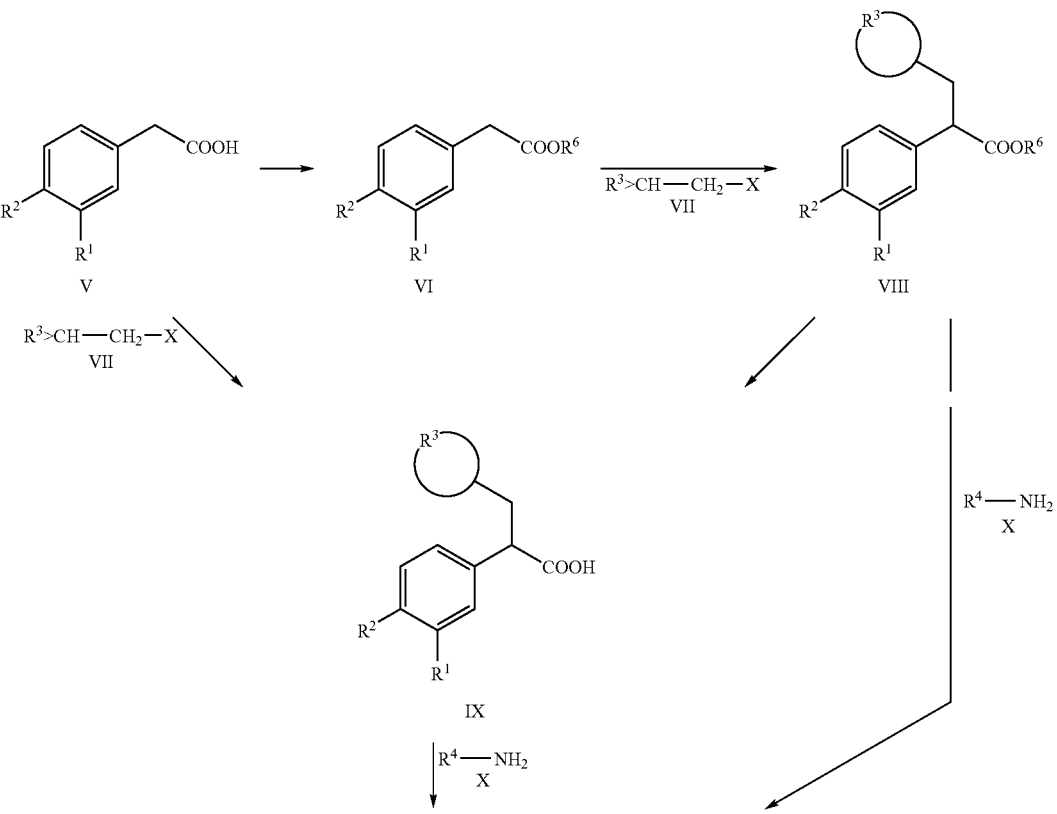

Reaction Scheme

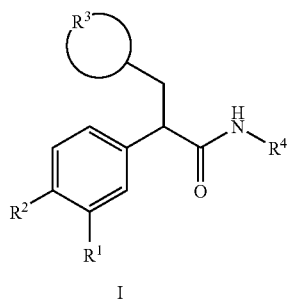

I wherein $R^1$, $R^2$, $R^3$, $R^4$, and $R^6$ are as above.

The carboxylic acids or their lower alkyl esters of formula V and VI wherein one of $R^1$ and $R^2$ is hydrogen, nitro, mercapto, methylthio, trifluoromethylthio, methylsulfonyl, amino, fluoro, chloro, bromo, iodo, hydroxy, methoxy, trifluoromethoxy, methyl, trifluoromethyl, and carboxy, and the other is hydrogen are commercially available. In cases where only the carboxylic acids are available, and if necessary for further chemical modification to produce the desired substitutions at $R^1$ and $R^2$, the carboxylic acids can be converted to the corresponding esters of lower alkyl alcohols using any conventional esterification methods.

All the reactions hereto forward are to be carried out on the lower alkyl esters of the carboxylic acids of formula VI or VIII or may be carried out on the carboxylic acids of formula V or IX themselves.

The compounds of formula V where one of $R^1$ and $R^2$ is amino can be converted to other substituents either before or after conversion to the compounds of formula I. In this respect, the amino groups can be diazotized to yield the corresponding diazonium compound, which in situ can be reacted with the desired lower alkyl thiol or perfluoro-lower alkyl thiol (see for example, Baleja, J. D. *Synth. Comm.* 1984, 14, 215; Giam, C. S.; Kikukawa, K., *J. Chem. Soc, Chem. Comm.* 1980, 756; Kau, D.; Krushniski, J. H.; Robertson, D. W, *J. Labelled Compd Rad.* 1985, 22, 1045; Oade, S.; Shinhama, K.; Kim, Y. H., *Bull Chem Soc. Jpn.* 1980, 53, 2023; Baker, B. R.; et al, *J. Org. Chem.* 1952, 17, 164) to yield corresponding compounds of formula V where one of the substituents is lower alkyl thio or perfluoro-lower alkyl thio and the other is hydrogen. If desired, the lower alkyl thio or perfluoro-lower alkyl thio compounds can then be converted to the corresponding lower alkyl sulfonyl or perfluoro-lower alkyl sulfonyl substituted compounds of formula V by oxidation. Any conventional method of oxidizing alkyl thio substituents to sulfones can be utilized to effect this conversion. On the other hand, the lower alkyl thio compounds can also be converted to the corresponding lower alkyl sulfinyl compounds of formula V by oxidation. Any conventional method of oxidizing alkyl thio substituents to sulfoxides can be utilized to effect this conversion.

If it is desired to produce compounds of formula V where one of $R^1$ and $R^2$ is hydrogen and the other is sulfonamido, the mercapto substituent can be oxidized to a —$SO_3H$ group which then can be converted to —$SO_2Cl$, which, in turn, is then reacted with ammonia to form the sulfonamide substituent, —$SO_2$—$NH_2$.

If it is desired to produce compounds with lower alkyl or perfluoro-lower alkyl groups of compounds of formula V, the corresponding halo substituted compounds of formula V can be used as starting materials. Any conventional method of converting an aromatic halo group to the corresponding alkyl group (see for example, Katayama, T.; Umeno, M., *Chem. Lett.* 1991, 2073; Reddy, G. S.; Tam., *Organometallics*, 1984, 3, 630; Novak, J.; Salemink, C. A., *Synthesis*, 1983, 7, 597; Eapen, K. C.; Dua, S. S.; Tamboroski, C., *J. Org. Chem.* 1984, 49, 478; Chen, Q, -Y.; Duan, J. -X. *J. Chem. Soc. Chem. Comm.* 1993, 1389; Clark, J. H.; McClinton, M. A.; Jone, C. W.; Landon, P.; Bisohp, D.; Blade, R. J., *Tetrahedron Lett.* 1989, 2133; Powell, R. L.; Heaton, C. A, U.S. Pat. No. 5,113,013) can be utilized to effect this conversion.

For compounds of formula V wherein one or both of $R^1$ and $R^2$ is hydroxyamino, the corresponding nitro compounds can be used as starting material and can be converted to the corresponding compounds where $R^1$ and/or $R^2$ are hydroxyamino. Any conventional method of converting a nitro group to the corresponding aromatic hydroxyamino compound can be used to affect this conversion.

The carboxylic acids or esters of formula V or VI wherein both of $R^1$ and $R^2$ are chloro, fluoro, hydroxy, and methoxy are commercially available. The carboxylic acid of formula V wherein $R^1$ is trifluoromethyl and $R^2$ is fluoro, and the carboxylic acid of formula V wherein $R^1$ is nitro and $R^2$ is chloro are also commercially available. In cases, where only the carboxylic acids are available, they can be converted to the corresponding esters of lower alkyl alcohols using any conventional esterification method.

To produce the compound of formula V where both $R^1$ and $R^2$ are nitro, 3,4-dinitrotoluene can be used as starting material. This compound can be converted to the corresponding 3,4-dinitrophenyl acetic acid. Any conventional method of converting an aryl methyl group to the corresponding aryl acetic acid can be utilized to effect this conversion (see for example, Clark, R. D.; Muchowski, J. M.; Fisher, L. E.; Flippin, L. A.; Repke, D. B.; Souchet, M, *Synthesis*, 1991, 871). The compounds of formula V where both $R^1$ and $R^2$ substituents are amino can be obtained from the corresponding dinitro compound of formula V, described above. Any conventional method of reducing a nitro group to an amine can be utilized to effect this conversion.

The compound of formula V where both $R^1$ and $R^2$ are amine groups can be used to prepare the corresponding compound of formula V where both $R^1$ and $R^2$ are iodo or bromo via a diazotization reaction. Any conventional method of converting an amino group to an iodo or bromo group (see for example, Lucas, H. J.; Kennedy, E. R. *Org. Synth. Coll. Vol, II* 1943, 351) can be utilized to effect this conversion.

If it is desired to produce compounds of formula V where both $R^1$ and $R^2$ are lower alkyl thio or perfluoro-lower alkyl thio groups, the compound of formula V where $R^1$ and $R^2$ are amino can be used as starting material. Any conventional method of converting an aryl amino group to an aryl lower alkyl thio or to a perfluoro-lower alkyl thio group can be utilized to effect this conversion. If it is desired to produce compounds of formula V where $R^1$ and $R^2$ are lower alkyl sulfonyl or lower perfluoro alkyl sulfonyl, the corresponding compounds of formula V where $R^1$ and $R^2$ are lower alkyl thio or perfluoro-lower alkyl thio can be used as starting material. Any conventional method of oxidizing alkyl thio substituents to sulfones can be utilized to effect this conversion. On the other hand, if it is desired to produce compounds of formula V where $R^1$ and $R^2$ are lower alkyl sulfinyl, the corresponding compounds of formula V where $R^1$ and $R^2$ are lower alkyl thio can be used as starting material. Any conventional method of oxidizing alkyl thio substituents to sulfoxides can be utilized to effect this conversion.

If it is desired to produce compounds of formula V where both $R^1$ and $R^2$ are substituted with lower alkyl or perfluoro-lower alkyl groups, the corresponding halo substituted compounds of formula V can be used as starting materials. Any conventional method of converting an aromatic halo group to the corresponding lower alkyl or perfluoro-lower alkyl group can be utilized to effect this conversion.

The carboxylic acids corresponding to the compounds of formula V where one of $R^1$ and $R^2$ is nitro and the other is halo are known from the literature (see for 4-chloro-3-nitrophenyl acetic acid: Tadayuki, S.; Hiroki, M.; Shinji, U.; Mitsuhiro, S. Japanese patent, JP 71-99504, *Chemical Abstracts* 80:59716; see for 4-nitro-3-chlorophenyl acetic acid: Zhu, J.; Beugelmans, R.; Bourdet, S.; Chastanet, J.; Rousssi, G. *J. Org. Chem.* 1995, 60, 6389; Beugelmans, R.; Bourdet, S.; Zhu, J. *Tetrahedron Lett.* 1995, 36, 1279). These carboxylic acids can be converted to the corresponding lower alkyl esters using any conventional esterification methods. Thus, if it is desired to produce the compound of formula V where one of $R^1$ and $R^2$ is nitro and the other is lower alkyl thio or perfluoro-lower alkyl thio, the corresponding compound where one of $R^1$ and $R^2$ is nitro and the other is chloro can be used as starting material. In this reaction, any conventional method of nucleophilic displacement of an aromatic chlorine group with a lower alkyl thiol or perfluoro-lower alkyl thio can be used (see for example, Singh, P.; Batra, M. S.; Singh, H, *J. Chem. Res. -S* 1985 (6), S204; Ono, M.; Nakamura, Y.; Sata, S.; Itoh, I, *Chem. Lett,* 1988, 1393; Wohrle, D.; Eskes, M.; Shigehara, K.; Yamada, A, *Synthesis,* 1993, 194; Sutter, M.; Kunz, W, US patent, U.S. Pat. No. 5,169,951). Once the compounds of formula V where one of $R^1$ and $R^2$ is nitro and the other is lower alkyl thio or perfluoro-lower alkyl thio are available, they can be converted to the corresponding compounds of formula V where one of $R^1$ and $R^2$ is nitro and the other is lower alkyl sulfonyl or perfluoro-lower alkyl sulfonyl using conventional oxidation procedures. If it is desired to produce compounds of formula V where one of $R^1$ and $R^2$ is amino and the other is lower alkyl thio or perfluoro-lower alkyl thio, the corresponding compound where one of $R^1$ and $R^2$ is nitro and the other is lower alkyl thio or perfluoro-lower alkyl thio can be used as starting materials. Any conventional method of reducing an aromatic nitro group to an amine can be utilized to effect this conversion. If it is desired to produce compounds of formula V where one of $R^1$ and $R^2$ is lower alkyl thio and the other is perfluoro-lower alkyl thio, the corresponding compound where one of $R^1$ and $R^2$ is amino and the other is lower alkyl thio or perfluoro-lower alkyl thio can be used as starting materials. Any conventional method of diazotizing an aromatic amino group and reacting it in situ with the desired lower alkyl thiol can be utilized to effect this conversion. If it is desired to produce compounds of formula V where one of $R^1$ and $R^2$ is lower alkyl sulfonyl and the other is perfluoro-lower alkyl sulfonyl, the corresponding compounds where one of $R^1$ and $R^2$ is lower alkyl thio and the other is perfluoro-lower alkyl thio can be used as starting materials. Any conventional method of oxidizing an aromatic thio group to the corresponding sulfone group can be utilized to effect this conversion.

If it is desired to produce compounds of formula V where one of $R^1$ and $R^2$ is halo and the other is lower alkyl thio or perfluoro-lower alkyl thio, the corresponding compounds where one of $R^1$ and $R^2$ is amino and the other is lower alkyl thio or perfluoro-lower alkyl thio can be used as starting materials. Any conventional method of diazotizing an aromatic amino group and conversion of it in situ to an aromatic halide can be utilized to effect this conversion. If it is desired to produce compounds of formula V where one of $R^1$ and $R^2$ is halo and the other is lower alkyl sulfonyl or perfluoro-lower alkyl sulfonyl, the corresponding compounds where one of $R^1$ and $R^2$ is halo and the other is lower alkyl thio or perfluoro-lower alkyl thio can be used as starting materials. Any conventional method of oxidizing an aromatic thio group to the corresponding sulfone can be utilized to effect this conversion.

If one wishes to prepare the compound formula V where one of $R^1$ and $R^2$ is nitro and the other is amino, the compound of formula V where one of $R^1$ and $R^2$ is nitro and the other is chloro can be used as a starting material. The chloro substituent on the phenyl ring can be converted to an iodo substituent (see for example, Bunnett, J. F.; Conner, R. M.; *Org. Synth. Coll Vol V,* 1973, 478; Clark, J. H.; Jones, C. W. *J Chem. Soc. Chem. Commun.* 1987, 1409), which in turn can be reacted with an azide transferring agent to form the corresponding azide (see for example, Suzuki, H.; Miyoshi, K.; Shinoda, M. *Bull. Chem. Soc. Jpn,* 1980, 53, 1765). This azide can then be reduced in a conventional manner to form the amine substituent by reducing it with commonly used reducing agents for converting azides to amines (see for example, Soai, K.; Yokoyama, S.; Ookawa, A. *Synthesis,* 1987, 48).

If it is desired to produce the compound of formula V where both $R^1$ and $R^2$ are cyano, this compound can be prepared as described hereinbefore from compounds where $R^1$ and $R^2$ are amino via diazotization to produce the diazonium salt followed by reaction with a cyano group transferring agent. If it is desired to produce compounds of formula V where one of $R^1$ and $R^2$ is cyano and the other is not cyano, the compound of formula V where one of $R^1$ and $R^2$ is nitro and the other is chloro can be used as a starting material. Using this starting material, the nitro is first reduced to the amino derivative. Any conventional method of reducing a nitro group to an amine can be utilized to effect this conversion. The amino group is then converted to the cyano group via diazotization to produce the diazonium salt followed by reaction with a cyano group transferring agent. The halo can then be converted to any other desired $R^1$ and $R^2$ substituent as described hereinbefore.

If it is desired to produce the compound of formula V wherein one of $R^1$ or $R^2$ is a —C(O)—OR$^6$, this compound can be formed from the corresponding compound where one of $R^1$ and $R^2$ is an amino group by converting the amino group to a diazonium salt, reacting the diazonium salt with a hydrohalic acid to form the corresponding halide, forming the Grignard reagent from the corresponding halide, and finally reacting the Grignard reagent with a carboxylate source to produce the corresponding acid which can then be esterified. On the other hand, if one wants to produce the compound of formula V where both $R^1$ and $R^2$ are —C(O)—$OR^6$, this compound can be produced as described above from the corresponding compound of formula V where both $R^1$ and $R^2$ are amino groups. In the same manner, the amino groups in the compound of formula V can be converted to the corresponding compound where either $R^1$ or $R^2$ or both of $R^1$ and $R^2$ is $OR^5$ by simply reacting the amino group with sodium nitrate in sulfuric acid to convert the amino group to a hydroxy group and thereafter etherifying, if desired, the hydroxy group.

If it is desired to produce compounds of formula V where $R^1$ is hydrogen and $R^2$ is lower alkyl sulfonyl, the known 4-mercaptophenylacetic acid may be used as a starting material. The compound of formula V where $R^1$ is hydrogen and $R^2$ is mercapto may be alkylated by conventional methods (for example, with an alkyl halide) to the corresponding lower alkyl thio compounds of formula V. The lower alkyl thio compounds can then be converted to the corresponding lower alkyl sulfonyl compounds of formula V by oxidation. Any conventional method of oxidizing an alkyl thio substituent to the corresponding sulfone group can be utilized to effect this conversion.

On the other hand, if it is desired to produce the compounds of formula V where $R^1$ is trifluoromethyl and $R^2$ is lower alkyl sulfonyl, the known 4-fluoro-3-(trifluoromethyl)phenyl acetic acid can be used as a starting material. In this reaction, any conventional method of nucleophilic displacement of an aromatic fluorine group with a lower alkyl thiol can be utilized to effect this conversion (see for example, Boswell, G. E.; Licause, J. F. *J. Org Chem.* 1995, 6592; Sheikh, Y. M. et al. *J. Org. Chem.* 1982, 4341; Brown, F. C. et al. *J. Org. Chem.* 1961, 4707). Once the compounds of formula V where $R^1$ is trifluoromethyl and $R^2$ is lower alkyl thio are available, they can be converted to the corresponding compounds of formula V where $R^1$ is trifluoromethyl and $R^2$ is lower alkyl sulfonyl using conventional oxidation procedures.

If it is desired to produce compounds of formula V where $R^1$ is halo and $R^2$ is lower alkyl sulfonyl, the known 2-halothiophenols can also be used as starting material. In this reaction sequence, the mercapto group may be alkylated by conventional methods (for example, with a lower alkyl halide) to the corresponding 2-halo-1-lower alkyl thio benzenes. These compounds can then be converted to the corresponding 3-halo-4-(lower alkyl thio)-phenyl acetic acids. First, the 2-halo-1-lower alkyl thio benzenes are acylated with a (lower alkyl)oxalyl chloride (such as methyloxalyl chloride or ethyloxalyl chloride) via a Friedel-Crafts acylation to produce the alpha-keto carboxylic ester in the position para to the lower alkyl thio functional group. The alpha-keto carboxylic ester is next hydrolyzed by any conventional method to convert a alpha-keto carboxylic ester to a alpha-keto carboxylic acid. Wolff-Kishner reduction of the resulting alpha-keto carboxylic acid will produce the compounds of formula V where $R^1$ is halo and $R^2$ is lower alkyl thio (see for example, Levine, S. D. *J. Med. Chem.* 1972, 1029 for a similar reaction sequence). The lower alkyl thio compounds can then be converted to the corresponding lower alkyl sulfonyl compounds of formula V by oxidation. Any conventional method of oxidizing an alkyl thio substituent to the corresponding sulfone group can be utilized to effect this conversion.

For the alkylation reaction using the alkyl halide of formula VII, the carboxylic acids of formula V can be directly alkylated or first converted to the corresponding esters of lower alkyl alcohols of formula VI using any conventional esterification methods and then alkylated. In the alkylation step of the Reaction Scheme, the alkyl halide of formula VII is reacted with the dianion of formula V to produce the compound of formula IX or reacted with the anion of formula VI to produce the compound of formula VIII. The compounds of formula V and VI represent an organic acid and an organic acid derivative having an alpha carbon atom, and the compound of formula VII is an alkyl halide so that alkylation occurs at the alpha carbon atom of this carboxylic acid. This reaction is carried out by any conventional means of alkylation of the alpha carbon atom of a carboxylic acid or a lower alkyl ester of a carboxylic acid. Generally, in these alkylation reactions, an alkyl halide is reacted with the dianion of the acetic acid or the anion generated from an acetic acid ester. The anion can be generated by using a strong organic base such as lithium diisopropylamide or n-butyl lithium as well as other organic lithium bases. In carrying out this reaction, low boiling ether solvents are utilized such as tetrahydrofuran at low temperatures, from −80° C. to about −10° C. being preferred. However, any temperature from −80° C. to room temperature can be used. If necessary, the alkylation reactions may proceed using a triflate alkylation subunit instead of the halo alkylation subunit of compound VII. These triflate alkylation reactions can be preformed according to procedures well-known in the art of synthetic organic chemistry.

If it is desired to produce the compound of formula I where $R^4$ is CONH—$R^6$ and $R^6$ is lower alkyl, the methyl ester of formula VIII is reacted with a lower alkyl urea to produce the compound of formula I. This reaction is carried out by utilizing any conventional means of reacting a methyl ester with a lower alkyl urea to form the corresponding condensation product. The required lower alkyl ureas are commercially available (for example, methylurea, ethylurea n-propylurea, n-butyulurea) or are known in the chemical literature.

Where it is desired to produce the compound of formula I where $R^4$ is an unsubstituted or mono-substituted five- or six-membered heteroaromatic ring, the compound of formula VIII can be converted to the compound of formula IX by any conventional procedure to convert a carboxylic acid ester to an acid. The compound of formula IX is then condensed with the compounds of formula X via conventional peptide coupling to produce the compounds of formula I. In carrying out this reaction, any conventional method of condensing a primary amine with a carboxylic acid can be utilized to effect this conversion. On the other hand, the compound of formula VIII can also be condensed with the compound of formula X via conventional procedures to produce the compound of formula I. In carrying out this reaction, any conventional method of condensing a primary amine with a carboxylic acid ester can be utilized to effect this conversion.

The amino heteroaromatic compounds of formula X are commercially available, or are known in the chemical literature, or can be prepared from those skilled in the art by using adaptions of standard synthetic transformations reported in the chemical literature. For example, the heteroaromatics of formula X, wherein one of the substitutions is —$(CH_2)_n COOR^7$, where n=1, 2, 3, or 4 and $R^7$ is hydrogen or lower alkyl can be prepared from the corresponding carboxylic acid —$(CH_2)_n COOR^7$ (n=0 and $R^7$ is hydrogen). Any conventional carbon homologation method can be utilized to convert a lower carboxylic acid to its higher homologs (see for example, Skeean, R. W.; Goel, O. P. *Synthesis*, 1990, 628), which in turn can then can be converted to the corresponding lower alkyl esters using any conventional esterification methods. The heteroaromatics of formula X, wherein one of the substitutions is —($CH_2$)$_n$C(=O)NHR$^7$, where n=0, 1, 2, 3, or 4 and R$^7$ is hydrogen or lower alkyl can in turn be made by the above mentioned carboxylic acids. Any conventional means of converting carboxylic acids to the corresponding amides may be utilized to effect this conversion. In turn, the lower alkyl amides can be converted to the corresponding amines of formula X, wherein one of the substitutions is —($CH_2$)$_n$NHR$^7$, by any conventional amide reduction method. The heteroaromatics of formula X, wherein one of the claimed substitutions is —($CH_2$)$_n$OR$^7$, where n=1, 2, 3, or 4 can be prepared from the above said corresponding lower alkyl esters. The lower alkyl esters can be converted to the corresponding alcohols using any conventional ester reduction method.

Such amines and alcohols described above would have to be selectively protected before carrying out the condensation step. The amino group and alcohol group can be protected with any conventional acid removable group. The protecting groups are then removed from the amine and alcohol groups after the coupling step to produce the desired compounds of formula I.

The heteroaromatics of formula X, wherein one of the substituents is —C(O)C(O)OR$^7$ or —C(O)—OR$^7$ and R$^7$ is lower alkyl, can be prepared from the corresponding halogen. Any conventional acylation method to convert an aromatic or heteroaromatic halogen to its oxoacetic acid lower ester or ester derivative (see for example, Hayakawa, K.; Yasukouchi, T.; Kanematsu, K. *Tetrahedron Lett*, 1987, 28, 5895) can be utilized. On the other hand, if it is desired to produce compounds with lower alkyl or perfluoro-lower alkyl groups of compounds of formula X, the corresponding halo substituted compounds of formula X can be used as starting materials. Any conventional method of converting an aromatic halo group to the corresponding lower alkyl group or perfluoro-lower alkyl group can be utilized to effect this conversion.

If it is desired to produce the heteroaromatic of formula X wherein one of the substitutions is cyano or the compound of formula I wherein one of the substitutions on the five- or six-membered heteroaromatic ring is cyano, then the corresponding halogen (especially bromo) can be utilized as the starting material. Any conventional method of converting a halogen to a cyanide may be utilized to effect this conversion. On the other hand, if it is desired to produce the compound of formula I wherein one of the substitutions on the five- or six-membered heteroaromatic ring is amidooxime, it is best to form this functional group after the condensation step from the corresponding cyano group. Any conventional method of amidooxime formation from a cyano can be utilized to effect this conversion.

The five- or six-membered ring formed by the combination of R$^3$ and the carbon atom R$^3$ is attached to, hereinafter referred to as —CH<R$^3$, is a polar group. The five- or six-membered ring may consist of all carbon atoms or contain one heteroatom selected from oxygen or sulfur.

If it is desired to produce the compound of formula VIII or IX in which —CH<R$^3$ is 2-tetrahydrofuran, the commercially available starting material, 2-bromomethyl-tetrahydrofuran, may be used as the alkyl halide for the alkylation step. Any conventional means of alkylation of the alpha carbon atom of a carboxylic acid or a lower alkyl ester of a carboxylic acid may be utilized to effect this conversion. Another chemical means to produce the compound of formula VIII or IX in which —CH<R$^3$ is 2-tetrahydrofuran is from the commercially available alcohol, (tetrahydro-furan-2-yl)-methanol. The alcohol may be converted to the iodide. Any conventional method of converting an alcohol to an iodide may be utilized to effect this conversion. The alkyl halide may in turn be used for the alkylation step as described above.

If it is desired to produce a compound of formula VIII or IX in which —CH<R$^3$ is 2(R)-tetrahydrofuran, the commercially available starting material, (R)-(+)-tetrahydro-2-furic acid, may be used. In this reaction sequence, the acid may be reduced to the corresponding alcohol. Any conventional method of converting a carboxylic acid to an alcohol may be utilized to effect this conversion. The resulting alcohol can then be converted to the corresponding triflate for the alkylation step. Any conventional method of converting an alcohol to a triflate may be utilized to effect this conversion, and any conventional means of alkylation of the alpha carbon atom of a carboxylic acid or a lower alkyl ester of a carboxylic acid with an alkyl triflate may be utilized to effect this conversion.

If it is desired to produce a compound of formula VIII or IX in which —CH<R$^3$ is 3-tetrahydrofuran, the commercially available starting material, tetrahydro-3-furanmethanol, may be used. In this reaction sequence, the alcohol can first be converted to the corresponding tosylate. Any conventional method of converting an alcohol to a tosylate may be utilized to effect this conversion. The resulting tosylate may then be converted to the corresponding iodide. Any conventional method of converting a tosylate to an iodide may be utilized to effect this conversion. The subsequent alkylation reaction may then be carried out by any conventional means of alkylation of the alpha carbon atom of a carboxylic acid or a lower alkyl ester of a carboxylic acid.

If it is desired to produce a compound of formula VIII or IX in which —CH<R$^3$ is 2-tetrahydropyran, the commercially available starting material, 2-bromomethyl-tetrahydro-pyran, may be used as the alkyl halide. The alkylation reaction may then be carried out by any conventional means of alkylation of the alpha carbon atom of a carboxylic acid or a lower alkyl ester of a carboxylic acid.

If it is desired to produce a compound of formula VIII or IX in which —CH<R$^3$ is 3(R)-tetrahydrothiopyran, the commercially available starting material, 3,3'-thiodipropionate, may be used. In this reaction sequence, the diester can be cyclized using base. Any conventional method of base-promoted cyclization may be utilized to effect this conversion. The resulting thiopyran may be enzymatically reduced. Any conventional method of chiral reduction may be utilized to effect this conversion. The resulting alcohol can be reduced to the corresponding hydrocarbon. Any conventional method of alcohol reduction may be utilized to effect this conversion. The remaining ester may then be reduced to the alcohol. Any conventional method of converting an ester to an alcohol may be utilized to effect this conversion. The alcohol can then be converted to the alkyl iodide. Any conventional method of converting an alcohol to an iodide may be utilized to effect this conversion. The alkylation reaction may then be carried out by any conventional means of alkylation of the alpha carbon atom of a carboxylic acid or a lower alkyl ester of a carboxylic acid.

If it is desired to produce a compound of formula I in which —CH<R$^3$ is 3-(1-oxo-hexahydro-1$\lambda^4$-thiopyran-3(R)-yl, the starting material may be of the form of formula I containing a 3(R)-tetrahydro-thiopyran subunit at —CH<R$^3$. The thio-ether can be oxidized to the sulfoxide. Any conventional method of oxidizing alkyl thio substituents to sulfoxides can be utilized to effect this conversion.

If it is desired to produce a compound of formula VIII or IX in which —CH<$R^3$ is 4-tetrahydropyran, the known starting material, (tetrahydro-pyran-4-yl)-methanol, may be used. In this reaction sequence, the alcohol may be converted to the tosylate. Any conventional method of converting an alcohol to a tosylate may be utilized to effect this conversion. The tosylate is then converted to the iodide. Any conventional method of converting an alcohol to an iodide may be utilized to effect this conversion. The alkylation reaction may then be carried out by any conventional means of alkylation of the alpha carbon atom of a carboxylic acid or a lower alkyl ester of a carboxylic acid.

If it is desired to produce a compound of formula VIII or IX in which —CH<$R^3$ is 2-hydroxy-cyclopentyl, the commercially available starting material, 2-oxo-cyclopetanecarboxylic acid ethyl ester, may be used. In this reaction sequence, the ketone may be reduced to the alcohol. Any conventional method of reducing a ketone to an alcohol may be utilized to effect this conversion. The resulting alcohol can then be protected using a standard protecting group for an alcohol. Any conventional method of converting an alcohol to a protected alcohol may be utilized to effect this conversion. The ester may be reduced to the corresponding primary alcohol. Any conventional method of reducing an ester to an alcohol may be utilized to effect this conversion. The resulting alcohol can be converted to the iodide. Any conventional method of converting an alcohol to an iodide may be utilized to effect this conversion. The alkylation reaction may then be carried out by any conventional means of alkylation of the alpha carbon atom of a carboxylic acid or a lower alkyl ester of a carboxylic acid. Alternatively, if it is desired to produce a compound of formula I in which —CH<$R^3$ is 2-oxo-cyclopentyl, the starting material may be of the form of formula I containing a 2-hydroxy-cyclopentyl subunit at —CH<$R^3$. The alcohol may be oxidized to the ketone. Any conventional method of oxidizing an alcohol to a ketone may be utilized to effect this conversion.

In an analogous manner:
(a) The desired 3-oxo-cyclohexyl —CH<$R^3$ group can be obtained from ethyl 3-oxocyclohexane-1-carboxylate.
(b) The desired 2-oxo-cyclohexyl —CH<$R^3$ group can be obtained from 2-cyclohexanone carboxylate.

If it is desired to produce a compound of formula I in which —CH<$R^3$ is 2-hydroxyimino-cyclopentyl, the starting material may be of the form of formula I containing a 2-oxo-cyclopentyl subunit at —CH<$R^3$. The ketone may then be converted to the hydroxyimino. Any conventional method of converting a ketone to a hydroxyimino may be utilized to effect this conversion. On the other hand, if it is desired to produce a compound of formula I in which —CH<$R^3$ is 2-methoxyimino-cyclopentyl, the starting material may also be of the form of formula I containing the 2-oxo-cyclopentyl subunit at —CH<$R^3$. The ketone may be converted to the methoxyimino. Any conventional method of converting a ketone to a methoxyimino may be utilized to effect this conversion.

If it is desired to produce a compound of formula VIII in which —CH<$R^3$ is 2,2-difluoro-cyclopentyl, the starting material may be of the form of formula VIII containing a 2-oxo-cyclopentyl subunit at —CH<$R^3$. The ketone may then be converted to the difluoro. Any conventional method of converting a ketone to a difluoro may be utilized to effect this conversion.

If it is desired to produce a compound of formula I in which —CH<$R^3$ is 3-hydroxy-cyclopentyl, the starting material, 3-iodomethyl-cyclopentanone (J. Org. Chem. 1981, 46, 2412-2414), may be used. The ketone can be reduced to the alcohol. Any conventional method of reducing a ketone to an alcohol may be utilized to effect this conversion. The alcohol may be protected using a standard protecting group for an alcohol. Any conventional method of converting an alcohol to a protected alcohol may be utilized to effect this conversion. The alkylation reaction may then be carried out by any conventional means of alkylation of the alpha carbon atom of a carboxylic acid or a lower alkyl ester of a carboxylic acid. The compound of formula VIII is condensed with the compound of formula X via conventional methods to produce the compound of formula I. In carrying out this reaction, any conventional method of condensing a primary amine with a carboxylic acid ester can be utilized to effect this conversion. The alcohol protecting group may then be removed. Any conventional method to remove alcohol protecting groups may be used.

If it is desired to produce a compound of formula I in which —CH<$R^3$ is 3-methoxy-cyclopentyl, the starting material may be of the form of formula I containing a 3-hydroxy-cyclopentyl subunit at —CH<$R^3$. The alcohol can be converted to a methyl ether. Any conventional method of converting an alcohol to a methyl ether may be utilized to effect this conversion. On the other hand, if it is desired to produce a compound of formula I in which —CH<$R^3$ is 3-acetoxy-cyclopentyl, the starting material may also be of the form of formula I containing the 3-hydroxy-cyclopentyl subunit at —CH<$R^3$. The alcohol can be converted to an acetoxy group. Any conventional method of converting an alcohol to an acetoxy may be utilized to effect this conversion.

If it is desired to produce a compound of formula VIII in which —CH<$R^3$ is 3-fluoro-cyclopentyl, the starting material may be of the form of formula VIII containing a 3-hydroxy-cyclopentyl subunit at —CH<$R^3$. The alcohol can be converted to a fluoro. Any conventional method of converting an alcohol to a fluoro may be utilized to effect this conversion.

If it is desired to produce a compound of formula VIII or IX in which —CH<$R^3$ is 3-oxo-cyclopentyl, the starting material 3-iodomethyl-cyclopentanone (J. Org. Chem. 1981, 46, 2412-2414) may be used. The ketone can be protected using a standard protecting group for a ketone. Any conventional method of converting a ketone to a protected ketone may be utilized to effect this conversion. The alkylation reaction may then be carried out by any conventional means of alkylation of the alpha carbon atom of a carboxylic acid or a lower alkyl ester of a carboxylic acid. The protecting group of the ketone can then be removed. Any conventional method of removing a ketone protecting group may be utilized to effect this conversion. If it desired to produce a compound in which the stereochemistry at the branch point off of the 3-oxo-cyclopentyl ring is defined as either R or S, the starting material may be the appropriately chiral-protected form of 2-cyclopentene-1-one. This material can then be converted to the appropriately protected iodide by standard methods.

If it is desired to produce a compound of formula I in which —CH<$R^3$ is 3-hydroxyimino-cyclopentyl, the starting material may be of the form of formula I containing a 3-oxo-cyclopentyl subunit at —CH<$R^3$. The ketone may be converted to the hydroxyimino. Any conventional method of converting a ketone to a hydroxyimino may be utilized to effect this conversion. On the other hand, if it is desired to produce a compound of formula I in which —CH<$R^3$ is 3-methoxyimino-cyclopentyl, the starting material may also be of the form of formula I containing the 3-oxo-cyclopentyl subunit at —CH<R³. The ketone may be converted to the methoxyimino. Any conventional method of converting a ketone to a methoxyimino may be utilized to effect this conversion.

If it is desired to produce a compound of formula VIII in which —CH<R³ is 3,3-difluoro-cyclopentyl, the starting material may be of the form of formula VIII containing a 3-oxo-cyclopentyl subunit at —CH<R³. The ketone may then be converted to the difluoro. Any conventional method of converting a ketone to a difluoro may be utilized to effect this conversion.

If it is desired to produce a compound of formula I in which —CH<R³ is 3-hydroxy-3-methyl-cyclopentyl, the starting material may be of the form of formula I containing a 3-oxo-cyclopentyl subunit at —CH<R³. The ketone may then be converted to the 3-hydroxy-3-methyl compound by any conventional method of converting a ketone to a lower alkyl tertiary alcohol.

If it is desired to produce a compound of formula VIII or IX in which —CH<R³ is 4-oxo-cyclohexyl, the commercially available starting material, 4-cyclohexanonecarboxylic acid ethyl ester, may be used. The ketone may be protected using a standard protecting group. Any conventional method of protecting a ketone may be utilized to effect this conversion. The resulting ester may then be reduced to the alcohol. Any conventional method of reducing an ester to an alcohol may be utilized to effect this conversion. The alcohol can be converted to the iodide. Any conventional method of converting an alcohol to an iodide may be utilized to effect this conversion. The alkylation reaction may then be carried out by any conventional means of alkylation of the alpha carbon atom of a carboxylic acid or a lower alkyl ester of a carboxylic acid. The ketone protecting group may then be removed. Any conventional method to remove a ketone protecting group may be used.

If it is desired to produce a compound of formula I in which —CH<R³ is 4-hydroxyimino-cyclohexyl, the starting material may be of the form of formula I containing a 4-oxo-cyclohexyl subunit at —CH<R³. The ketone may then be converted to the hydroxyimino. Any conventional method of converting a ketone to a hydroxyimino may be utilized to effect this conversion. On the other hand, if it is desired to produce a compound of formula I in which —CH<R³ is 4-methoxyimino-cyclohexyl, the starting material may also be of the form of formula I containing the 4-oxo-cyclohexyl subunit at —CH<R³. The ketone may then be converted to the methoxyimino. Any conventional method of converting a ketone to a methoxyimino may be utilized to effect this conversion.

If it is desired to produce a compound of formula I in which —CH<R³ is 4-hydroxy-cyclohexyl, the starting material may be of the form of formula I containing a 4-oxo-cyclohexyl subunit at —CH<R³. The ketone may be reduced to the alcohol. Any conventional method of converting a ketone to a alcohol may be utilized to effect this conversion.

If it is desired to produce a compound of formula VIII or IX in which —CH<R³ is 3-tetrahydropyran, the commercially available starting material, dihydro-pyran-3-one, may be used. In this reaction sequence, the ketone may be reduced to the alcohol. Any conventional method of reducing a ketone to an alcohol may be utilized to effect this conversion. The alcohol is converted to the mesylate. Any conventional method of converting an alcohol to a mesylate may be utilized to effect this conversion. The mesylate may then be displaced by a cyano group. Any conventional method of converting a mesylate to a cyano may be utilized to effect this conversion. The resulting cyano may then be converted to an acid. Any conventional method of hydrolysis of a cyano to an acid may be utilized to effect this conversion. The acid is then reduced to an alcohol. Any conventional method of reducing an acid to an alcohol may be utilized to effect this conversion. The alcohol may then be converted to an iodide. Any conventional method of converting an alcohol to an iodide may be utilized to effect this conversion. The alkylation reaction may then be carried out by any conventional means of alkylation of the alpha carbon atom of a carboxylic acid or a lower alkyl ester of a carboxylic acid.

In an analogous manner:
(a) The desired 2-tetrahydrothiofuran —CH<R³ group can be made from 4-butyrothiolactone.
(b) The desired 3-tetrahydrothiofuran —CH<R³ group can be made from tetrahydrothiophen-3-one.
(c) The desired 4-tetrahydrothiopyran —CH<R³ group can be made from tetrahydrothiopyran-4-one.

If it is desired to produce a compound of formula VIII or IX in which —CH<R³ is 2-tetrahydrothiopyran, the commercially available starting material, ethyl 2-oxothiane-3-carboxylate, may be used. In this reaction sequence, the ester may be converted to the acid. Any conventional method of converting an ester to an acid may be utilized to effect this conversion. The acid may then be decarboxylated. Any conventional method of decarboxylation may be utilized to effect this conversion. The ketone may then be reduced to the alcohol. Any conventional method of reducing a ketone to an alcohol may be utilized to effect this conversion. The alcohol is converted to the mesylate. Any conventional method of converting an alcohol to a mesylate may be utilized to effect this conversion. The mesylate may then be displaced by a cyano group. Any conventional method of converting a mesylate to a cyano may be utilized to effect this conversion. The resulting cyano may then be converted to an acid. Any conventional method of hydrolysis of a cyano to an acid may be utilized to effect this conversion. The acid is then reduced to an alcohol. Any conventional method of reducing an acid to an alcohol may be utilized to effect this conversion. The alcohol may then be converted to an iodide. Any conventional method of converting an alcohol to an iodide may be utilized to effect this conversion. The alkylation reaction may then be carried out by any conventional means of alkylation of the alpha carbon atom of a carboxylic acid or a lower alkyl ester of a carboxylic acid.

The compound of formula I has an asymmetric carbon atom through which the group —CH₂—CH<R3 and the acid amide substituents are connected. In accordance with this invention, the preferred stereoconfiguration of this group is R.

If it is desired to produce the R or the S isomer of the compounds of formula I, these compounds can be isolated as the desired isomer by conventional chemical means. The preferred chemical mean is the use of pseudoephredrine as a chiral auxiliary for the asymmetric alkylation of the phenylacetic acids of formula V (see for example, Myers, A. G. et al. *J. Am. Chem. Soc.* 1997, 6496). To form the desired R acids of formula IX, the compounds of formula V are first converted to the pseudoephedrine amides using 1R,2R-(−)-pseudoephedrine as the desired enantiomer of pseudoephedrine. Any conventional method of converting a carboxylic acid to a carboxamide can be utilized to effect this conversion. The pseudoephedrine amides can undergo highly diastereoselective alkylations with alkyl halides to afford the cc-substituted amide products corresponding to formula IX. These highly diastereomerically enriched amides can be converted to the highly enantiomerically enriched R carboxylic acids of formula IX by conventional acidic hydrolysis methods to convert a carboxamide to a carboxylic acid. These R carboxylic acids of formula IX can be converted to the R isomers of formula I. In carrying out this reaction, any conventional method of condensing a primary amine with a carboxylic acid can be utilized to effect this conversion.

Another chemical means to produce the R or S isomer of the compounds of formula I is to react the compound of formula IX with an optically active base. Any conventional optically active base can be utilized to carry out this resolution. Among the preferred optically active bases are the optically active amine bases such as alpha-methylbenzylamine, quinine, dehydroabietylamine and alpha-methylnaphthylamine. Any of the conventional techniques utilized in resolving organic acids with optically active organic amine bases can be utilized in carrying out this reaction. In the resolution step, the compound of formula IX is reacted with the optically active base in an inert organic solvent medium to produce salts of the optically active amine with both the R and S isomers of the compound of formula IX. In the formation of these salts, temperatures and pressure are not critical and the salt formation can take place at room temperature and atmospheric pressure. The R and S salts can be separated by any conventional method such as fractional crystallization. After crystallization, each of the salts can be converted to the respective compounds of formula IX in the R and S configuration by hydrolysis with an acid. Among the preferred acids are dilute aqueous acids, i.e., from about 0.001N to 2N aqueous acids, such as aqueous sulfuric or aqueous hydrochloric acid. The configuration of formula IX which is produced by this method of resolution is carried out throughout the entire reaction scheme to produce the desired R or S isomers of formula I.

The resolution of racemates of the compounds of the formula IX can also be achieved via the formation of corresponding diastereomeric esters or amides. These diastereomeric esters or amides can be prepared by coupling the carboxylic acids of the formula IX with a chiral alcohol or a chiral amine. This reaction can be carried out using any conventional method of coupling a carboxylic acid with an alcohol or an amine. The corresponding diastereomers of compounds of the formula IX can then be separated using any conventional separation methods. The resulting pure diastereomeric esters or amides can then be hydrolyzed to yield the corresponding pure R or S isomers. The hydrolysis reaction can be carried out using conventional known methods to hydrolyze an ester or an amide without racemization. Finally, the separation of R and S isomers can also be achieved using an enzymatic ester hydrolysis of any lower alkyl esters corresponding to the compound of the formula VIII (see for example, Ahmar, M.; Girard, C.; Bloch, R, Tetrahedron Lett, 1989, 7053), which results in the formation of corresponding chiral acid and chiral ester. The ester and the acid can be separated by any conventional method of separating an acid from an ester. The configuration of formula VIII which is produced by this method of resolution is carried out throughout the entire reaction scheme to produce the desired R or S isomers of formula I.

All of the compounds of formula I which include the compounds set forth in the Examples, activated glucokinase in vitro by the procedure of Example A. In this manner, they increase the flux of glucose metabolism, which causes increased insulin secretion. Therefore, the compounds of formula I are glucokinase activators useful for increasing insulin secretion.

The following compounds were tested and found to have excellent glucokinase activator in vivo activity when administered orally in accordance with the assay described in Example B:

N-(5-Bromo-pyrazin-2-yl)-2-(3-chloro-4-methanesulfonyl-phenyl)-3-(tetrahydro-pyran-4-yl)-propionamide
2-(3-Chloro-4-methanesulfonyl-phenyl)-N-[5-(N-hydroxy-carbamimidoyl)-pyrazin-2-yl]-3-(tetrahydro-pyran-4-yl)-propionamide
2(R)-(3-Chloro-4-methanesulfonyl-phenyl)-3-(3-oxo-cyclopentyl)-N-pyrazin-2-yl-propionamide
2(R)-(3-Chloro-4-methanesulfonyl-phenyl)-3-((R)-3-oxo-cyclopentyl)-N-pyrazin-2-yl-propionamide
N-(5-Bromo-pyrazin-2-yl)-2-(3-chloro-4-methanesulfonyl-phenyl)-3-(3-oxo-cyclopentyl)-propionamide
N-(5-Bromo-pyrazin-2-yl)-2-(3-chloro-4-methanesulfonyl-phenyl)-3-(3-hydroxyimino-cyclopentyl)-propionamide
2-(3-Chloro-4-methanesulfonyl-phenyl)-3-(3-methoxy-imino-cyclopentyl)-N-pyrazin-2-yl-propionamide
N-(5-Bromo-pyrazin-2-yl)-2-(3-chloro-4-methanesulfonyl-phenyl)-3-(3-methoxyimino-cyclopentyl)-propionamide
N-(5-Bromo-pyrazin-2-yl)-2-(3-chloro-4-methanesulfonyl-phenyl)-3-(4-oxo-cyclohexyl)-propionamide
N-(5-Bromo-pyrazin-2-yl)-2(R)-(3-chloro-4-methanesulfonyl-phenyl)-3-(4-oxo-cyclohexyl)-propionamide
2(R)-(3-Chloro-4-methanesulfonyl-phenyl)-N-(5-chloro-pyrazin-2-yl)-3-(4-oxo-cyclohexyl)-propionamide
N-(5-Bromo-pyrazin-2-yl)-2-(3-chloro-4-methanesulfonyl-phenyl)-3-(4-hydroxyimino-cyclohexyl)-propionamide
N-(5-Bromo-pyrazin-2-yl)-2(R)-(3-chloro-4-methanesulfonyl-phenyl)-3-(4-hydroxyimino-cyclohexyl)-propionamide
2(R)-(3-Chloro-4-methanesulfonyl-phenyl)-N-(5-chloro-pyrazin-2-yl)-3-(4-hydroxyimino-cyclohexyl)-propionamide.

This invention will be better understood from the following examples, which are for purposes of illustration and are not intended to limit the invention defined in the claims, which follow thereafter.

EXAMPLE 1

1-[2-(3,4-Dichloro-phenyl)-3-(tetrahydro-furan-2-yl)-propionyl]-3-methyl-urea

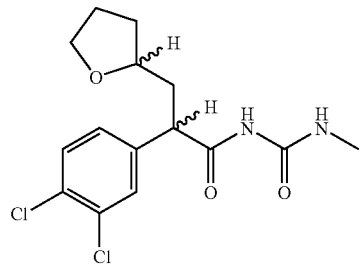

A solution of triphenylphosphine (11.90 g, 45.41 mmol) and imidazole (6.18 g, 90.82 mmol) in methylene chloride (80 mL) cooled to 0° C. was slowly treated with iodine (11.53 g, 45.41 mmol) followed by the dropwise addition of a solution of (tetrahydro-furan-2-yl)-methanol (4.0 mL, 41.28 mmol) in methylene chloride (5 mL). The resulting reaction mixture was allowed to warm to 25° C., where it was stirred for 4 h. The reaction mixture was then diluted with water (25 mL), and the reaction mixture was further extracted with methylene chloride (3×20 mL). The combined organic layers were dried over sodium sulfate, filtered, and concentrated in vacuo at 25° C. The resulting solid was washed with pentane (4×50 mL) and filtered through a pad of silica gel. The filtrate was concentrated in vacuo. Flash chromatography (Merck Silica gel 60, 230-400 mesh, 80/20 pentane/ether) afforded 2-iodomethyl-tetrahydro-furan (2.09 g, 25%) as a clear, colorless liquid: EI-HRMS m/e calcd for $C_5H_9IO$ (M$^+$) 211.9698. found 211.9708.

A solution of (3,4-dichloro-phenyl)-acetic acid (14.0 g, 0.07 mol) in methanol (71 mL) was treated with a catalytic amount of concentrated sulfuric acid. The reaction mixture was heated under reflux for 12 h. The reaction was concentrated in vacuo. Flash chromatography (Merck Silica gel 60, 230-400 mesh, 50/50 hexanes/ethyl acetate) afforded (3,4-dichloro-phenyl)-acetic acid methyl ester (15.0 g, quant.) as a white solid: mp 30-32° C.; EI-HRMS m/e calcd for $C_9H_8Cl_2O_2$ (M+) 217.9901. found 217.9907.

A solution of diisopropylamine (0.59 mL, 4.51 mmol) in tetrahydrofuran (30 mL) was cooled to −78° C. under an argon atmosphere and then was treated with a 2.5M solution of n-butyllithium in hexanes (1.8 mL, 4.51 mmol). The reaction mixture was stirred at −78° C. for 15 min, after which time, a solution of (3,4-dichloro-phenyl)-acetic acid methyl ester (825 mg, 3.76 mmol) in tetrahydrofuran (3 mL) and 1,3-dimethyl-3,4,5,6-tetrahydro-2(1H)-pyrimidinone (1 mL) was slowly added via a cannula. The bright yellow solution was allowed to stir at −78° C. for 1 h, after which time, a solution of 2-iodomethyl-tetrahydro-furan (798 mg, 3.76 mmol) in 1,3-dimethyl-3,4,5,6-tetrahydro-2(1H)-pyrimidinone (0.5 mL) was added via a cannula. The reaction mixture was stirred at −78° C. for 1 h and then allowed to warm to 25° C., where it was stirred for 14 h. The reaction mixture was then quenched by the addition of a saturated aqueous ammonium chloride solution (20 mL) and extracted with ethyl acetate (3×20 mL). The combined organic layers were dried over sodium sulfate, filtered, and concentrated in vacuo. Flash chromatography (Merck Silica gel 60, 230-400 mesh, 90/10 hexanes/ethyl acetate) afforded 2-(3,4-dichloro-phenyl)-3-(tetrahydro-furan-2-yl)-propionic acid methyl ester (501 mg, 44%) as a colorless oil: EI-HRMS m/e calcd for $C_{14}H_{16}Cl_2O_3$ (M+) 302.0477. found 302.0464.

A solution of 2-(3,4-dichloro-phenyl)-3-(tetrahydro-furan-2-yl)-propionic acid methyl ester (617 mg, 2.04 mmol), methylurea (302 mg, 4.07 mmol), and a solution of magnesium methoxide in methanol (7.4 wt. %, 4.63 mL, 3.06 mmol) was heated at 100° C. for 8 h. After this time, the reaction mixture was concentrated in vacuo, dissolved in ethyl acetate (50 mL), and then filtered through a pad of silica gel. The organics were then concentrated in vacuo to give the crude product. Flash chromatography (Merck Silica gel 60, 230-400 mesh, 80/20 hexanes/ethyl acetate) afforded 1-[2-(3,4-dichloro-phenyl)-3-(tetrahydro-furan-2-yl)-propionyl]-3-methyl-urea as a white solid: EI-HRMS m/e calcd for $C_{15}H_{18}Cl_2N_2O_3$ (M+) 344.0694. found 344.0699.

EXAMPLE 2

2-(3,4-Dichloro-phenyl)-3-(tetrahydro-furan-2-yl)-N-thiazol-2-yl-propionamide

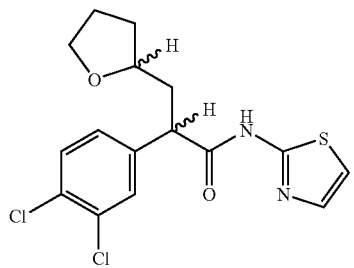

A solution of freshly prepared lithium diisopropylamide (23 mL of a 0.31M stock solution, 7.13 mmol) cooled to −78° C. was treated with (3,4-dichloro-phenyl)-acetic acid (696 mg, 3.39 mmol) in tetrahydrofuran/1,3-dimethyl-3,4,5,6-tetrahydro-2(1H)-pyrimidinone (8.5 mL, 3:1). The resulting solution was stirred at −78° C. for 45 min. At this time, the reaction was treated with a solution of 2-bromomethyl-tetrahydro-furan (672 mg, 4.07 mmol) in 1,3-dimethyl-3,4,5,6-tetrahydro-2(1H)-pyrimidinone (2 mL). The reaction mixture was stirred at −78° C. for 2 h. The reaction was then warmed to 25° C. and was stirred at 25° C. for 18 h. The reaction mixture was then quenched by the dropwise addition of a saturated aqueous ammonium chloride solution. The excess solvent was removed in vacuo. The residue was diluted with water (50 mL) and was treated with a 1N aqueous hydrochloric acid solution until the solution was acidic. The resulting solution was extracted into ethyl acetate (3×50 mL). The organics were washed with a saturated aqueous lithium chloride solution (1×100 mL), dried over sodium sulfate, filtered, and concentrated in vacuo. Flash chromatography (Merck Silica gel 60, 230-400 mesh, 50/50 hexanes/ethyl acetate with glacial acetic acid) afforded 2-(3,4-dichloro-phenyl)-3-(tetrahydro-furan-2-yl)-propionic acid (692.3 mg, 70.8%) as a white solid: mp 100-102° C.; FAB-HRMS m/e calcd for $C^{13}H_{14}Cl_2O_3$ (M+H)+ 289.0399. found 289.0404.

A solution of 2-(3,4-dichloro-phenyl)-3-(tetrahydro-furan-2-yl)-propionic acid (204.5 mg, 0.70 mmol), 2-aminothiazole (71 mg, 0.70 mmol), and benzotriazol-1-yloxytris(dimethylamino)phosphonium hexafluorophosphate (314 mg, 0.70 mmol) in N,N-dimethylformamide (3.55 mL) was treated with N,N-diisopropylethylamine (260 µL, 1.49 mmol). The mixture was stirred under nitrogen at 25° C. for 18 h. At this time, the reaction was diluted with water (50 mL). This solution was extracted with ethyl acetate (3×50 mL). The organics were dried over sodium sulfate, filtered, and concentrated in vacuo. Flash chromatography (Merck Silica gel 60, 230-400 mesh, 50/50 hexanes/ethyl acetate) afforded 2-(3,4-dichloro-phenyl)-3-(tetrahydro-furan-2-yl)-N-thiazol-2-yl-propionamide (232.2 mg, 88.4%) as a white solid: mp 69-71° C.; EI-HRMS m/e calcd for $C_{16}H_{16}Cl_2N_2O_2S$ (M+) 370.0309. found 370.0309.

EXAMPLE 3

2-(4-Methanesulfonyl-phenyl)-3-(tetrahydro-furan-2(R)-yl)-N-thiazol-2-yl-propionamide

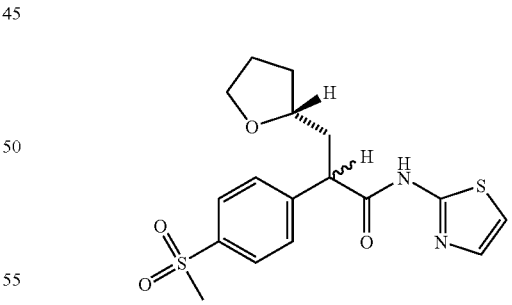

A solution of (R)-(+)-tetrahydro-2-furoic acid (8.0 g, 68.9 mmol) in dry tetrahydrofuran (100 mL) under argon, cooled in an ice bath, was treated dropwise with borane-dimethylsulfide (19.6 mL, 207.0 mmol). The reaction was allowed to warm to 25° C., where it was stirred for 2 h, and was then re-cooled to 0° C. in an ice bath. The reaction was then quenched by the dropwise addition of water. The reaction was diluted with more water (100 mL) and extracted with ethyl acetate 3×75 mL). The combined organic extracts were dried over sodium sulfate, filtered, and concentrated in vacuo. Flash chromatography (Merck Silica gel 60, 230-400 mesh, 25/75 hexanes/ethyl acetate) afforded (R)-(tetrahydro-furan-2-yl)-methanol (5.91 g, 84%) as a colorless oil: $[\alpha]^{23}_{589}$=−16.69° (c=5.2, chloroform).

A solution of (R)-(tetrahydro-thiopyran-3-yl)-methanol (1.0 g, 9.8 mmol) in methylene chloride (35 mL) was cooled to −78° C. and was then treated with 2,6-lutidine (1.71 mL, 14.7 mmol) followed by trifluoromethanesulfonic anhydride (1.98 mL, 11.76 mmol). The reaction was stirred at −78° C. for 40 min and was then diluted with hexanes (40 mL). The mixture was washed with a saturated aqueous sodium bicarbonate solution (1×25 mL). The combined organic extracts were dried over magnesium sulfate, filtered, and concentrated in vacuo to afford trifluoromethanesulfonic acid (R)-tetrahydro-furan-2-yl methyl ester as a crude oil.

A solution of 4-(methylthio)phenylacetic acid (6.91 g, 37.9 mmol) in methanol (100 mL) was treated slowly with concentrated sulfuric acid (1 mL). The resulting reaction mixture was heated under reflux for 19 h. The reaction mixture was allowed to cool to 25° C. and then concentrated in vacuo to remove methanol. The resulting residue was diluted with ethyl acetate (200 mL). The organic layer was washed with a saturated aqueous sodium bicarbonate solution 3×300 mL) and a saturated aqueous sodium chloride solution (1×100 mL). The organic layer was dried over sodium sulfate, filtered, and concentrated in vacuo to afford (4-methylsulfanyl-phenyl)-acetic acid methyl ester (7.28 g, 98%) as a yellow liquid which was used without further purification: EIHRMS m/e calcd for $C_{10}H_{12}O_2S$ ($M^+$) 196.0558. found 196.0559.

A solution of diisopropylamine (1.21 mL, 8.62 mmol) in dry tetrahydrofuran (30 mL) was cooled to −78° C. under argon and was then treated with a 2.5M solution of n-butyllithium in hexanes (3.3 mL, 8.25 mmol). The reaction mixture was stirred at −78° C. for 30 min and then treated dropwise with a solution of (4-methylsulfanyl-phenyl)-acetic acid methyl ester (1.47 g, 7.5 mmol) in dry tetrahydrofuran (10 mL) and 1,3-dimethyl-3,4,5,6-tetrahydro-2(1H)-pyrimidinone (3.34 mL). The reaction mixture turned gold in color and was allowed to stir at −78° C. for 1 h. The reaction mixture was then treated with a solution of trifluoromethanesulfonic acid (R)-tetrahydro-furan-2-yl methyl ester (2.30 g, 9.8 mmol) in dry tetrahydrofuran (10 mL). The reaction mixture was allowed to warm to 25° C., where it was stirred for 16 h. The reaction mixture was quenched with a saturated aqueous ammonium chloride solution (30 mL) and then concentrated in vacuo to remove tetrahydrofuran. The aqueous residue was extracted with ethyl acetate 3×75 mL). The combined organic extracts were dried over sodium sulfate, filtered, and concentrated in vacuo. Biotage chromatography (FLASH 40M, Silica, 9/1 hexanes/ethyl acetate) afforded 2-(4-methylsulfanyl-phenyl)-3-(tetrahydro-furan-2(R)-yl)-propionic acid methyl ester (0.810 g, 39%) as a pale yellow oil: $[\alpha]^{23}_{589}$=−10.87° (c=0.46, chloroform); EI-HRMS m/e calcd for $C_{15}H_{20}O_3S$ ($M^+$) 280.1133. found 280.1130.

A solution of 2-(4-methylsulfanyl-phenyl)-3-(tetrahydro-furan-2(R)-yl)-propionic acid methyl ester (0.693 g, 2.47 mmol) in methanol (10 mL) was treated with a 0.8M aqueous lithium hydroxide solution (4.01 mL, 4.94 mmol). The reaction mixture was stirred at 25° C. for 16 h and then was concentrated in vacuo to remove methanol. The remaining aqueous layer was acidified to pH=2 with a 10% aqueous hydrochloric acid solution and then was extracted with ethyl acetate (2×10 mL). The combined organic layers were washed with a saturated aqueous sodium chloride solution (1×10 mL), dried over sodium sulfate, filtered, and concentrated in vacuo to afford pure 2-(4-methylsulfanyl-phenyl)-3-(tetrahydro-furan-2(R)-yl)-propionic acid (0.653 g, 99%) as a light yellow oil that crystallized upon standing: mp 105-107° C.; $[\alpha]^{23}_{589}$=−14.93° (c=0.75, chloroform); EI-HRMS m/e calcd for $C_{14}H_{18}O_3S$ ($M^+$) 266.0976. found 266.0976.

A solution of 2-(4-methylsulfanyl-phenyl)-3-(tetrahydro-furan-2(R)-yl)-propionic acid (0.075 g, 0.28 mmol), benzotriazol-1-yloxy-tris(dimethylamino)phosphonium hexafluorophosphate (0.186 g, 0.42 mmol), and 2-aminothiazole (0.042 g, 0.42 mmol) in methylene chloride (10 mL) at 25° C. was treated with triethylamine (0.12 mL, 0.84 mmol). The resulting reaction mixture was stirred at 25° C. for 16 h. The reaction mixture was then diluted with water (10 mL) and extracted with methylene chloride 3×10 mL). The combined organic layers were sequentially washed with water (1×10 mL), a 1N aqueous sodium hydroxide solution (1×10 mL), a 1N aqueous hydrochloric acid solution (1×10 mL), and a saturated aqueous sodium chloride solution (1×10 mL). The organic layer was dried over sodium sulfate, filtered, and concentrated in vacuo. Biotage chromatography (FLASH 40S, Silica, 2/3 hexanes/ethyl acetate) afforded 2-(4-methanesulfanyl-phenyl)-3-(tetrahydro-furan-2(R)-yl)-N-thiazol-2-yl-propionamide (0.068 g, 70%) as a pale yellow foam: $[\alpha]^{23}_{589}$=−32.91° (c=0.24, chloroform); EI-HRMS m/e calcd for $C_{17}H_{20}N_2O_2S_2$ ($M^+$) 348.0966. found 348.0968.

A solution of 2-(4-methanesulfanyl-phenyl)-3-(tetrahydro-furan-2(R)-yl)-N-thiazol-2-yl-propionamide (0.061 g, 0.18 mmol) in formic acid (0.20 mL, 5.25 mmol) was cooled to 0° C. and then was treated with a 30% aqueous hydrogen peroxide solution (0.10 mL, 0.875 mmol). The resulting solution was stirred at 0° C. for 5 min and was then warmed to 25° C., where it was stirred for 1 h. The reaction was re-cooled to 0° C. and was then quenched with a 10% aqueous sodium bisulfite solution. The reaction mixture was diluted with water (5 mL) and extracted with ethyl acetate (2×5 mL). The combined organic layers were dried over sodium sulfate, filtered, and concentrated in vacuo. Biotage chromatography (FLASH 40S, Silica, 2/3 hexanes/ethyl acetate) afforded the 2-(4-methanesulfonyl-phenyl)-3-(tetrahydro-furan-2(R)-yl)-N-thiazol-2-yl-propionamide (0.062 g, 70%) as a white foam: $[\alpha]^{23}_{589}$=−33.0° (c=0.20, chloroform); EI-HRMS m/e calcd for $C_{17}H_{20}N_2O_4S_2$ ($M^+$) 380.0864. found 380.0873.

EXAMPLE 4

2-(3-Chloro-4-methanesulfonyl-phenyl)-N-pyrazin-2-yl-3-(tetrahydro-furan-2(R)-yl)-propionamide

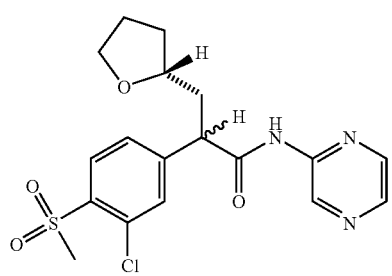

A solution of aluminum trichloride (54.9 g, 412 mmol) in chloroform (180 mL) under argon cooled to 0° C. was treated dropwise with a solution of methyl chlorooxoacetate (24.3 mL, 264 mmol) in chloroform (180 mL). The reaction mixture was stirred at 0° C. for 30 min and then was treated dropwise with a solution of 2-chlorothioanisole (39.4 g, 247 mmol) in chloroform (180 mL). The reaction mixture turned red in color. The resulting reaction mixture was allowed to warm to 25° C., where it was stirred for 4 h. The reaction mixture was then slowly poured onto ice (700 mL). The resulting yellow mixture was stirred for 15 min and then was filtered through celite to remove the aluminum salts. The filtrate was then extracted with methylene chloride 3×50 mL). The combined organic layers were washed with a saturated aqueous sodium bicarbonate solution (1×50 mL). The organics were then dried over magnesium sulfate, filtered, and concentrated in vacuo to afford (3-chloro-4-methylsulfanyl-phenyl)-oxo-acetic acid methyl ester (36.4 g, 60%) as a light yellow oil: EI-HRMS m/e calcd for $C_{10}H_9ClO_3S$ (M$^+$) 243.9961. found 243.9958.

A solution of (3-chloro-4-methylsulfanyl-phenyl)-oxo-acetic acid methyl ester (61.7 g, 252 mmol) in toluene (120 mL) was heated at 50° C. This heated solution was then treated dropwise with a 3M aqueous sodium hydroxide solution (105 mL, 313 mmol) via a dropping funnel, taking care to keep the temperature below 60° C. After the addition was complete, the reaction mixture was stirred at 50° C. for another 1.5 h, during which time, a yellow precipitate began to form. After this time, the heat was removed, and the warm solution was treated dropwise with concentrated hydrochloric acid (10.6 mL, 290 mmol). The resulting reaction mixture was allowed to cool to 25° C. and then was stirred at 25° C. for 16 h. The solid was filtered and then washed with water (50 mL) and toluene (50 mL). The solid was dried by suction for 1 h and then dried in a high vacuum desiccator to afford (3-chloro-4-methylsulfanyl-phenyl)-oxo-acetic acid (57.22 g, 98%) as a white solid: mp 166° C. (dec); FAB-HRMS m/e calcd for $C_9H_7ClO_3S$ (M+Na)$^+$ 252.9702. found 252.9700.

A reaction flask equipped with mechanical stirrer was charged with hydrazine hydrate (8.5 mL, 273 mmol). The hydrazine hydrate was cooled to −50° C. and then treated with (3-chloro-4-methylsulfanyl-phenyl)-oxo-acetic acid (12.6 g, 54.6 mmol) in one portion. An exotherm ensued that raised the temperature. The resulting white milky mixture was then heated to 80° C. After reaching 80° C., the heating element was removed, and the reaction mixture was then treated with potassium hydroxide (2.09 g, 31.7 mmol) in one portion. An exotherm was observed. The reaction was then stirred at 25° C. until the reaction temperature cooled back to 80° C. At this time, another portion of potassium hydroxide (2.09 g, 31.7 mmol) was added. Again, an exotherm was observed, and the resulting reaction mixture was allowed to cool back to 80° C. Once at 80° C., a third portion of potassium hydroxide (2.09 g, 31.7 mmol) was added to the reaction mixture. Another exotherm was observed, and after cooling back to 80° C., the fourth and final portion of potassium hydroxide (2.09 g, 31.7 mmol) was added. At this point, the heating element was added, and the reaction mixture was heated at 100° C. for 16 h. The resulting homogenous reaction mixture was cooled to 25° C. and then diluted with water (12 mL). The reaction mixture was then transferred to a separatory funnel, rinsing with additional water (12 mL) and diethyl ether (40 mL). The layers were separated, and the aqueous layer was transferred to a flask. The organic layer was extracted with water (2×15 mL) The aqueous layers were combined and treated with heptane (20 mL), and the resulting reaction mixture was vigorously stirred. This stirred solution was then treated dropwise with concentrated hydrochloric acid (26 mL) over 30 min while the temperature was kept under 50° C. with an ice bath. A cloudy suspension formed, and this suspension was stirred at 25° C. for 3 h. The solid that formed was collected by filtration and then washed sequentially with a 1N aqueous hydrochloric acid solution (2×6 mL), heptane (1×12 mL), and a solution of heptane/diethyl ether (15 mL, 4:1). The resulting solid was dried under high vacuum to afford (3-chloro-4-methylsulfanyl-phenyl)-acetic acid (10.48 g, 89%) as an off-white solid: mp 105.6-108.4° C.; EI-HRMS m/e calcd for $C_9H_9ClO_2S$ (M$^+$) 216.0012. found 216.0022.

A solution of (3-chloro-4-methylsulfanyl-phenyl)-acetic acid (7.00 g, 32.30 mmol) in methanol (150 mL) was treated slowly with concentrated sulfuric acid (2.8 mL, 52.65 mmol). The resulting reaction mixture was heated under reflux for 1.5 h. The reaction mixture was allowed to cool to 25° C. and then concentrated in vacuo to remove methanol. The residue was diluted with ethyl acetate (500 mL). The organic phase was successively washed with a saturated aqueous sodium bicarbonate solution (1×200 mL) and a saturated aqueous sodium chloride solution (1×200 mL), dried over sodium sulfate, filtered, and concentrated in vacuo to afford (3-chloro-4-methylsulfanyl-phenyl)-acetic acid methyl ester (7.41 g, 99.4%) as a light yellow oil: EI-HRMS m/e calcd for $C_{10}H_{11}ClO_2S$ (M$^+$) 230.0168. found 230.0166.

A solution of (R)-(tetrahydro-thiopyran-3-yl)-methanol (prepared as in Example 3, 0.418 g, 4.095 mmol) in methylene chloride (10 mL) was cooled to −78° C. and was then treated with 2,4,6-collidine (830 µL, 6.3 mmol) followed by trifluoromethanesulfonic anhydride (830 µL, 4.91 mmol). The reaction was stirred at −78° C. for 40 min and was then diluted with hexanes (20 mL). The mixture was washed with a saturated aqueous sodium bicarbonate solution (1×10 mL), and the combined organic extracts were dried over magnesium sulfate, filtered, and concentrated in vacuo to afford trifluoromethanesulfonic acid (R)-tetrahydro-furan-2-yl methyl ester as a crude oil.

A solution of diisopropylamine (0.55 mL, 3.94 mmol) in dry tetrahydrofuran (10 mL) was cooled to −78° C. under argon and was then treated with a 2.5M solution of n-butyllithium in hexanes (1.51 mL, 3.78 mmol). The reaction mixture was stirred at −78° C. for 30 min and then treated dropwise with a solution of (3-chloro-4-methylsulfanyl-phenyl)-acetic acid methyl ester (0.72 g, 3.15 mmol) in dry tetrahydrofuran (3.5 mL) and 1,3-dimethyl-3,4,5,6-tetrahydro-2(1H)-pyrimidinone (1.2 mL). The reaction mixture turned gold in color and was allowed to stir at −78° C. for 1 h. The reaction mixture was then treated with a solution of trifluoromethanesulfonic acid (R)-tetrahydro-furan-2-yl methyl ester (0.959 g, 4.10 mmol) in dry tetrahydrofuran (2 mL). The reaction mixture was allowed to warm to 25° C., where it was stirred for 52 h. The reaction mixture was quenched with a saturated aqueous ammonium chloride solution (25 mL) and then concentrated in vacuo to remove tetrahydrofuran. The aqueous residue was extracted with ethyl acetate 3×50 mL). The combined organic extracts were dried over sodium sulfate, filtered, and concentrated in vacuo. Flash chromatography (Merck Silica gel 60, 230-400 mesh, 9/1 hexanes/ethyl acetate eluted to 85/15 hexanes/ethyl acetate) afforded 2-(3-chloro-4-methylsulfanyl-phenyl)-3-(tetrahydro-furan-2(R)-yl)-propionic acid methyl ester (0.519 g, 52%) as a pale yellow oil: $[\alpha]^{23}_{589}$=−19.02° (c=0.51, chloroform); EI-HRMS m/e calcd for $C_{15}H_{19}ClO_3S$ (M$^+$) 314.0743. found 314.0743.

A solution of 2-(3-chloro-4-methylsulfanyl-phenyl)-3-(tetrahydro-furan-2(R)-yl)-propionic acid methyl ester (0.519 g, 1.65 mmol) in methanol (7 mL) was treated with a 0.8M aqueous lithium hydroxide solution (40.7 mL, 33.0 mmol). The reaction mixture was stirred at 25° C. for 1.5 h and then concentrated in vacuo to remove methanol. The remaining aqueous layer was acidified to pH=2 with a 10% aqueous hydrochloric acid solution and then extracted with ethyl acetate (2×100 mL). The combined organic layers were washed with a saturated aqueous sodium chloride solution (1×100 mL), dried over sodium sulfate, filtered, and concentrated in vacuo to afford pure 2-(3-chloro-4-methylsulfanyl-phenyl)-3-(tetrahydro-furan-2(R)-yl)-propionic acid (0.495 g, 95.8%) as a light yellow oil that crystallized upon standing: mp 93-96° C.; $[\alpha]^{23}_{589}$=−23.70° (c=0.46, chloroform); EI-HRMS m/e calcd for $C_{14}H_{17}ClO_3S$ ($M^+$) 300.0587. found 300.0579.

A solution of 2-(3-chloro-4-methylsulfanyl-phenyl)-3-(tetrahydro-furan-2(R)-yl)-propionic acid (60 mg, 0.2 mmol) in methylene chloride (5 mL) was treated with N,N-dimethylformamide (3 drops) and then cooled to 0° C. The reaction mixture was then treated with a 2.0M solution of oxalyl chloride in methylene chloride (110 µL, 0.22 mmol). The reaction mixture was stirred at 0° C. for 30 min and then was allowed to warm to 25° C. The reaction was concentrated in vacuo to remove solvents and excess oxalyl chloride. The resulting residue was re-dissolved in dry tetrahydrofuran (5 mL) and was treated dropwise with a solution of 2-aminopyrazine (57 mg, 0.6 mmol) in tetrahydrofuran (1 mL) and pyridine (65 µL, 0.8 mmol). The resulting reaction mixture was stirred at 0° C. for 45 min. The reaction mixture was then diluted with water (2 mL) and extracted with methylene chloride 3×5 mL). The combined organic layers were dried over sodium sulfate, filtered, and concentrated in vacuo. Biotage chromatography (FLASH 12M, Silica, 1/4 hexanes/ethyl acetate) afforded 2-(3-chloro-4-methylsulfanyl-phenyl)-N-pyrazin-2-yl-3 (R)-(tetrahydro-furan-2-yl)-propionamide (50 mg, 66.1%) as a colorless gum: $[\alpha]^{23}_{589}$=−43.33° (c=0.45, chloroform); EI-HRMS m/e calcd for $C_{18}H_{20}ClN_3O_2S$ ($M^+$) 377.0965. found 377.0979.

A solution of 2-(3-chloro-4-methylsulfanyl-phenyl)-N-pyrazin-2-yl-3-(tetrahydro-furan-2(R)-yl)-propionamide (0.060 g, 0.16 mmol) in formic acid (0.19 mL, 4.8 mmol) was cooled to 0° C. and then treated with a 30% aqueous hydrogen peroxide solution (0.10 mL, 0.8 mmol). The resulting solution was stirred at 0° C. for 30 min and was then quenched with a 10% aqueous sodium bisulfite solution. The reaction mixture was diluted with water (5 mL) and extracted with ethyl acetate (2×5 mL). The combined organic layers were dried over sodium sulfate, filtered, and concentrated in vacuo. The resulting residue was dissolved in methanol (1 mL) and was treated dropwise with a solution of potassium permanganate (0.028 g, 0.176 mmol) in water (0.5 mL). The dark brown solution was stirred at 25° C. for 30 min, and was then diluted with methanol (10 mL). The reaction mixture was filtered to remove solids, and the filtrate was concentrated in vacuo. Biotage chromatography (FLASH 12M, Silica, 1/1 hexanes/ethyl acetate to 1/4 hexanes/ethyl acetate) afforded the 2-(3-chloro-4-methanesulfonyl-phenyl)-N-pyrazin-2-yl-3-(tetrahydro-furan-2(R)-yl)-propionamide (44 mg, 67.1%) as a colorless gum: $C_{18}H_{20}ClN_3O_4S$ ($M^+$) 409.0863. found 409.0868.

EXAMPLE 5

2-(4-Methanesulfonyl-3-trifluoromethyl-phenyl)-N-pyrazin-2-yl-3-(tetrahydro-furan-2(R)-yl)-propionamide

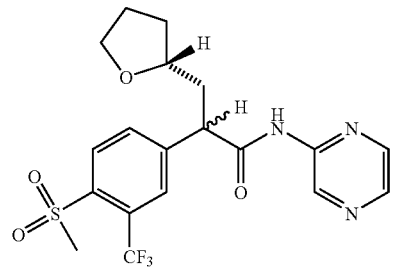

A solution of (4-fluoro-3-trifluoromethyl-phenyl)-acetic acid (4.90 g, 22.06 mmol) in methanol (40 mL) was treated with concentrated sulfuric acid (7 drops). The reaction mixture was heated under reflux for 2 h. The reaction was then concentrated in vacuo. The residue was dissolved in ethyl acetate (100 mL) and washed with a saturated aqueous sodium bicarbonate solution (1×50 mL) and a saturated aqueous sodium chloride solution (1×50 mL). The combined organic layers were dried over sodium sulfate, filtered, and concentrated in vacuo to give (4-fluoro-3-trifluoromethyl-phenyl)-acetic acid methyl ester (5.02 g, 96%) as a colorless oil.

A solution of diisopropylamine (1.86 mL, 13.29 mmol) in dry tetrahydrofuran. (45 mL) cooled to −78° C. under argon was treated with a 2.5M solution of n-butyllithium in hexanes (5.10 mL, 12.75 mmol). The reaction mixture was stirred at −78° C. for 30 min and then was treated dropwise with a solution of (4-fluoro-3-trifluoromethyl-phenyl)-acetic acid methyl ester (2.51 g, 10.63 mmol) in dry tetrahydrofuran (15 mL) and 1,3-dimethyl-3,4,5,6-tetrahydro-2(1H)-pyrimidinone (6.5 mL). The reaction mixture turned gold in color and was allowed to stir at −78° C. for 1 h. At this time, the reaction was treated with a solution of trifluoromethanesulfonic acid (R)-tetrahydro-furan-2-yl methyl ester (prepared as in Example 3, 3.23 g, 13.81 mmol) in dry tetrahydrofuran (15 mL). The reaction mixture was allowed to warm to 25° C., where it was stirred for 16 h. The reaction mixture was then quenched with a saturated aqueous ammonium chloride solution (30 mL) and was then concentrated in vacuo to remove tetrahydrofuran. The aqueous residue was extracted with ethyl acetate (3×150 mL). The combined organic extracts were dried over sodium sulfate, filtered, and concentrated in vacuo. Biotage chromatography (FLASH 40M, Silica, 85/15 hexanes/ethyl acetate) afforded 2-(4-fluoro-3-trifluoromethyl-phenyl)-3-(tetrahydro-furan-2(R)-yl)-propionic acid methyl ester (2.50 g, 39%) as a colorless oil: $[\alpha]^{23}_{589}$=−18.62° (c=0.29, chloroform); EI-HRMS m/e calcd for $C_{15}H_{20}O_3S$ $(M+Na)^+$ 343.0928. found 343.0927.

A solution of 2-(4-fluoro-3-trifluoromethyl-phenyl)-3-(tetrahydro-furan-2(R)-yl)-propionic acid methyl ester (1.97 g, 6.15 mmol) in dry N,N-dimethylformamide (20 mL) at 25° C. under argon was carefully treated with sodium thiomethoxide (0.680 g, 9.27 mmol) and was then heated at 100° C, for 3 h. The reaction mixture was then concentrated in vacuo to remove N,N-dimethylformamide. The remaining residue was suspended in a saturated aqueous ammonium chloride solution (100 mL) and was extracted with ethyl acetate (2×200 mL). The combined organic extracts were dried over sodium sulfate, filtered, and concentrated in vacuo. The resulting residue was then dissolved in methanol (40 mL) and was treated with a 0.8M aqueous lithium hydroxide solution (20.60 mL, 16.7 mmol). The reaction mixture was stirred at 25° C. for 16 h and then was concentrated in vacuo to remove methanol. The remaining aqueous layer was acidified to pH=2 with a 10% aqueous hydrochloric acid solution and then was extracted with ethyl acetate (2×200 mL). The combined organic layers were washed with a saturated aqueous sodium chloride solution (1×100 mL), dried over sodium sulfate, filtered, and concentrated in vacuo to afford pure 2-(4-methylsulfanyl-3-trifluoromethyl-phenyl)-3-(tetrahydro-furan-2(R)-yl)-propionic acid (1.71 g, 83%) as a light yellow oil: $[\alpha C]^{23}{}_{589}$=−23.26° (c=0.49, chloroform); EI-HRMS m/e calcd for $C_{15}H_{17}F_3O_3S$ $(M-H_2O)^+$ 316.0744. found 316.0749.

A solution of 2-(4-methylsulfanyl-3-trifluoromethyl-phenyl)-3-(tetrahydro-furan-2(R)-yl)-propionic acid (67 mg, 0.20 mmol) in methylene chloride (5 mL) was treated with N,N-dimethylformamide (3 drops) and then cooled to 0° C. The reaction mixture was then treated with a 2.0M solution of oxalyl chloride in methylene chloride (0.11 mL, 0.22 mmol). The reaction mixture was stirred at 0° C. for 30 min, allowed to warm to 25° C., and then was concentrated in vacuo to remove solvents and excess oxalyl chloride. The resulting residue was re-dissolved in dry tetrahydrofuran (5 mL) and was treated dropwise with a solution of 2-aminopyrazine (57 mg, 0.60 mmol) in tetrahydrofuran (2 mL) and pyridine (0.065 mL, 0.80 mmol). The resulting reaction mixture was stirred at 25° C. for 1.5 h. The reaction mixture was then diluted with water (50 mL) and extracted with methylene chloride 3×50 mL). The combined organic layers were dried over sodium sulfate, filtered, and concentrated in vacuo. Biotage chromatography (FLASH 12M, Silica, 1/1 hexanes/ethyl acetate) afforded 2-(4-methylsulfanyl-3-trifluoromethyl-phenyl)-N-pyrazin-2-yl-3-(tetrahydro-furan-2(R)-yl)-propionamide (51 mg, 61%) as a colorless gum: EI-HRMS m/e calcd for $C_{19}H_{20}F_3N_3O_2S$ $(M)^+$ 411.1228. found 411.1229.

A solution of 2-(4-methylsulfanyl-3-trifluoromethyl-phenyl)-N-pyrazin-2-yl-3-(tetrahydro-furan-2(R)-yl)-propionamide (0.054 g, 0.13 mmol) in formic acid (0.16 mL, 3.0 mmol) cooled to 0° C. was treated with a 30% aqueous hydrogen peroxide solution (0.08 mL, 0.65 mmol). The resulting solution was stirred at 0° C. for 30 min and was then quenched with a 10% aqueous sodium bisulfite solution. The reaction mixture was diluted with water (5 mL) and extracted with ethyl acetate (2×5 mL). The combined organic layers were dried over sodium sulfate, filtered, and concentrated in vacuo. The resulting residue was dissolved in methanol (1 mL) and was treated dropwise with a solution of potassium permanganate (0.023 g, 0.143 mmol) in water (0.5 mL). The dark brown solution was stirred at 25° C. for 30 min and then was diluted with methanol (10 mL). The reaction mixture was filtered to remove solids, and the filtrate was concentrated in vacuo. Biotage chromatography (FLASH 12M, Silica, 7/3 hexanes/ethyl acetate to 1/1 hexanes/ethyl acetate) afforded 2-(4-methanesulfonyl-3-trifluoromethyl-phenyl)-N-pyrazin-2-yl-3-(tetrahydro-furan-2(R)-yl)-propionamide (33 mg, 57.3%) as a colorless gum: EI-HRMS m/e calcd for $C_{19}H_{20}F_3N_3O_4S$ $(M)^+$ 443.1127. found 443.1137.

EXAMPLE 6

2-(3-Chloro-4-methanesulfonyl-phenyl)-N-pyrazin-2-yl-3-(tetrahydro-furan-3-yl)-propionamide

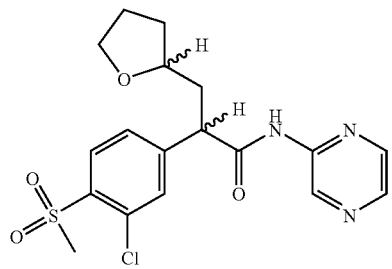

A solution of tetrahydro-3-furanmethanol (3.0 g, 29.4 mmol) in methylene chloride (45 mL) at 25° C. was treated with 4-(dimethylamino)pyridine (3.99 g, 32.31 mmol) and p-toluenesulfonyl chloride (5.60 g, 29.37 mmol), and the reaction mixture was allowed stir at 25° C. overnight. The reaction was then transferred to a separatory funnel and was then washed with a 1N aqueous hydrochloric acid solution (30 mL) and a saturated aqueous sodium bicarbonate solution (20 mL). The organic layer was then dried over sodium sulfate, filtered, and concentrated in vacuo. Biotage chromatography (FLASH 40M, Silica, 60/40 hexanes/ethyl acetate) afforded toluene-4-sulfonic acid tetrahydro-furan-3-yl methyl ester (6.57 g, 97%) as a colorless oil: $(ES)^+$-HRMS m/e calcd for $C_{12}H_{16}O_4S$ $(M+Na)^+$ 279.0661. found 279.0664.

A solution of toluene-4-sulfonic acid tetrahydro-furan-3-yl methyl ester (6.50 g, 25.36 mmol), sodium iodide (11.02 g, 73.54 mmol), and acetone (200 mL) was heated to 60° C. for 16 h. The resulting suspension was then cooled to 10° C. and filtered. The salts were rinsed with cold acetone (50 mL). The filtrate and washings were then concentrated in vacuo to a thick slurry. To this slurry was added methylene chloride (100 mL), and the precipitate was filtered off and washed with methylene chloride (20 mL). The filtrate and washings were then dried over magnesium sulfate, filtered through a pad a silica gel, and then concentrated in vacuo to afford 3-iodomethyl-tetrahydro-furan as a light yellow oil.

A solution of diisopropylamine (0.84 mL, 5.98 mmol) in tetrahydrofuran (10 mL) was cooled to −78° C. under an argon atmosphere and then was treated with a 2.5M solution of n-butyllithium in hexanes (2.29 mL, 5.72 mmol). The reaction mixture was stirred at −78° C. for 15 min. At this time, the reaction was slowly treated with a solution of (3-chloro-4-methylsulfanyl-phenyl)-acetic acid methyl ester (prepared as in Example 4, 1.20 g, 5.20 mmol) in tetrahydrofuran (5 mL) and 1,3-dimethyl-3,4,5,6-tetrahydro-2(1H)-pyrimidinone (0.75 mL). The bright yellow solution was allowed to stir at −78° C. for 1 h, after which time, a solution of 3-iodomethyl-tetrahydro-furan (2.21 g, 10.4 mmol) in 1,3-dimethyl-3,4,5,6-tetrahydro-2(1H)-pyrimidinone (0.69 mL) and tetrahydrofuran (5 mL) was added via a cannula. The reaction mixture was then allowed to warm to 25° C., where it was stirred for 48 h. The reaction mixture was then quenched by the addition of a saturated aqueous ammonium chloride solution (30 mL) and extracted with ethyl acetate 3×30 mL). The organic layers were then combined and washed with a 10% aqueous sulfuric acid solution (25 mL) and a saturated aqueous sodium bicarbonate solution (25 mL). The combined organic layers were then dried over sodium sulfate, filtered, and concentrated in vacuo. Biotage chromatography (FLASH 40M, Silica, 75/25 hexanes/ethyl acetate) afforded 2-(3-chloro-4-methylsulfanyl-phenyl)-3-(tetrahydro-furan-3-yl-propionic acid methyl ester (663 mg, 41%) as a light yellow oil: EI-HRMS m/e calcd for $C_{15}H_{19}ClO_3S$ (M$^+$) 314.0743. found 314.0729.

A solution of 2-(3-chloro-4-methylsulfanyl-phenyl)-3-(tetrahydro-furan-3-yl)-propionic acid methyl ester (663 mg, 2.11 mmol) in formic acid (0.79 mL) and tetrahydrofuran (2.89 mL) was cooled in an ice bath to 0° C. and then was treated with a 30% aqueous hydrogen peroxide solution (1.19 mL, 10.53 mmol). The reaction was then slowly warmed to 25° C. and was stirred at 25° C. for 16 h. At this time, the reaction was cooled to 0° C. and was then quenched with a saturated aqueous sodium sulfite solution. This solution was extracted with ethyl acetate 3×20 mL). The combined organic layers were dried over sodium sulfate, filtered, and concentrated in vacuo. Biotage chromatography (FLASH 40S, Silica, 50/50 hexanes/ethyl acetate) afforded 2-(3-chloro-4-methanesulfonyl-phenyl)-3-(tetrahydro-furan-3-yl)-propionic acid methyl ester (729 mg, 100%) as a white waxy solid: (ES)$^+$-HRMS m/e calcd for $C_{15}H_{19}ClO_5S$ (M+Na)$^+$ 369.0534. found 369.0536.

A solution of 2-(3-chloro-4-methanesulfonyl-phenyl)-3-(tetrahydro-furan-3-yl)-propionic acid methyl ester (729 mg, 2.10 mmol) in ethanol (20 mL) was treated with a solution of potassium hydroxide (694 mg, 10.51 mmol) in water (7 mL). The reaction was stirred for 3 h at 25° C., concentrated in vacuo to remove the ethanol, and then was acidified to pH=2 with a 1N aqueous hydrochloric acid solution. The resulting mixture was then extracted with methylene chloride 3×10 mL). The organic layers were dried over sodium sulfate, filtered, and concentrated in vacuo to afford 2-(3-chloro-4-methanesulfonyl-phenyl)-3-(tetrahydro-furan-3-yl)-propionic acid (654 mg, 94%) as a white foam: (ES)$^+$-HRMS m/e calcd for $C_{14}H_{17}ClO_5S$ (M+Na)$^+$ 355.0377. found 355.0382.

A solution of triphenylphosphine (118 mg, 0.45 mmol) in methylene chloride (5 mL) cooled to 0° C. was treated with N-bromosuccinimide (91 mg, 0.51 mmol). Upon complete dissolution, the cooled, purple solution was then treated with 2-(3-chloro-4-methanesulfonyl-phenyl)-3-(tetrahydro-furan-3-yl)-propionic acid (100 mg, 0.30 mmol). The resulting reaction mixture was stirred at 0° C. for 20 min then warmed to 25° C., where it was stirred for another 30 min. The purple reaction mixture was then treated with 2-aminopyrazine (43 mg, 0.45 mmol) and pyridine (0.07 mL, 0.90 mmol) and stirred for 16 h at 25° C. The reaction was then diluted with water (10 mL) and extracted with methylene chloride 3×15 mL). The organics were dried over sodium sulfate, filtered, and concentrated in vacuo. Biotage chromatography (FLASH 12M, Silica, 1.5/98.5 methylene chloride/methanol) afforded 2-(3-chloro-4-methanesulfonyl-phenyl)-N-pyrazin-2-yl-3-(tetrahydro-furan-3-yl)-propionamide (46 mg, 37%) as a light orange foam: (ES)$^+$-HRMS m/e calcd for $C_{18}H_{20}ClN_3O_4S$ (M+H)$^+$ 410.0936. found 410.0940.

EXAMPLE 7

1-[2-(3,4-Dichloro-phenyl)-3-(tetrahydro-pyran-2-yl)-propionyl]-3-methyl urea

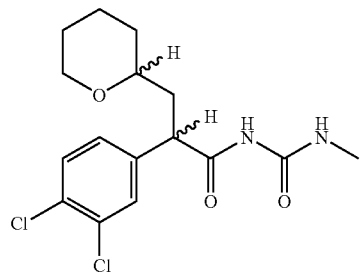

A solution of diisopropylamine (2.63 mL, 18.2 mmol) in tetrahydrofuran (120 mL) cooled to −78° C. under an argon atmosphere was treated with a 2.0M solution of n-butyllithium in hexanes (9.1 mL, 18.2 mmol). The reaction mixture was stirred at −78° C. for 15 min, after which time, a solution of (3,4-dichloro-phenyl)-acetic acid methyl ester (prepared as in Example 1, 3.62 g, 16.5 mmol) in tetrahydrofuran (20 mL) and 1,3-dimethyl-3,4,5,6-tetrahydro-2(1H)-pyrimidinone (6 mL) was slowly added via a cannula. The bright yellow solution was allowed to stir at −78° C. for 1 h, after which time, a solution of 2-bromomethyl-tetrahydro-pyran (2.5 mL, 19.8 mmol) in 1,3-dimethyl-3,4,5,6-tetrahydro-2(1H)-pyrimidinone (4 mL) was added via a cannula. The reaction mixture was then allowed to warm to 25° C., where it was stirred for 16 h. The reaction mixture was then quenched by the addition of a saturated aqueous ammonium chloride solution (30 mL) and then extracted with ethyl acetate 3×40 mL). The combined organic layers were dried over sodium sulfate, filtered, and concentrated in vacuo. Flash chromatography (Merck Silica gel 60, 230-400 mesh, 90/10 hexanes/ethyl acetate) afforded 2-(3,4-dichloro-phenyl)-3-tetrahydro-pyran-2-yl)-propionic acid methyl ester (4.68 g, 89%) as a colorless oil: EI-HRMS m/e calcd for $C_{15}H_{18}Cl_2O_3$ (M$^+$) 316.0633. found 316.0625.

A solution of 2-(3,4-dichloro-phenyl)-3-tetrahydro-pyran-2-yl)-propionic acid methyl ester (374 mg, 1.19 mmol), methylurea (176 mg, 2.38 mmol), and a solution of magnesium methoxide in methanol (7.4 wt. % , 2.5 mL, 1.78 mmol) was heated at 100° C. for 8 h. Over time, the reaction mixture turned cloudy in appearance. At this time, the reaction was concentrated in vacuo. The residue was dissolved in ethyl acetate (10 mL) and then filtered through a pad of silica gel. The filtrate was then concentrated in vacuo. Flash chromatography (Merck Silica gel 60, 230-400 mesh, 95/5 hexanes/ethyl acetate to 60/40 hexanes/ethyl acetate) afforded the two diastereomeric pairs of 1-[2-(3,4-dichloro-phenyl)-3-(tetrahydro-pyran-2-yl)-propionyl]-3-methyl urea (76 mg, 19%) as white solids: (1) first pair of diastereomers: mp 172.8-174.2° C.; EI-HRMS m/e calcd for $C_{16}H_{20}Cl_2N_2O_3$ (M$^+$) 358.0851. found 358.0848; (2) second pair of diastereomers: EI-HRMS m/e calcd for $C_{16}H_{20}Cl_2N_2O_3$ (M$^+$) 358.0851. found 358.0848.

EXAMPLE 8

1-[2-(4-Methanesulfonyl-phenyl)-3-(tetrahydro-pyran-2-yl)-propionyl]-3-methyl-urea

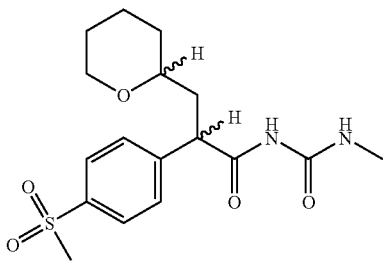

A solution of 4-(methanesulfonyl)phenyl acetic acid (43.63 g, 0.204 mol) in methanol (509 mL) was treated slowly with concentrated sulfuric acid (2 mL). The resulting reaction mixture was heated under reflux for 19 h. The reaction mixture was allowed to cool to 25° C. and then concentrated in vacuo to remove methanol. The residue was diluted with ethyl acetate (800 mL). The organic phase was washed with a saturated aqueous sodium bicarbonate solution (1×200 mL) and a saturated aqueous sodium chloride solution (1×200 mL), dried over sodium sulfate, filtered, and concentrated in vacuo. Flash chromatography (Merck Silica gel 60, 70-230 mesh, 1/1 hexanes/ethyl acetate) afforded 4-(methanesulfonyl)phenyl acetic acid methyl ester (45.42 g, 98%) as a yellow oil which solidified to a cream colored solid upon sitting over time at 25° C.: mp 78-80° C.; EI-HRMS m/e calcd for $C_{10}H_{12}O_4S$ (M+) 228.0456. found 228.0451.

A solution of diisopropylamine (0.67 mL, 4.82 mmol) in tetrahydrofuran (30 mL) cooled to −78° C. under an argon atmosphere was treated with a 2.5M solution of n-butyllithium in hexanes (1.93 mL, 4.82 mmol). The reaction mixture was stirred at −78° C. for 15 min. At this time, the reaction was treated with a solution of (4-methanesulfonyl-phenyl)-acetic acid methyl ester (1.00 g, 4.38 mmol) in tetrahydrofuran (6 mL) and 1,3-dimethyl-3,4,5,6-tetrahydro-2(1H)-pyrimidinone (2 mL). The bright yellow solution was allowed to stir at −78° C. for 1 h, after which time, a solution of 2-bromomethyl-tetrahydro-pyran (0.67 mL, 5.26 mmol) in 1,3-dimethyl-3,4,5,6-tetrahydro-2(1H)-pyrimidinone (1 mL) was added via a cannula. The reaction mixture was then allowed to warm to 25° C., where it was stirred for 16 h. The reaction mixture was then quenched by the addition of a saturated aqueous ammonium chloride solution (20 mL) and extracted with ethyl acetate 3×15 mL). The organic layers were dried over sodium sulfate, filtered, and concentrated in vacuo. Biotage chromatography (FLASH 40M, Silica, 70/30 hexanes/ethyl acetate) afforded 2-(4-methanesulfonyl-phenyl)-3-(tetrahydro-pyran-2-yl)-propionic acid methyl ester (157 mg, 11%) as a colorless oil: EI-HRMS m/e calcd for $C_{16}H_{22}O_5S$ (M+) 326.1188. found 326.1189.

A solution of 2-(4-methanesulfonyl-phenyl)-3-(tetrahydro-pyran-2-yl)-propionic acid methyl ester (75 mg, 0.23 mmol), methylurea (34 mg, 0.46 mmol), and a solution of magnesium methoxide in methanol (7.4 wt. %, 0.49 mL, 0.35 mmol) and methanol (0.5 mL) was heated at 100° C. for 8 h. Over time, the reaction mixture turned cloudy in appearance. At this time, the reaction was concentrated in vacuo. The residue was dissolved in ethyl acetate (10 mL) and then filtered through a pad of silica gel. The filtrate was concentrated in vacuo. Biotage chromatography (FLASH 12M, Silica, 30/70 hexanes/ethyl acetate) afforded 1-[2-(4-methanesulfonyl-phenyl)-3-(tetrahydro-pyran-2-yl)-propionyl]-3-methyl-urea (5 mg, 6%) as a colorless oil: FAB-HRMS m/e calcd for $C_{17}H_{24}N_2O_5S$ (M+H)+ 369.1484. found 369.1495.

EXAMPLE 9

2-(3,4-Dichloro-phenyl)-3-(tetrahydro-pyran-2-yl)-N-thiazol-2-yl-propionamide

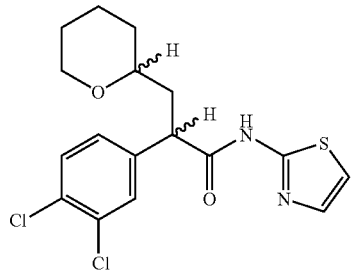

A solution of 2-(3,4-dichloro-phenyl)-3-tetrahydro-pyran-2-yl)-propionic acid methyl ester (prepared as in Example 7, 4.68 g, 14.75 mmol) in ethanol (150 mL) was treated with a solution of potassium hydroxide (1.66 g, 29.50 mmol) in water (16 mL), and the reaction was stirred for at 25° C. 1 h. The reaction was then diluted with water (50 mL), concentrated in vacuo to remove the ethanol, and then acidified to pH=2 with a 1N aqueous hydrochloric acid solution. The product was then extracted with methylene chloride 3×20 mL), and the combined organic layers were dried over sodium sulfate, filtered, and concentrated in vacuo. Flash chromatography (Merck Silica gel 60, 230-400 mesh, 90/10 methylene chloride/methanol plus 1% acetic acid) afforded 2-(3,4-dichloro-phenyl)-3-(tetrahydro-pyran-2-yl)-propionic acid (3.91 g, 87%) as a clear colorless oil: EI-HRMS m/e calcd for $C_{14}H_{16}Cl_2O_3$ (M+) 302.04765. found 302.0473.

A solution of 2-(3,4-dichloro-phenyl)-3-(tetrahydro-pyran-2-yl)-propionic acid (81 mg, 0.27 mmol) in N,N-dimethylformamide (5 mL) was treated with 0-benzotriazol-1-yl-N,N,N',N'-tetramethyluronium hexafluorophosphate (112 mg, 0.29 mmol), N,N-diisopropylethylamine (0.14 mL. 0.80 mmol), and 2-aminothiazole (40 mg, 0.40 mmol). The reaction was stirred at 25° C. for 16 h. At this time, the reaction was diluted with water (10 mL) and extracted with ethyl acetate 3×15 mL). The combined organic layers were washed with water (1×10 mL), a 1N aqueous sodium hydroxide solution (1×10 mL), a 1N aqueous hydrochloric acid solution (1×10 mL), and a saturated aqueous sodium chloride solution (1×10 mL), dried over sodium sulfate, filtered, and concentrated in vacuo. Flash chromatography (Merck Silica gel 60, 230-400 mesh, 90/10 hexanes/ethyl acetate to 60/40 hexanes/ethyl acetate) afforded 2-(3,4-dichloro-phenyl)-3-(tetrahydro-pyran-2-yl)-N-thiazol-2-yl-propionamide (35 mg, 34%) as a light yellow oil: EI-HRMS m/e calcd for $C_{17}H_{18}Cl_2N_2O_2S$ (M+) 384.0466. found 384.0468.

EXAMPLE 10

2(R)-(3,4-Dichloro-phenyl)-3-(tetrahydro-pyran-2-yl)-N-thiazol-2-yl-propionamide

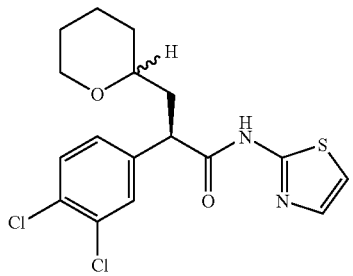

A solution of 2-(3,4-dichloro-phenyl)-3-(tetrahydro-pyran-2-yl)-propionic acid (prepared as in Example 9, 2.56 g, 8.44 mmol) in tetrahydrofuran (80 mL) cooled to −78° C. was treated with triethylamine (1.30 mL, 9.65 mmol) followed by trimethylacetyl chloride (1.10 mL, 8.84 mmol). The resulting white slurry was stirred at −78° C. for 15 min and then at 0° C. for 45 min. In a separate flask, a solution of (S)-4-isopropyl-2-oxazolidinone (1.04 g, 8.04 mmol) in tetrahydrofuran (40 mL) cooled to −78° C. was treated with a 2.5M solution of n-butyllithium in hexanes (3.4 mL, 8.44 mmol). The solution was stirred at −78° C. for 10 min and then was allowed to warm to 25° C., where it was stirred for an additional 10 min. At this time, the first reaction mixture was re-cooled to −78° C. The second reaction mixture was added to the first reaction mixture over a period of 5 min via a cannula. The combined reaction mixture was then stirred at −78° C. for 15 min and then was allowed to warm to 25° C., where it was stirred for an additional 1.5 h. At this time, the reaction was quenched by the addition of a saturated aqueous sodium bisulfite solution (25 mL) and then was extracted with ethyl acetate 3×30 mL). The combined organic layers were washed with a saturated aqueous sodium bicarbonate solution (1×15 mL) and a saturated aqueous sodium chloride solution (1×15 mL), dried over sodium sulfate, filtered, and concentrated in vacuo. Flash chromatography (Merck Silica gel 60, 230-400 mesh, hexanes to 80/20 hexanes/ethyl acetate) afforded two products: (1) 3-[2(S)-(3,4-dichloro-phenyl)-3-(tetrahydro-pyran-2-yl)-propionyl]-4(S)-isopropyl-oxazolidin-2-one (506 mg, 15%) as a clear colorless oil; and (2) 3-[2(R)-(3,4-dichloro-phenyl)-3-(tetrahydro-pyran-2-yl)-propionyl]-4(S)-isopropyl-oxazolidin-2-one (560 mg, 17%) as a clear colorless oil.

A solution of 3-[2(R)-(3,4-dichloro-phenyl)-3-(tetrahydro-pyran-2-yl)-propionyl]-4(S)-isopropyl-oxazolidin-2-one (560 mg, 1.40 mmol) in tetrahydrofuran (30 mL) and water (10 mL) cooled to 0° C. was treated with a 30% aqueous hydrogen peroxide solution (0.7 mL) and lithium hydroxide (117 mg, 2.80 mmol). The reaction was stirred at 0° C. for 1 h. At this time, the reaction was quenched with an aqueous sodium sulfite solution (0.71 g, 5.6 mmol in 4 mL) followed by the addition of a 0.5N aqueous sodium bicarbonate solution (13 mL). The tetrahydrofuran was then removed in vacuo. The residue was diluted with water (60 mL) and extracted with methylene chloride 3×20 mL). The aqueous layer was then acidified to pH=2 with a 5N aqueous hydrochloric acid solution and then was extracted with ethyl acetate (4×25 mL). The combined organic layers were then dried over sodium sulfate, filtered, and concentrated in vacuo to afford 2(R)-(3,4-dichloro-phenyl)-3-(tetrahydro-pyran-2-yl)-propionic acid (203 mg, 48%) as clear colorless oil.

A solution of 2(R)-(3,4-dichloro-phenyl)-3-(tetrahydro-pyran-2-yl)-propionic acid (80 mg, 0.26 mmol), benzotriazol-1-yloxy-tris(dimethylamino)phosphonium hexafluoro-phosphate (177 mg, 0.40 mmol), and 2-aminothiazole (40 mg, 0.40 mmol) in methylene chloride (10 mL) at 25° C. was treated with triethylamine (0.11 mL, 0.79 mmol). The resulting reaction mixture was stirred at 25° C. for 16 h. The reaction mixture was then diluted with water (10 mL) and extracted with methylene chloride 3×10 mL). The combined organic layers were sequentially washed with water (1×10 mL), a 1N aqueous sodium hydroxide solution (1×10 mL), a 1N aqueous hydrochloric acid solution (1×10 mL), and a saturated sodium chloride solution (1×10 mL). The organic layer was dried over sodium sulfate, filtered, and concentrated in vacuo. Flash chromatography (Merck Silica gel 60, 230-400 mesh, 95/5 hexanes/ethyl acetate to 70/30 hexanes/ethyl acetate) afforded the 2(R)-(3,4-dichloro-phenyl)-3-(tetrahydro-pyran-2-yl)-N-thiazol-2-yl-propionamide (57 mg, 57%) as a white foam: EI-HRMS m/e calcd for $C_{17}H_{18}Cl_2N_2O_2S$ (M$^+$) 384.066. found 384.1467.

EXAMPLE 11

2-(4-Methanesulfonyl-phenyl)-3-(tetrahydro-pyran-2-yl)-N-thiazol-2-yl-propionamide

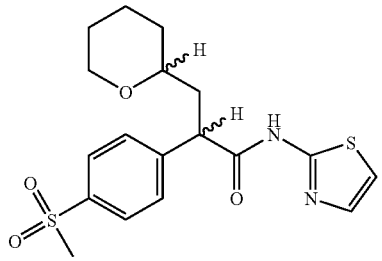

A solution of 2-(4-methanesulfonyl-phenyl)-3-(tetrahydro-pyran-2-yl)-propionic acid methyl ester (prepared as in Example 8, 75 mg, 0.23 mmol) in ethanol (5 mL) was treated with a solution of potassium hydroxide (32 mg, 0.58 mmol) in water (1 mL). The reaction was stirred for 3 h at 25° C. The reaction was then concentrated in vacuo to remove the ethanol and then acidified to pH=2 with a 1N aqueous hydrochloric acid solution. This solution was then extracted with methylene chloride 3×15 mL). The combined organic layers were dried over sodium sulfate, filtered, and concentrated in vacuo. Flash chromatography (Merck Silica gel 60, 230-400 mesh, hexanes to 60/40 hexanes/ethyl acetate plus 1% acetic acid) afforded 2-(4-methanesulfonyl-phenyl)-3-(tetrahydro-pyran-2-yl)-propionic acid (60 mg, 85%) as a white solid: FAB-HRMS m/e calcd for $C_{15}H_{20}O_5S$ (M+H)$^+$ 313.1109. found 313.1111.

A solution of 2-(4-methanesulfonyl-phenyl)-3-(tetrahydro-pyran-2-yl)-propionic acid (60 mg, 0.19 mmol), benzotriazol-1-yloxy-tris(dimethylamino)phosphonium hexafluoro-phosphate (127 mg, 0.29 mmol), and 2-aminothiazole (28 mg, 0.29 mmol) in methylene chloride (5 mL) at 25° C. was treated with triethylamine (0.08 mL, 0.58 mmol). The resulting reaction mixture was stirred at 25° C. for 16 h. The reaction mixture was then diluted with water (10 mL) and extracted with methylene chloride 3×15 mL).

The combined organic layers were sequentially washed with water (1×10 mL), a 1N aqueous sodium hydroxide solution (1×10 mL), a 1N aqueous hydrochloric acid solution (1×10 mL), and a saturated sodium chloride solution (1×10 mL). The organic layer was dried over sodium sulfate, filtered, and concentrated in vacuo. Biotage chromatography (FLASH 12M, Silica, 20/80 hexanes/ethyl acetate) afforded 2-(4-methanesulfonyl-phenyl)-3-(tetrahydro-pyran-2-yl)-N-thiazol-2-yl-propionamide (54 mg, 71%) as a colorless oil: EI-HRMS m/e calcd for $C_{18}H_{22}N_2O_4S_2$ (M+) 394.1021. found 394.1021.

EXAMPLE 12

2-(4-Methylsulfonyl-3-trifluoromethyl-phenyl)-3-(tetrahydro-pyran-2-yl)-N-thiazole-2-yl-propionamide

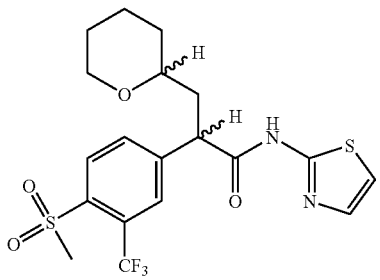

A solution of (tetrahydro-pyran-2-yl)-methanol (3.40 g, 29.26 mmol) in dry methylene chloride (140 mL) and 2,6-lutidine (5.23 mL, 45.02 mmol) was cooled to −78° C. under argon and then treated with trifluoromethanesulfonic anhydride (5.78 mL, 35.11 mmol). The reaction mixture was stirred at −78° C. for 1 h and then diluted with hexanes (200 mL). The mixture was then washed with a 50% aqueous sodium bicarbonate solution (150 mL), dried over magnesium sulfate, and concentrated in vacuo to afford trifluoromethanesulfonic acid tetrahydro-pyran-2-yl methyl ester as a crude oil which was used without further purification.

A solution of diisopropylamine (7.04 mL, 49.97 mmol) in dry tetrahydrofuran (140 mL) cooled to −78° C. under argon was treated with a 2.5M solution of n-butyllithium in hexanes (19.8 mL, 49.5 mmol). The reaction mixture was stirred at −78° C. for 30 min and then treated dropwise with a solution of (4-fluoro-3-trifluoromethyl-phenyl)-acetic acid (5.00 g, 22.51 mmol) in dry tetrahydrofuran (25 mL) and 1,3-dimethyl-3,4,5,6-tetrahydro-2(1H)-pyrimidinone (8.5 mL). The reaction mixture turned gold in color and was allowed to stir at −78° C. for 1 h. At this time, the reaction was treated with a solution of trifluoromethanesulfonic acid tetrahydro-pyran-2-yl methyl ester (7.26 g, 29.26 mmol) in dry tetrahydrofuran (100 mL). The reaction mixture was allowed to warm to 25° C., where it was stirred for 30 min. The reaction mixture then was quenched with a saturated aqueous ammonium chloride solution (100 mL) and then concentrated in vacuo to remove tetrahydrofuran. The aqueous residue was acidified to pH=2 using a 1N aqueous hydrochloric acid solution. The resulting aqueous layer was extracted with ethyl acetate (2×250 mL). The combined organic extracts were dried over sodium sulfate, filtered, and concentrated in vacuo. Flash chromatography (Merck Silica gel 60, 230-400 mesh, 3/7 hexanes/ethyl acetate to 1/1 hexanes/ethyl acetate) afforded 2-(4-fluoro-3-trifluoromethyl-phenyl)-3-(tetrahydro-pyran-2-yl)-propionic acid (5.20 g, 72%) as a yellow gum: EI-HRMS m/e calcd for $C_{15}H_{16}F_4O_3$ (M+Na)+ 343.0931. found 343.0928.

A solution of 2-(4-fluoro-3-trifluoromethyl-phenyl)-3-(tetrahydro-pyran-2-yl)-propionic acid (5.20 g, 16.24 mmol) in dry N,N-dimethylformamide (90 mL) at 25° C. under argon was carefully treated with 95% sodium hydride (410 mg, 17.05 mmol). The reaction mixture was stirred at 25° C. for 30 min and then was treated with sodium thiomethoxide (2.40 g, 32.48 mmol). This mixture was heated at 100° C. for 4.5 h and then concentrated in vacuo to remove N,N-dimethylformamide. The residue was diluted with water (100 mL) and then was acidified to pH=2 using a 1N aqueous hydrochloric acid solution. The resulting aqueous layer was extracted with ethyl acetate (2×600 mL). The combined organic extracts were dried over sodium sulfate, filtered, and concentrated in vacuo. Flash chromatography (Merck Silica gel 60, 230-400 mesh, 98/2 chloroform/methanol to 9/1 chloroform/methanol) afforded 2-(4-methylsulfanyl-3-trifluoromethyl-phenyl)-3-(tetrahydro-pyran-2-yl)-propionic acid (5.70 g, 100%) as a yellow gum: EI-HRMS m/e calcd for $C_{16}H_{19}F_3O_3S$ (M+Na)+ 371.0899. found 371.0902.

A solution of 2-(4-methylsulfanyl-3-trifluoromethyl-phenyl)-3-(tetrahydro-pyran-2-yl)-propionic acid (348 mg, 1.0 mmol) in formic acid (1.20 mL, 30 mmol) and tetrahydrofuran (1.0 mL) cooled to 0° C. was treated with a 30% aqueous hydrogen peroxide solution (1.34 mL, 10 mmol). The resulting solution was allowed to warm to 25° C., where it was stirred for 24 h. The reaction was then re-cooled to 0° C., quenched with a saturated aqueous sodium bisulfite solution, and then extracted with ethyl acetate (2×50 mL). The combined organic layers were dried over sodium sulfate, filtered, and concentrated in vacuo to afford 2-(4-methylsulfonyl-3-trifluoromethyl-phenyl)-3-(tetrahydro-pyran-2-yl)-propionic acid (378 mg, 100%) as a colorless gum: EI-HRMS m/e calcd for $C_{16}H_{19}F_3O_5S$ (M+Na)+ 403.0797. found 403.0803.

A solution of 2-(4-methylsulfonyl-3-trifluoromethyl-phenyl)-3-(tetrahydro-pyran-2-yl)-propionic acid (50 mg, 0.13 mmol) in methylene chloride (1 mL) was treated with N,N-dimethylformamide (3 drops) and then cooled to 0° C. The reaction mixture was then treated with a 2.0M solution of oxalyl chloride in methylene chloride (0.08 mL, 0.156 mmol). The reaction mixture was stirred at 0° C. for 30 min, allowed to warm to 25° C., and then concentrated in vacuo to remove solvents and excess oxalyl chloride. The resulting residue was re-dissolved in dry tetrahydrofuran (1 mL) and was treated dropwise with a solution of 2-aminothiazole (28 mg, 0.27 mmol) in tetrahydrofuran (1 mL) and 2,6-lutidine (0.08 mL, 0.65 mmol). The resulting reaction mixture was stirred at 25° C. for 16 h. The reaction mixture was then diluted with water (50 mL) and extracted with methylene chloride 3×50 mL). The combined organic layers were dried over sodium sulfate, filtered, and concentrated in vacuo. Biotage chromatography (FLASH 12M, Silica, 7/3 hexanes/ethyl acetate to 6/4 hexanes/ethyl acetate to 1/1 hexanes/ethyl acetate) afforded 2-(4-methylsulfonyl-3-trifluoromethyl-phenyl)-3-(tetrahydro-pyran-2-yl)-N-thiazole-2-yl-propionainide (37 mg, 61%) as a white foam: EI-HRMS m/e calcd for $C_{19}H_{21}F_3N_2O_4S_2$ (M+H)+ 463.0968. found 463.0974.

EXAMPLE 13

2(R)-(3-Chloro-4-methanesulfonyl-phenyl)-N-(5-chloro-pyrazin-2-yl)-3-(4-hydroxy-cyclohexyl)-propionamide

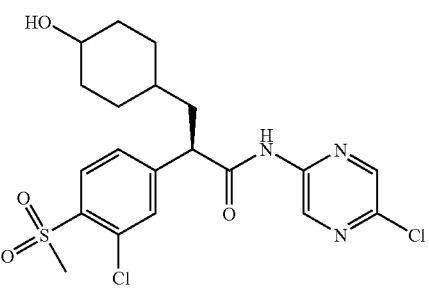

A solution of 2(R)-(3-chloro-4-methanesulfonyl-phenyl)-N-(5-chloro-pyrazin-2-yl)-3-(4-oxo-cyclohexyl)-propionamide (prepared as in Example 61, 30.0 mg, 0.064 mmol) in methanol (0.5 mL) was treated with sodium borohydride (6.03 mg, 0.16 mmol). The reaction mixture was stirred at 25° C. for 5 min. The reaction was then diluted with ethyl acetate (5 mL) and quenched by the dropwise addition of water. The reaction was then diluted with more water (5 mL) and concentrated in vacuo to remove methanol. The resulting slurry was extracted with ethyl acetate 3×5 mL), and the combined organic extracts were dried over magnesium sulfate, filtered, and concentrated in vacuo. Biotage chromatography (FLASH 12S, Silica, 3/7 hexanes/ethyl acetate) afforded 2(R)-(3-chloro-4-methanesulfonyl-phenyl)-N-(5-chloro-pyrazin-2-yl)-3-(4-hydroxy-cyclohexyl)-propionamide (29.0 mg, 96.3%) as a light yellow foam: EI-HRMS m/e calcd for $C_{20}H_{23}Cl_2N_3O_4S$ $(M+H)^+$ 472.0859. found 472.0866.

EXAMPLE 14

2-(4-Methanesulfonyl-3-trifluoromethyl-phenyl)-N-pyrazin-2-yl-3-(tetrahydro-pyran-2-yl)-propionamide

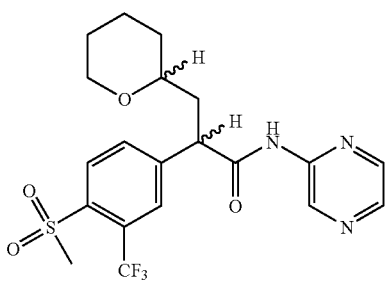

A solution of 2-(4-methylsulfonyl-3-trifluoromethyl-phenyl)-3-(tetrahydro-pyran-2-yl)-propionic acid (prepared as in Example 12, 50 mg, 0.13 mmol) in methylene chloride (1 mL) was treated with N,N-dimethylformamide (3 drops) and then cooled to 0° C. The reaction mixture was then treated with a 2.0M solution of oxalyl chloride in methylene chloride (0.08 mL, 0.156 mmol). The reaction mixture was stirred at 0° C. for 30 min, allowed to warm to 25° C., and then concentrated in vacuo to remove solvents and excess oxalyl chloride. The resulting residue was re-dissolved in dry tetrahydrofuran (1 mL) and was treated dropwise with a solution of 2-aminopyrazine (15 mg, 0156 mmol) in tetrahydrofuran (1 mL) and 2,6-lutidine (0.02 mL, 0.157 mmol). The resulting reaction mixture was stirred at 25° C. for 16 h. The reaction mixture was then diluted with water (50 mL) and extracted with methylene chloride 3×50 mL). The combined organic layers were dried over sodium sulfate, filtered, and concentrated in vacuo. Biotage chromatography (FLASH 12M, Silica, 7/3 hexanes/ethyl acetate to 1/1 hexanes/ethyl acetate) afforded 2-(4-methanesulfonyl-3-trifluoromethyl-phenyl)-N-pyrazin-2-yl-3-(tetrahydro-pyran-2-yl)-propionamide (13 mg, 22%) as a colorless gum: EI-HRMS m/e calcd for $C_{20}H_{22}F_3N_3O_4S$ $(M+Na)^+$ 480.1175. found 480.1177.

EXAMPLE 15

6-[2-(4-Methylsulfonyl-3-trifluoromethyl-phenyl)-3-(tetrahydro-pyran-2-yl)-propionylamino]-nicotinic acid methyl ester

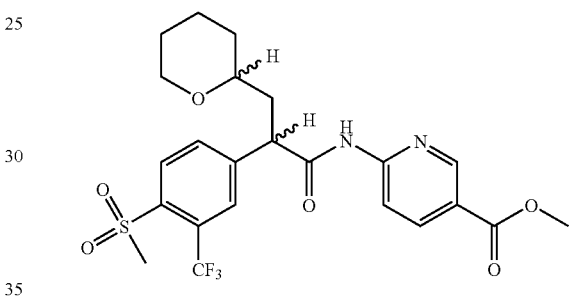

A mixture of 6-aminonicotinic acid (4.0 g, 28.9 mmol), methanol (75 mL), and concentrated hydrochloric acid (4 mL) was heated under reflux for 16 h. The reaction mixture was allowed to cool to 25° C. and then concentrated in vacuo to remove methanol. The resulting solid was treated with water (20 mL) and enough sodium bicarbonate to adjust the pH to pH=8. The solution was then extracted with ethyl acetate 3×25 mL). The combined organic layers were dried over sodium sulfate, filtered, and concentrated in vacuo to afford 6-aminonicotinic acid methyl ester (3.12 g, 71%) as white foam: EI-HRMS m/e calcd for $C_7H_8N_2O_2$ $(M^+)$ 152.0586. found 152.0586.

A solution of 2-(4-methylsulfonyl-3-trifluoromethyl-phenyl)-3-(tetrahydro-pyran-2-yl)-propionic acid (prepared as in Example 12, 300 mg, 0.79 mmol) in methylene chloride (6 mL) was treated with N,N-dimethylformamide (7 drops) and then cooled to 0° C. The reaction mixture was then treated with a 2.0M solution of oxalyl chloride in methylene chloride (0.48 mL, 0.95 mmol). The reaction mixture was stirred at 0° C. for 30 min, allowed to warm to 25° C., and then concentrated in vacuo to remove solvents and excess oxalyl chloride. The resulting residue was re-dissolved in dry tetrahydrofuran (6 mL) and was treated dropwise with a solution of 6-aminonicotinic acid methyl ester (252 mg, 1.67 mmol) in tetrahydrofuran (5 mL) and 2,6-lutidine (0.48 mL, 3.95 mmol). The resulting reaction mixture was stirred at 25° C. for 16 h. The reaction mixture was then diluted with water (100 mL) and extracted with methylene chloride 3×50 mL). The combined organic layers were dried over sodium sulfate, filtered, and concentrated in vacuo. Biotage chromatography (FLASH 40S, Silica, 7/3 hexanes/ethyl acetate

EXAMPLE 16

6-[2-(4-Methylsulfonyl-3-trifluoromethyl-phenyl)-3-(tetrahydro-pyran-2-yl)-propionylamino]-nicotinic acid

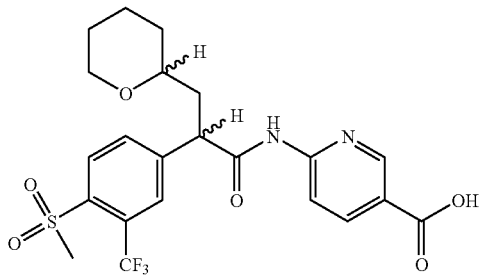

A solution of 6-[2-(4-methylsulfonyl-3-trifluoromethyl-phenyl)-3-(tetrahydro-pyran-2-yl)-propionylamino]-nicotinic acid methyl ester (prepared as in Example 15, 21 mg, 0.04 mmol) in methanol (0.40 mL) was treated with a 1N aqueous sodium hydroxide solution (0.20 mL, 0.20 mmol). The reaction mixture was stirred at 25° C. for 1 h. The reaction mixture was then diluted with water and concentrated in vacuo to remove methanol. The resulting aqueous residue was acidified to pH=2 with a 1N aqueous hydrochloric acid solution and then extracted with ethyl acetate (2×10 mL). The combined organic layers were dried over sodium sulfate, filtered, and concentrated in vacuo to afford pure 6-[2-(4-methylsulfonyl-3-trifluoromethyl-phenyl)-3-(tetrahydro-pyran-2-yl)-propionylamino]-nicotinic acid (15 mg, 75%) as a colorless gum: EI-HRMS m/e calcd for $C_{22}H_{23}F_3O_6S$ $(M+H)^+$ 501.1302. found 501.1305.

EXAMPLE 17

N-(5-Hydroxymethyl-pyridin-2-yl)-2-(4-methylsulfonyl-3-trifluoromethyl-phenyl)-3-(tetrahydro-pyran-2-yl)-propionamide

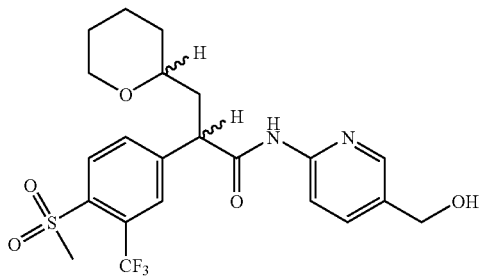

A solution of 6-[2-(4-methylsulfonyl-3-trifluoromethyl-phenyl)-3-(tetrahydro-pyran-2-yl)-propionylamino]-nicotinic acid methyl ester (prepared as in Example 15, 129 mg, 0.25 mmol) in ethyl ether (6 mL) cooled to 0° C. was treated with a 1.0M solution of lithium aluminum hydride solution in diethyl ether (0.30 mL, 0.30 mmol). The orange-colored reaction mixture was stirred at 0° C. for 1 h. The reaction was then quenched by the dropwise addition of water (10 mL) and extracted with ethyl acetate (2×10 mL). The combined organic extracts were dried over sodium sulfate, filtered, and concentrated in vacuo. Biotage chromatography (FLASH 40S Silica, 8/2 hexanes/ethyl acetate) afforded N-(5-hydroxymethyl-pyridin-2-yl)-2-(4-methanesulfonyl-3-trifluoromethyl-phenyl)-3-(tetrahydro-pyran-2-yl)-propionamide (44 mg, 36%) as a cream foam: EI-HRMS m/e calcd for $C_{22}H_{25}F_3N_2O_5S$ $(M+H)^+$ 487.1509. found 487.1514.

EXAMPLE 18

2-(3-Chloro-4-methanesulfonyl-phenyl)-N-pyrazin-2-yl-3-(tetrahydro-thiopyran-3(R)-yl)-propionamide

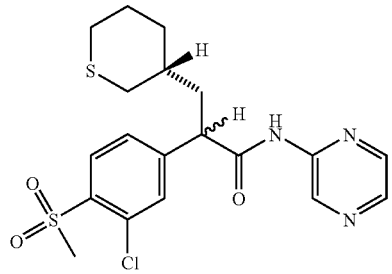

A slurry of (3-chloro-4-methylsulfanyl-phenyl)-acetic acid methyl ester (prepared as in Example 4, 1.00 g, 4.33 mmol) in formic acid (6.54 mL, 92.30 mmol) was cooled to 0° C. and then was treated with a 30% aqueous hydrogen peroxide solution (1.47 mL, 13.85 mmol). The resulting solution was allowed to warm to 25° C., where it was stirred for 15 h. The reaction was cooled in an ice bath, and the product was precipitated by the addition of water (100 mL). The solid was filtered off, washed with water, and dried by suction to afford pure (3-chloro-4-methanesulfonyl-phenyl)-acetic acid methyl ester (1.11 g, 97.5%) as a white solid: mp 54-57° C.; EI-HRMS m/e calcd for $C_{10}H_{11}ClO_4S$ $(M^+)$ 262.0066. found 262.0060.

A solution of dimethyl 3,3'-thiodipropionate (30.00 g, 144.0 mmol) in ethylene glycol dimethyl ether (200 mL), under nitrogen, was treated with sodium hydride (7.00 g, 145.8 mmol), and the reaction was heated under reflux for 1.5 h. The reaction mixture was then cooled to 25° C. and was slowly treated with a saturated aqueous sodium bicarbonate solution. The solvent was then removed in vacuo, and the resulting residue was diluted with water (500 mL) and extracted with ethyl acetate 3×300 mL). The combined organic extracts were then washed with a saturated aqueous sodium bicarbonate solution (1×150 mL) followed by a saturated aqueous sodium chloride solution (1×150 mL). The organic layer was dried over magnesium sulfate, filtered, and concentrated in vacuo. Biotage chromatography, performed in two batches, (FLASH 40M, Silica, 9/1 hexanes/diethyl ether) afforded 4-hydroxy-5,6-dihydro-2H-thiopyran-3-carboxylic acid methyl ester (12.89 g, 51.4%) as a colorless oil.

A suspension of baker's yeast (Saf-Instant yeast, 30 g) in water (700 mL) was treated with sucrose (142 g). The mixture was stirred at 25° C. for 6 h. At this time, 4-hydroxy- 5,6-dihydro-2H-thiopyran-3-carboxylic acid methyl ester (4.06 g, 23.31 mmol) was added. The resulting slurry was stirred at 25° C. for 22 h and then was filtered through a pad of celite. The filtrate was extracted with ethyl acetate (5×300 mL). The combined organic extracts were washed with a saturated aqueous sodium chloride solution (1×150 mL), dried over magnesium sulfate, filtered, and concentrated in vacuo. Biotage chromatography (FLASH 40M, Silica, 3/1 hexanes/ethyl acetate) afforded 4(S)-hydroxy-tetrahydro-thiopyran-3(R)-carboxylic acid methyl ester (4.08 g, 99.3%) as a colorless oil: $[\alpha]^{23}_{589}$=+37.76° (c=2.9, methanol)

A solution of 4(S)-hydroxy-tetrahydro-thiopyran-3(R)-carboxylic acid methyl ester (1.00 g, 5.674 mmol) in dry tetrahydrofuran (50 mL), under argon, was treated with 1,1'-thiocarbonyldiimidazole (2.085 g, 11.35 mmol) and pyridine (6.88 µL, 8.511 mmol). The reaction mixture was stirred at 25° C. for 36 h and was then diluted with ethyl acetate (100 mL). The resulting solution was washed sequentially with a saturated aqueous sodium bicarbonate solution (1×50 mL) and a saturated aqueous sodium chloride solution (1×50 mL). The combined organic extracts were dried over magnesium sulfate, filtered, and concentrated in vacuo. Biotage chromatography (FLASH 40M, Silica, 4/1 hexanes/ethyl acetate) afforded 4(S)-(imidazole-1-carbothioyloxy)-tetrahydro-thiopyran-3(R)-carboxylic acid methyl ester (901 mg, 55.4%) as a beige oil: EI-HRMS m/e calcd for $C_{11}H_{14}N_2O_3S_2$ (M+) 286.0446. found 286.0438.

A solution of tributyltin hydride (1.702 mL, 6.292 mmol) in dioxane (82.59 mL) was treated with 2,2'-azobisisobutyronitrile (110.7 mg, 0.661 mmol). The resulting mixture was heated under reflux for 2 h. The reaction was then treated with a solution of 4(S)-(imidazole-1-carbothioyloxy)-tetrahydro-thiopyran-3(R)-carboxylic acid methyl ester (901 mg, 3.146 mmol) in dioxane (3 mL). The reaction was heated under reflux for an additional 30 min and then was cooled in an ice bath. The solvent was removed in vacuo. The resulting residue was suspended in acetonitrile (100 mL) and was washed with hexanes 3×30 mL). The resulting solution was concentrated in vacuo, dissolved in dry tetrahydrofuran (18.07 mL) under argon, cooled in an ice bath, and then treated with a 1.0M solution of lithium aluminum hydride in tetrahydrofuran (3.159 mL, 3.159 mmol). The reaction was stirred at 0° C. for 20 min and was then quenched by the addition of ethyl acetate (30 mL). The reaction mixture was then treated with a saturated aqueous ammonium chloride solution, and the layers were separated. The aqueous layer was then washed with ethyl acetate (2×25 mL), and the combined organic extracts were washed with a saturated aqueous sodium chloride solution, dried over magnesium sulfate, filtered, and concentrated in vacuo. Biotage chromatography (FLASH 12M, Silica, 7/3 hexanes/ethyl acetate) afforded (R)-(tetrahydro-thiopyran-3-yl)-methanol (291 mg, 69.7%) as a colorless oil: $[\alpha]^{23}_{589}$=−4.87° (c=0.78, methanol); EI-HRMS m/e calcd for $C_6H_{12}OS$ (M+) 132.0609. found 132.0614.

A solution of (R)-(tetrahydro-thiopyran-3-yl)-methanol (180 mg, 1.36 mmol) in methylene chloride (16.82 mL) cooled to −78° C. was treated with 2,6-lutidine (192.8 µL, 1.66 mmol) followed by trifluoromethanesulfonic anhydride (268.0 µL, 1.63 mmol). The reaction was stirred at −78° C. for 10 min and was then diluted with hexanes (20 mL). The mixture was washed with a saturated aqueous sodium bicarbonate solution (1×10 mL). The combined organic extracts were dried over magnesium sulfate, filtered, and concentrated in vacuo. The resulting residue was dissolved in acetone (17 mL) and was treated with sodium iodide (612.3 mg, 4.086 mmol). The reaction mixture was stirred at 25° C. for 10 min and then concentrated in vacuo. The residue was suspended in methylene chloride (25 mL). This mixture was washed with water (1×15 mL), dried over magnesium sulfate, filtered, and concentrated in vacuo. Biotage chromatography (FLASH 12S, Silica, 97/3 hexanes/ethyl acetate) afforded 3(R)-iodomethyl-tetrahydro-thiopyran (139 mg, 42.2%) as a light yellow oil which was not characterized but was used immediately for the alkylation reaction.

A 2.0M solution of lithium diisopropylamide in heptane/tetrahydrofuran/ethylbenzene (564.0 [L, 1.128 mmol) and N,N,N',N'-tetramethylethylenediamine (157.0 µL, 1.040 mmol) in dry tetrahydrofuran (3 mL) cooled to −78° C. under nitrogen was treated with (3-chloro-4-methanesulfonyl-phenyl)-acetic acid methyl ester (269.4 mg, 1.02 mmol). The reaction mixture was stirred at −78° C. for 1 h and then warmed to 0° C. The reaction was then treated with a solution of 3(R)-iodomethyl-tetrahydro-thiopyran (71.00 mg, 0.293 mmol) in dry tetrahydrofuran (1 mL) and allowed to warm to 25° C., where it was stirred for 19 h. The reaction mixture was then quenched with a saturated aqueous ammonium chloride solution (10 mL) and then concentrated in vacuo to remove tetrahydrofuran. The aqueous residue was extracted with ethyl acetate (2×20 mL), and the combined organic extracts were dried over magnesium sulfate, filtered, and concentrated in vacuo. Biotage chromatography (FLASH 12M, Silica, 4/1 hexanes/ethyl acetate) afforded 2-(3-chloro-4-methanesulfonyl-phenyl)-3(R)-(tetrahydro-thiopyran-3-yl)-propionic acid methyl ester (96 mg, 86.9%) as a colorless oil: $[\alpha]^{23}_{589}$=+10.93° (c=0.76, methanol); EI-HRMS m/e calcd for $C_{16}H_{21}ClO_4S_2$ (M+) 376.0570. found 376.0574.

A solution of 2-(3-chloro-4-methanesulfonyl-phenyl)-3(R)-(tetrahydro-thiopyran-3-yl)-propionic acid methyl ester (247 mg, 0.655 mmol) in methanol (4.75 mL) was treated with a 0.8M aqueous lithium hydroxide solution (7.27 mL, 5.895 mmol). The reaction mixture was stirred at 25° C. for 1.5 h and then concentrated in vacuo to remove methanol. The remaining aqueous layer was acidified to pH=2 with a 10% aqueous hydrochloric acid solution and then extracted with ethyl acetate (2×100 mL). The combined organic layers were washed with a saturated aqueous sodium chloride solution (1×100 mL), dried over sodium sulfate, filtered, and concentrated in vacuo to afford pure 2-(3-chloro-4-methanesulfonyl-phenyl)-3(R)-(tetrahydro-thiopyran-3-yl)-propionic acid (227.0 mg, 95.5%) as a light yellow foam: $[\alpha]^{23}_{539}$=+12.21° (c=0.79, methanol).

A solution of 2-(3-chloro-4-methanesulfonyl-phenyl)-3(R)-(tetrahydro-thiopyran-3-yl)-propionic acid (52 mg, 0.143 mmol) in methylene chloride (1 mL) was treated with N,N-dimethylformamide (0.1 mL) and then cooled to 0° C. The reaction mixture was treated with a 2.0M solution of oxalyl chloride in methylene chloride (143 µL, 0.286 mmol). The reaction mixture was stirred at 0° C. for 30 min, allowed to warm to 25° C., and then concentrated in vacuo to remove solvents and excess oxalyl chloride. The resulting residue was re-dissolved in dry tetrahydrofuran (1 mL) and was treated dropwise with a solution of 2-aminopyrazine (27.2 mg, 0.286 mmol) in tetrahydrofuran (1 mL) and pyridine (57.8 µL, 0.715 mmol). The resulting reaction mixture was stirred at 25° C. for 30 min. The reaction mixture was then diluted with water (2 mL) and extracted with methylene chloride 3×5 mL). The combined organic layers were dried over sodium sulfate, filtered, and concentrated in vacuo. Biotage chromatography (FLASH 12M, Silica, 1/1 hexanes/ethyl acetate) afforded 2-(3-chloro-4-methanesulfonyl-phenyl)-N-pyrazin-2-yl-3 (R)-(tetrahydro-thiopyran-3-yl)-propionamide (44 mg, 69.8%) as a colorless gum: EI-HRMS m/e calcd for $C_{19}H_{22}ClN_3O_3S_2$ (M+H)$^+$ 440.0864. found 440.0867.

EXAMPLE 19

2-(3-Chloro-4-methanesulfonyl-phenyl)-3-(1-oxo-hexahydro-1λ$^4$-thiopyran-3(R)-yl)-N-pyrazin-2-yl-propionamide

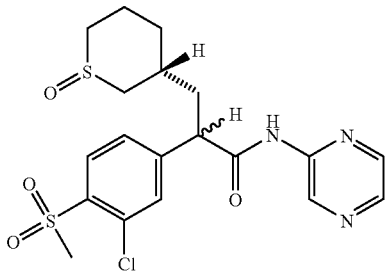

A slurry of 2-(3-chloro-4-methanesulfonyl-phenyl)-N-pyrazin-2-yl-3-(tetrahydro-thiopyran-3(R)-yl)-propionamide (prepared as in Example 18, 10.0 mg, 0.0227 mmol) in formic acid (68.5 μL, 1.816 mmol) cooled to 0° C. was treated with a 30% aqueous hydrogen peroxide solution (7.7 μL, 0.068). The resulting solution was stirred at 0° C. for 10 min. The reaction was quenched by the addition of a 10% aqueous sodium sulfite solution (1 mL) and then extracted with ethyl acetate (2×5 mL). The organics were dried over magnesium sulfate, filtered, and concentrated in vacuo. Biotage chromatography (FLASH 12S, Silica, 93/7 chloroform/methanol) afforded 2-(3-chloro-4-methanesulfonyl-phenyl)-3-(1-oxo-hexahydro-1λ$^4$-thiopyran-3(R)-yl)-N-pyrazin-2-yl-propionamide (10.0 mg, 96.5%) as a beige gum: EI-HRMS m/e calcd for $C_{19}H_{22}ClN_3O_4S_2$ (M+Na)$^+$ 478.0632. found 478.0632.

EXAMPLE 20

2-(3-Chloro-4-methanesulfonyl-phenyl)-N-pyrazin-2-yl-3-(tetrahydro-pyran-4-yl)-propionamide

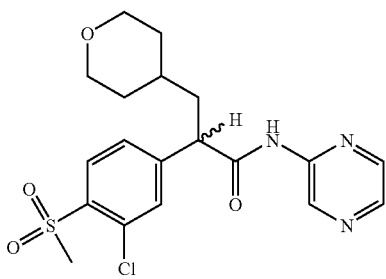

A solution of (tetrahydro-pyran-4-yl)-methanol (1.0 g, 8.61 mmol, prepared according to WO 99/00385) in methylene chloride (30 mL) at 25° C. was treated with 4-(dimethylamino)pyridine (1.17 g, 9.47 mmol) and p-toluenesulfonyl chloride (1.64 g, 8.61 mmol) and then was allowed to stir at 25° C. overnight. The reaction was then transferred to a separatory funnel and washed with a 1N aqueous hydrochloric acid solution (10 mL), a saturated aqueous sodium bicarbonate solution (10 mL), and a saturated aqueous sodium chloride solution (10 mL), dried over sodium sulfate, filtered, and concentrated in vacuo. Biotage chromatography (FLASH 40S, Silica, 75/25 hexanes/ethyl acetate) afforded toluene-4-sulfonic acid tetrahydro-pyran-4-yl methyl ester (1.77 g, 76%) as a colorless oil.

A solution of toluene-4-sulfonic acid tetrahydro-pyran-4-yl methyl ester (1.77 g, 6.55 mmol) and sodium iodide (2.85 g, 18.99 mmol) in acetone (26 mL) was heated to 60° C. for 16 h. The resulting suspension was then cooled to 10° C. and filtered. The salts were rinsed with cold acetone (5 mL), and the filtrate and washings were concentrated in vacuo to a thick slurry. This slurry was treated with methylene chloride (10 mL). The resulting precipitate was removed by filtration and was washed with methylene chloride (10 mL). The filtrate and washings were then dried over magnesium sulfate, filtered through a pad of silica gel, and then concentrated in vacuo to afford 4-iodomethyl-tetrahydro-pyran as a light yellow oil.

A solution of diisopropylamine (0.33 mL, 2.38 mmol) in tetrahydrofuran (6 mL) cooled to −78° C. under an argon atmosphere was treated with a 2.5M solution of n-butyl-lithium in hexanes (0.95 mL, 2.38 mmol). The reaction mixture was stirred at −78° C. for 15 min, after which time, a solution of (3-chloro-4-methylsulfanyl-phenyl)-acetic acid methyl ester (prepared as in Example 4, 500 mg, 2.17 mmol) in tetrahydrofuran (1 mL) and 1,3-dimethyl-3,4,5,6-tetrahydro-2(1H)-pyrimidinone (0.5 mL) was slowly added via a cannula. The greenish yellow solution was allowed to stir at −78° C. for 1 h, after which time, a solution of 4-iodomethyl-tetrahydro-pyran (588 mg, 2.60 mmol) in 1,3-dimethyl-3,4,5,6-tetrahydro-2(1H)-pyrimidinone (0.5 mL) was added via a cannula. The reaction mixture was then allowed to warm to 25° C., where it was stirred for 16 h. The reaction mixture was then quenched by the addition of a saturated aqueous ammonium chloride solution (30 mL). This solution was extracted with ethyl acetate 3×20 mL). The combined organic layers were washed with a 10% aqueous sulfuric acid solution (2×50 mL) and a saturated aqueous sodium bicarbonate solution (2×50 mL), dried over sodium sulfate, filtered, and concentrated in vacuo. Biotage chromatography (FLASH 40S, Silica, 75/25 hexanes/ethyl acetate) afforded 2-(3-chloro-4-methylsulfanyl-phenyl)-3-(tetrahydro-pyran-4-yl)-propionic acid methyl ester (431 mg, 61%) as a yellow oil: EI-HRMS m/e calcd for $C_{16}H_{21}ClO_3S$ (M$^+$) 328.0900. found 328.0898.

A solution of 2-(3-chloro-4-methylsulfanyl-phenyl)-3-(tetrahydro-pyran-4-yl)-propionic acid methyl ester (200 mg, 0.61 mmol) in formic acid (0.23 mL) and tetrahydrofuran (0.5 mL) cooled to 0° C. was treated with a 30% aqueous hydrogen peroxide solution (0.35 mL, 3.04 mmol). The reaction was slowly warmed to 25° C. where it was stirred for 16 h. The reaction mixture was then cooled to 0° C., quenched with a saturated aqueous sodium sulfite solution, and then extracted with ethyl acetate 3×20 mL). The organics were dried over sodium sulfate, filtered, and concentrated in vacuo. Biotage chromatography (FLASH 12M, Silica, 60/40 hexanes/ethyl acetate) afforded 2-(3-chloro-4-methanesulfonyl-phenyl)-3-(tetrahydro-pyran-4-yl)-propionic acid methyl ester (190 mg, 87%) as a colorless oil: (ES)$^+$-HRMS m/e calcd for $C_{16}H_{21}ClO_5S$ (M+Na)$^+$ 383.0690. found 383.0692.

A solution of 2-(3-chloro-4-methanesulfonyl-phenyl)-3-(tetrahydro-pyran-4-yl)-propionic acid methyl ester (190 mg, 0.53 mmol) in ethanol (10 mL) was treated with a solution of potassium hydroxide (174 mg, 2.64 mmol) in water (4 mL). The reaction was stirred at 25° C. for 2.5 h.

The reaction was then concentrated in vacuo to remove the ethanol and then acidified to pH=2 with a 1N aqueous hydrochloric acid solution. The resulting solution was then extracted with methylene chloride 3×10 mL). The combined organic layers were dried over sodium sulfate, filtered, and concentrated in vacuo to afford 2-(3-chloro-4-methanesulfonyl-phenyl)-3-(tetrahydro-pyran-4-yl)-propionic acid (167 mg, 92%) as a white foam: (ES)$^+$-HRMS m/e calcd for $C_{15}H_{19}ClO_5S$ (M+Na)$^+$ 369.0534. found 369.0536.

A solution of 2-(3-chloro-4-methanesulfonyl-phenyl)-3-(tetrahydro-pyran-4-yl)-propionic acid (165 mg, 0.48 mmol) in methylene chloride (12 mL) and N,N-dimethylformamide (1 drop) cooled to 0° C. was treated dropwise with a 2.0M solution of oxalyl chloride in methylene chloride (0.27 mL, 0.55 mmol). The reaction was stirred at 0° C. for 30 min. At this time, the reaction was concentrated in vacuo to yield a light yellow oil. This oil was dissolved in tetrahydrofuran (5 mL) and then treated with a solution of 2-aminopyrazine (91 mg, 0.95 mmol) dissolved in tetrahydrofuran (10 mL) and pyridine (0.19 mL, 2.4 mmol). The reaction was then stirred at 25° C. for 16 h. At this time, the reaction was diluted with water (15 mL) and extracted with methylene chloride 3×25 mL). The combined organic layers were dried over sodium sulfate, filtered, and concentrated in vacuo. Biotage chromatography (FLASH 12M, Silica, 25/75 hexanes/ethyl acetate) afforded 2-(3-chloro-4-methanesulfonyl-phenyl)-N-pyrazin-2-yl-3-(tetrahydro-pyran-4-yl)-propionamide (100 mg, 50%) as a white foam: (ES)$^+$-HRMS m/e calcd for $C_{19}H_{22}ClN_3O_4S$ (M+H)$^+$ 424.1093. found 424.1095.

EXAMPLE 21

N-(5-Bromo-pyrazin-2-yl)-2-(3-chloro-4-methanesulfonyl-phenyl)-3-(tetrahydro-pyran-4-yl)-propionamide

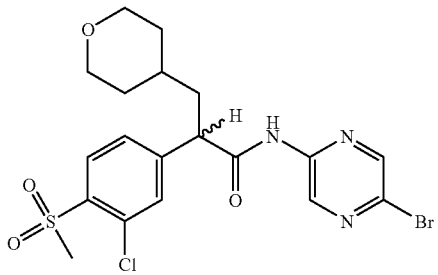

A solution of 2-(3-chloro-4-methanesulfonyl-phenyl)-3-(tetrahydro-pyran-4-yl)-propionic acid (prepared as in Example 20, 470 mg, 1.36 mmol) in methylene chloride (25 mL) and N,N-dimethylformamide (1 drop) cooled to 0° C. was treated with a 2.0M solution of oxalyl chloride in methylene chloride (0.78 mL, 1.56 mmol) and then was stirred at 0° C. for 30 min. At this time, the reaction was concentrated in vacuo to yield a light yellow oil. This oil was dissolved in tetrahydrofuran (10 mL) and then treated with a solution of 2-amino-5-bromopyrazine (472 mg, 2.71 mmol, prepared according to *Tetrahedron* 1988, 44, 2977-2983) in tetrahydrofliran (20 mL) and pyridine (0.55 mL, 6.78 mmol). The reaction was then stirred at 25° C. for 16 h. At this time, the reaction was diluted with water (15 mL) and extracted with methylene chloride 3×25 mL). The organics were dried over sodium sulfate, filtered, and concentrated in vacuo. Biotage chromatography (FLASH 40S, Silica, 40/60 hexanes/ethyl acetate) afforded N-(5-bromo-pyrazin-2-yl)-2-(3-chloro-4-methanesulfonyl-phenyl)-3-(tetrahydro-pyran-4-yl)-propionamide (477 mg, 70%) as a yellow foam: (ES)$^+$-HRMS m/e calcd for $C_{19}H_{21}ClBrN_3O_4S$ (M+H)$^+$ 502.0198. found 502.0205.

EXAMPLE 22

2-(3-Chloro-4-methanesulfonyl-phenyl)-N-(5-cyano-pyrazin-2-yl)-3-(tetrahydro-pyran-4-yl)-propionamide

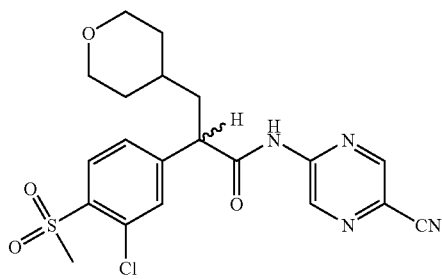

A solution of N-(5-bromo-pyrazin-2-yl)-2-(3-chloro-4-methanesulfonyl-phenyl)-3-(tetrahydro-pyran-4-yl)-propionamide (prepared as in Example 21, 325 mg, 0.65 mmol) in N,N-dimethylformamide (5 mL) at 25° C. was treated with potassium cyanide (105 mg, 1.62 mmol), copper(I) iodide (307 mg, 1.62 mmol), tetrakis(triphenylphosphine)palladium(0) (22 mg, 0.02 mmol), and 18-crown-6 (25 mg, 0.09 mmol). This reaction mixture was then heated to 150° C. under argon for 5 h. At this time, the reaction was cooled to 25° C., concentrated to half the volume, and then chloroform (40 mL) was added until all the salts precipitated out of solution. The salts were removed by filtration through a pad of celite and washed with chloroform. The filtrate was then concentrated in vacuo. Biotage chromatography (FLASH 40S, Silica, 30/70 hexanes/ethyl acetate) afforded 2-(3-chloro-4-methanesulfonyl-phenyl)-N-(5-cyano-pyrazin-2-yl)-3-(tetrahydro-pyran-4-yl)-propionamide (219 mg, 76%) as a white foam: (ES)$^+$-HRMS m/e calcd for $C_{20}H_{21}ClN_4O_4S$ (M+H)$^+$ 449.1045. found 449.1046.

EXAMPLE 23

2-(3-Chloro-4-methanesulfonyl-phenyl)-N-15-(N-hydroxycarbamimidoyl)-pyrazin-2-yl]-3-(tetrahydro-pyran-4-yl)-propionamide

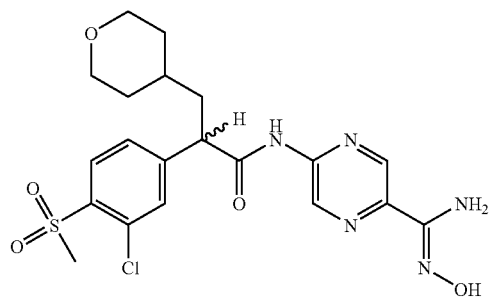

A solution of 2-(3-chloro-4-methanesulfonyl-phenyl)-N-(5-cyano-pyrazin-2-yl)-3-(tetrahydro-pyran-4-yl)-propionamide (prepared as in Example 22, 151 mg, 0.34 mmol) in ethanol (2 mL) and water (1 mL) was treated with hydroxylamine hydrochloride (28 mg, 0.40 mmol) and sodium carbonate (35 mg, 0.34 mmol). The reaction was heated at 70° C. for 3 h. At this time, the reaction was concentrated in vacuo and then extracted with 10% methanol/chloroform 3×30 mL). The organics were dried over magnesium sulfate, filtered, and concentrated in vacuo. Biotage chromatography (FLASH 12M, Silica, 20/80 hexanes/ethyl acetate) afforded 2-(3-chloro-4-methanesulfonyl-phenyl)-N-[5-(N-hydroxy-carbamimidoyl)-pyrazin-2-yl]-3-(tetrahydro-pyran-4-yl)-propionamide (110 mg, 68%) as a white solid: mp 137.2-140.5° C.; (ES)$^+$-HRMS m/e calcd for $C_{20}H_{24}ClN_5O_5S$ (M+H)$^+$ 482.1260. found 482.1263.

EXAMPLE 24

1-[2-(3,4-Dichloro-phenyl)-3-(2-hydroxy-cyclopentyl)-propionyl]-3-methyl-urea

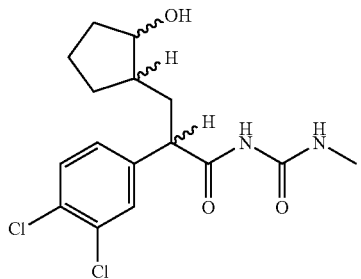

A solution of 2-oxo-cyclopentanecarboxylic acid ethyl ester (10 g, 64.0 mmol) in ethanol (106.7 mL) cooled to 0° C. was treated with 98% sodium borohydride (686 mg, 17.78 mmol). The reaction was stirred at 0° C. for 30 min. At this time, the reaction mixture was poured into water (53 mL) and was extracted into diethyl ether 3×100 mL). The organics were dried over sodium sulfate, filtered, and concentrated in vacuo. Flash chromatography (Merck Silica gel 60, 230-400 mesh, 75/25 ethyl acetate/hexanes) afforded 2-hydroxy-cyclopentanecarboxylic acid ethyl ester (8.5 g, 83.9%) as a clear liquid.

A solution of 2-hydroxy-cyclopentanecarboxylic acid ethyl ester (3.5 g, 22.12 mmol) in methylene chloride (147.5 mL) was treated with 3,4-dihydro-2H-pyran (3.03 mL, 33.1 mmol) and pyridiniump-toluenesulfonate (556 mg, 2.21 mmol). This solution was stirred at 25° C. for 5 h. The reaction was then washed with a half-saturated aqueous sodium chloride solution (2×75 mL), dried over sodium sulfate, filtered, and concentrated in vacuo. Flash chromatography (Merck Silica gel 60, 230-400 mesh, 90/10 hexanes/ethyl acetate) afforded 2-(tetrahydro-pyran-2-yloxy)-cyclopentanecarboxylic acid ethyl ester (4.7 g, 87.7%) as a clear liquid: EI-HRMS m/e calcd for $C_{13}H_{22}O_4$ (M$^+$) 242.1518. found 242.1521.

A slurry of lithium aluminum hydride (883 mg, 23.27 mmol) in tetrahydrofuran (19.4 mL) cooled to 0° C. was treated with 2-(tetrahydro-pyran-2-yloxy)-cyclopentanecarboxylic acid ethyl ester (4.7 g, 19.59 mmol). The reaction was stirred at 25° C. for 18 h. At this time, the reaction was poured onto ice/water. This mixture was filtered through a pad of celite (methylene chloride as eluent). The organics were washed with a saturated aqueous sodium chloride solution (1×100 mL), dried over sodium sulfate, filtered, and concentrated in vacuo to give [2-(tetrahydro-pyran-2-yloxy)-cyclopentyl]-methanol (3.25 g, 83.6%) as a clear liquid: EI-HRMS m/e calcd for $C_{11}H_{20}O_3$ (M$^+$) 200.1412. found 200.1412.

A solution of triphenylphosphine (1.70 g, 6.49 mmol) and imidazole (884 mg, 12.98 mmol) in methylene chloride (8.32 mL) cooled to 0° C. was treated with iodine (1.64 g, 6.49 mmol). After the iodine was completely dissolved, a solution of [2-(tetrahydro-pyran-2-yloxy)-cyclopentyl]-methanol (1.0 g, 4.99 mmol) was added to the reaction mixture. The reaction was stirred at 0° C. for 1 h and at 25° C. for 2 h. At this time, the reaction was poured into water (100 mL) and extracted with methylene chloride (1×30 mL). The organics were washed with a saturated aqueous sodium thiosulfate solution (1×50 mL), dried over sodium sulfate, filtered, and concentrated in vacuo at 25° C. Flash chromatography (Merck Silica gel 60, 230-400 mesh, 80/20 hexanes/ethyl acetate) afforded 2-(2-iodomethyl-cyclopentyloxy)-tetrahydropyran (1.17 g, 75.8%) as a clear liquid: EI-HRMS m/e calcd for $C_{11}H_{19}IO_2$ (M$^+$) 309.0352. found 309.0348.

A solution of freshly prepared lithium diisopropylamide (10.4 mL of a 0.31M stock solution, 3.22 mmol) cooled to −78° C. was treated with 3,4-dichlorophenylacetic acid methyl ester (prepared as in Example 1, 642 mg 2.93 mmol) in tetrahydrofuran/1,3-dimethyl-3,4,5,6-tetrahydro-2(1H)-pyrimidinone (7.33 mL, 3:1). The resulting solution was stirred at −78° C. for 45 min. A solution of 2-(2-iodomethyl-cyclopentyloxy)-tetrahydropyran (1.0 g, 3.22 mmol) in 1,3-dimethyl-3,4,5,6-tetrahydro-2(1H)-pyrimidinone (1 mL) was then added. The reaction mixture was stirred at −78° C. for 2 h. The reaction was then warmed to 25° C. and was stirred at 25° C. for 16 h. The reaction mixture was then quenched by the dropwise addition of a saturated aqueous ammonium chloride solution (10 mL). This mixture was poured into water (100 mL) and extracted with methylene chloride 3×50 mL). The organics were dried over sodium sulfate, filtered, and concentrated in vacuo. Flash chromatography (Merck Silica gel 60, 230-400 mesh, 90/10 hexanes/ethyl acetate) afforded 2-(3,4-dichloro-phenyl)-3-[2-(tetrahydro-pyran-2-yloxy)-cyclopentyl]-propionic acid methyl ester (880 mg, 74.8%) as a pale yellow oil: EI-HRMS m/e calcd for $C_{20}H_{26}Cl_2O_4$ (M$^+$) 400.1208. found 400.1203.

2-(3,4-Dichloro-phenyl)-3-[2-(tetrahydro-pyran-2-yloxy)-cyclopentyl]-propionic acid methyl ester (400 mg, 0.99 mmol) and methylurea (110.7 mg, 1.49 mmol) in a solution of magnesium methoxide in methanol (7.4 wt. %, 2.85 mL, 1.99 mmol) was heated under reflux at 110° C. for 6 h. The reaction mixture was then concentrated in vacuo and filtered through a plug of celite (ethyl acetate as eluent). Flash chromatography (Merck Silica gel 60, 230-400 mesh, 100% ethyl acetate) afforded 1-{2-(3,4-dichloro-phenyl)-3-[2-(tetrahydro-pyran-2-yloxy)-cyclopentyl]-propionyl}-3-methyl-urea (52 mg, 11.8%) as a white solid: mp 68-70° C.; FAB-HRMS m/e calcd for $C_{21}H_{28}Cl_2N_2O_4$ (M+H)$^+$ 443.1504. found 443.1499.

A solution of 1-{2-(3,4-dichloro-phenyl)-3-[2-(tetrahydro-pyran-2-yloxy)-cyclopentyl]-propionyl}-3-methyl-urea (45 mg, 0.10 mmol) in ethanol (1.01 mL) was treated with pyridinium p-toluenesulfonate (2.5 mg, 0.01 mmol). The reaction mixture was heated to 55° C. for 5 h. At this time, the reaction was concentrated in vacuo. Flash chromatography (Merck Silica gel 60, 230-400 mesh, 100% ethyl acetate) afforded the 1-[2-(3,4-dichloro-phenyl)-3-(2-hydroxy-cyclopentyl)-propionyl]-3-methyl-urea (30.4 mg, 83.4%) as a white solid: mp 62-64° C.; FAB-HRMS m/e calcd for $C_{16}H_{20}Cl_2N_2O_3$ $(M+H)^+$ 359.0929. found 359.0929.

EXAMPLE 25

2-(3,4-Dichloro-phenyl)-3-(2-hydroxy-cyclopentyl)-N-thiazol-2-yl-propionamide

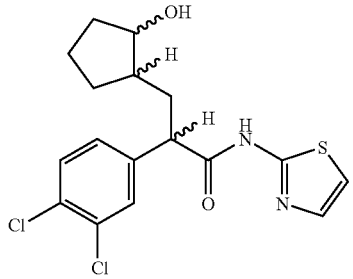

A solution of 2-(3,4-dichloro-phenyl)-3-[2-(tetrahydropyran-2-yloxy)-cyclopentyl]-propionic acid methyl ester (prepared as in Example 24, 2.3 g, 5.73 mmol) in ethanol (57.3 mL) at 25° C. was treated with pyridinium p-toluenesulfonate (144 mg, 0.57 mmol). The resulting solution was heated under reflux for 18 h. At this time, the reaction was cooled to 25° C. and concentrated in vacuo. Flash chromatography (Merck Silica gel 60, 230-400 mesh, 50/50 hexanes/ethyl acetate) afforded 2-(3,4-dichloro-phenyl)-3-(2-hydroxy-cyclopentyl)-propionic acid methyl ester (1.84 g, 100%) as a clear oil: EI-HRMS m/e calcd for $C_{15}H_{18}Cl_2O_3$ $(M+Na)^+$ 339.0527. found 339.0528.

A mixture of 2-(3,4-dichloro-phenyl)-3-(2-hydroxy-cyclopentyl)-propionic acid methyl ester (262.2 mg, 0.82 mmol) and 2-aminothiazole (165 mg, 1.65 mmol) in a solution of magnesium methoxide in methanol (7.4 wt. %, 2.60 mL, 1.81 mmol) was heated to 100° C. for 18 h. At this time, the reaction mixture was cooled to 25° C. and filtered through a pad of celite (ethyl acetate as eluent). The filtrate was then concentrated in vacuo. Flash chromatography (Merck Silica gel 60, 230-400 mesh, 75/25 ethyl acetate/hexanes) afforded the 2-(3,4-dichloro-phenyl)-3-(2-hydroxy-cyclopentyl)-N-thiazol-2-yl-propionamide (174 mg, 54.6%) as a white solid: mp 86-88° C.; EI-HRMS m/e calcd for $C_{17}H_{18}Cl_2N_2O_2S$ $(M+Na)^+$ 407.0358. found 407.0361.

EXAMPLE 26

3-(2-Hydroxy-cyclopentyl)-2-(4-methanesulfonyl-phenyl)-N-thiazol-2-yl-propionamide

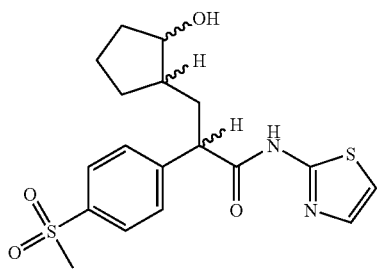

A solution of diisopropylamine (846 μL, 6.04 mmol) in dry tetrahydrofuran (4.4 mL) and 1,3-dimethyl-3,4,5,6-tetrahydro-2(1H)-pyrimidinone (1.4 mL) was cooled to -78° C. and then treated with a 2.5M solution of n-butyllithium in hexanes (2.4 mL, 6.04 mmol). The reaction mixture was stirred at -78° C. for 30 min and then was treated with a solution of (4-methanesulfonyl-phenyl)-acetic acid methyl ester (prepared as in Example 8, 1.06 g, 4.64 mmol) in dry tetrahydrofuran (4.4 mL) and 1,3-dimethyl-3,4,5,6-tetrahydro-2(1H)-pyrimidinone (1.4 mL). The resulting reaction mixture was allowed to stir at -78° C. for 45 min and then the reaction mixture was treated with a solution of 2-(2-iodomethyl-cyclopentyloxy)-tetrahydropyran (prepared as in Example 24, 1.87 g, 6.04 mmol) in a small amount of dry tetrahydrofuran. The reaction mixture was stirred at -78° C. and then allowed to warm to 25° C., where it was stirred for 68 h. The reaction mixture was quenched with water (100 mL) and then concentrated in vacuo to remove tetrahydrofuran. The aqueous residue was extracted with ethyl acetate (2×100 mL). The combined organic extracts were dried over sodium sulfate, filtered, and concentrated in vacuo. Flash chromatography (Merck Silica gel 60, 70-230 mesh, 7/3 hexanes/ethyl acetate) afforded the 2-(4-methanesulfonyl-phenyl)-3-[2-(tetrahydropyran-2-yloxy)-cyclopentyl]-propionic acid methyl ester (859.2 mg, 45%) as a light yellow oil: FAB-HRMS m/e calcd for $C_{21}H_{30}O_6S$ $(M+H)^+$ 411.1841. found 411.1831.

2-Aminothiazole (314.3 mg, 3.14 mmol) and 2-(4-methanesulfonyl-phenyl)-3-[2-(tetrahydropyran-2-yloxy)-cyclopentyl]-propionic acid methyl ester (859.2 g, 2.09 mmol) were treated with a solution of magnesium methoxide in methanol (7.4 wt. %, 12 mL, 8.37 mmol). The resulting reaction mixture was heated under reflux for 24 h. The reaction mixture was allowed to cool to 25° C. and then filtered through a pad of celite. The pad of celite was washed well with ethyl acetate until the washings indicated the absence of product by thin layer chromatography. The filtrate was then washed with a 10% aqueous hydrochloric acid solution 3×100 mL). The organic layer was then dried over magnesium sulfate, filtered, and concentrated in vacuo. Flash chromatography (Merck Silica gel 60, 70-230 mesh, 1/1 hexanes/ethyl acetate) afforded 2-(4-methanesulfonyl-phenyl)-3-[2-(tetrahydropyran-2-yloxy)-cyclopentyl]-N-thiazol-2-yl-propionamide (377.4 mg, 38%) as a yellow oil: EI-HRMS m/e calcd for $C_{23}H_{30}N_2O_5S_2$ $(M^+)$ 478.1596. found 478.1604.

A solution of 2-(4-methanesulfonyl-phenyl)-3-[2-(tetrahydropyran-2-yloxy)-cyclopentyl]-N-thiazol-2-yl-propionamide (350.8 mg, 0.73 mmol) in ethanol (7.3 mL) was treated with pyridinium p-toluenesulfonate (18.4 mg, 0.073 mmol). The resulting reaction mixture was heated at 60° C. for 4 h. The reaction mixture was allowed to cool to 25° C. and then concentrated in vacuo. The resulting yellow residue was diluted with ethyl acetate (100 mL) and then washed with a saturated aqueous sodium chloride solution (1×100 mL). The organic layer was dried over magnesium sulfate, filtered, and concentrated in vacuo. Flash chromatography (Merck Silica gel 60, 70-230 mesh, 1/3 hexanes/ethyl acetate) afforded the 3-(2-hydroxy-cyclopentyl)-2-(4-methanesulfonyl-phenyl)-N-thiazol-2-yl-propionamide (77.0 mg, 27%) as a white solid: mp 205-206° C.; EI-HRMS m/e calcd for $C_{18}H_{22}N_2O_4S_2$ $(M^{+})$ 394.1021. found 394.1018.

EXAMPLE 27

1-[2-(3,4-Dichloro-phenyl)-3-(2-oxo-cyclopentyl)-propionyl]-3-methyl-urea

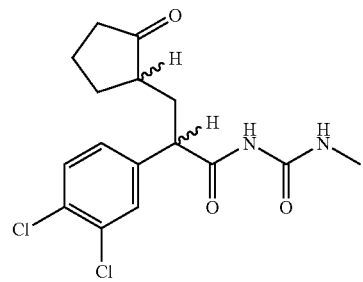

A solution of 1-[2-(3,4-dichloro-phenyl)-3-(2-hydroxy-cyclopentyl)-propionyl]-3-methyl-urea (prepared as in Example 24, 28.1 mg, 0.07 mmol) in methylene chloride (0.78 mL) was treated with pyridinium chlorochromate (20 wt. % on basic alumina, 101 mg, 0.09 mmol). The reaction mixture was stirred at 25° C. for 4 h. At this time, the reaction was filtered through a plug of celite (ethyl acetate as eluent). The filtrate was concentrated in vacuo. Flash chromatography (Merck Silica gel 60, 230-400 mesh, 100% ethyl acetate) afforded 1-[2-(3,4-dchloro-phenyl)-3-(2-oxo-cyclopentyl)-propionyl]-3-methyl-urea (21.9 mg, 78.4%) as a white foam: mp 63-65° C.; FAB-HRMS m/e calcd for $C_{16}H_{18}Cl_2N_2O_3$ (M+H)$^+$ 357.0773. found 357.0780.

EXAMPLE 28

2-(3,4-Dichloro-phenyl)-3-(2-oxo-cyclopentyl)-N-thiazol-2-yl-propionamide

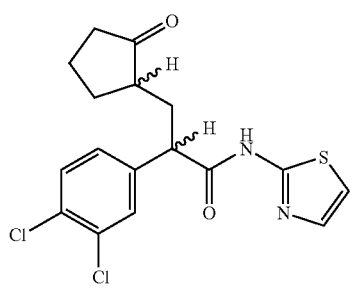

A solution of 2-(3,4-dichloro-phenyl)-3-(2-hydroxy-cyclopentyl)-N-thiazol-2-yl-propionamide (prepared as in Example 25, 162.5 mg, 0.42 mmol) in methylene chloride (4.2 mL) was treated with pyridinium chlorochromate (20 wt. % on basic alumina, 545 mg, 0.50 mmol). The reaction mixture was stirred at 25° C. for 2 h. At this time, the reaction was filtered through a plug of celite (ethyl acetate as eluent). The filtrate was concentrated in vacuo. Flash chromatography (Merck Silica gel 60, 230-400 mesh, 50/50 hexanes/ethyl acetate) afforded 2-(3,4-dichloro-phenyl)-3-(2-oxo-cyclopentyl)-N-thiazol-2-yl-propionamide (64.8 mg, 40.1%) as a light tan solid: mp 79-81° C.; EI-HRMS m/e calcd for $C_{17}H_{16}Cl_2N_2O_2S$ (M+H)$^+$ 383.0383. found 383.0384.

EXAMPLE 29

2-(4-Methanesulfonyl-phenyl)-3-(2-oxo-cyclopentyl)-N-thiazol-2-yl-propionamide

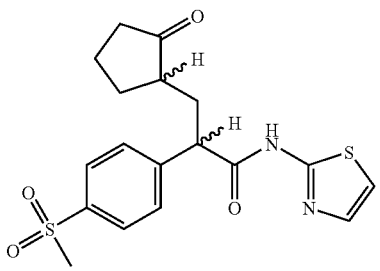

A solution of 3-(2-hydroxy-cyclopentyl)-2-(4-methanesulfonyl-phenyl)-N-thiazol-2-yl-propionamide (prepared as in Example 26, 72.4 mg, 0.184 mmol) in methylene chloride (1.8 mL) was treated with pyridinium chlorochromate (20 wt. % on basic alumina, 237.3 mg, 0.22 mmol). The resulting reaction mixture was stirred at 25° C. for 3 h, at which time, thin layer chromatography indicated a small amount of the 3-(2-hydroxy-cyclopentyl)-2-(4-methanesulfonyl-phenyl)-N-thiazol-2-yl-propionamide. The reaction mixture was then treated with an additional amount of pyridinium chlorochromate (20 wt. % on basic alumina, 237.3 mg, 0.220 mmol). The reaction mixture was allowed to stir at 25° C. for 4 h and then filtered through a pad of celite. The pad of celite was washed well with ethyl acetate until the washings indicated the absence of product by thin layer chromatography. The filtrate was then concentrated in vacuo. Flash chromatography (Merck Silica gel 60, 230-400 mesh, 3/7 hexanes/ethyl acetate) afforded 2-(4-methanesulfonyl-phenyl)-3-(2-oxo-cyclopentyl)-N-thiazol-2-yl-propionamide (10.2 mg, 14%) as a white solid: mp 228-230° C.; EI-HRMS m/e calcd for $C_{18}H_{20}N_2O_4S_2$ (M$^+$) 392.0865. found 392.0871.

EXAMPLE 30

2(R)-(3-Chloro-4-methanesulfonyl-phenyl)-3-(2-oxo-cyclopentyl)-N-pyrazin-2-yl-propionamide

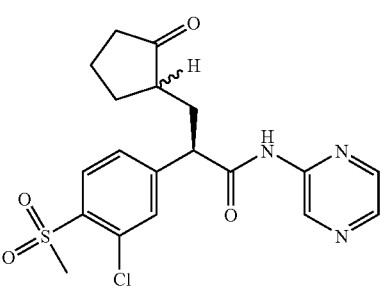

A mixture of (3-chloro-4-methylsulfanyl-phenyl)-acetic acid (prepared as in Example 4, 10.48 g, 48.4 mmol) and potassium carbonate (20.1 g, 145.1 mmol) in acetone (65 mL) was cooled to −10° C. The pale yellow slurry was then treated dropwise with trimethylacetyl chloride (6.25 mL, 50.8 mmol) while maintaining the temperature below −10° C. The resulting reaction mixture was stirred at −10° C. for 15 min and then allowed to warm to 0° C. where it was stirred for 10 min. The reaction mixture was re-cooled to −10° C. and then treated with (1R,2R)-(−)-pseudoephedrine (11.99 g, 72.5 mmol), resulting in an exotherm. The reaction mixture was stirred −10° C. for 10 min and then warmed to 25° C., where it was stirred for 1 h. After such time, thin layer chromatography analysis indicated that the reaction was complete. The reaction mixture was then quenched with water (50 mL) and then extracted with ethyl acetate (1×100 mL). The organic layer was washed with water (2×40 mL). The aqueous layers were combined and back-extracted with ethyl acetate (2×50 mL). The combined organic layers were dried over magnesium sulfate, filtered, and concentrated in vacuo. The crude material was recrystallized from ethyl acetate (45 mL) and hexanes (80 mL) to afford 2-(3-chloro-4-methylsulfanyl-phenyl)-N-[2(R)-hydroxy-1(R)-methyl-2(R)-phenyl-ethyl]-N-methyl-acetamide (13.75 g, 78%) as a light yellow solid: mp 111.5-112.9° C.; $[\alpha]^{23}_{589}=-97.2°$ (c=0.104, chloroform); FAB-HRMS m/e calcd for $C_{19}H_{22}ClNSO_2$ $(M+H)^+$ 364.1138. found 364.1142.

A solution of 1,1,1,3,3,3-hexamethyldisilizane (14.5 mL, 68.7 mmol) in tetrahydrofuran (45.8 mL) cooled to −45° C. was treated with a 2.5M solution of n-butyllithium in hexanes (25.8 mL, 63.2 mmol). The resulting solution was stirred at −45° C. for 30 min. At this time, the reaction was treated with a solution of 2-(3-chloro-4-methylsulfanyl-phenyl)-N-[2(R)-hydroxy-1(R)-methyl-2(R)-phenyl-ethyl]-N-methyl-acetamide (10.0 g, 27.48 mmol) in tetrahydrofliran (45.86 mL). Upon complete addition, the reaction was warmed to 0° C. and was stirred at 0° C. for 30 min. At this time, the reaction was re-cooled to −45° C. and then was treated with 2-(2-iodomethyl-cyclopentyloxy)-tetrahydropyran (prepared as in Example 24, 12.8 g, 41.22 mmol) in 1,3-dimethyl-3,4,5,6-tetrahydro-2(1H)-pyrimidinone (8.4 mL). At this time, the reaction was warmed to 0° C., where it was stirred for 3 h. At this time, the reaction was diluted with a saturated aqueous sodium chloride solution (100 mL). The phases were partitioned. The aqueous phase was extracted into ethyl acetate (3×50 mL). The combined organics were washed with a 10% aqueous hydrochloric acid solution and an aqueous sodium bicarbonate solution, dried over sodium sulfate, filtered, and concentrated in vacuo. Flash chromatography (Merck Silica gel 60, 230-400 mesh, 75/25 ethyl acetate/hexanes) afforded 2(R)-(3-chloro-4-methylsulfanyl-phenyl)-N-(2(R)-hydroxy-1(R)-methyl-2(R)-phenyl-ethyl)-N-methyl-3-[2-(tetrahydro-pyran-2-yloxy)-cyclopentyl]-propionamide (10.6 g, 70.6%) as a yellow foam: EI-HRMS m/e calcd for $C_{30}H_{40}ClNO_4S$ $(M+Na)^+$ 568.2259. found 568.2262.

A solution of 2(R)-(3-chloro-4-methylsulfanyl-phenyl)-N-(2(R)-hydroxy-1(R)-methyl-2(R)-phenyl-ethyl)-N-methyl-3-[2-(tetrahydro-pyran-2-yloxy)-cyclopentyl]-propionamide (1.04 g, 1.91 mmol) in ethanol (19.1 mL) was treated with pyridinium p-toluenesulfonate (48 mg, 0.19 mmol). The resulting solution was heated to 55° C. for 2 h. At this time, the reaction was concentrated in vacuo. Flash chromatography (Merck Silica gel 60, 230-400 mesh, 75/25 ethyl acetate/hexanes) afforded 2(R)-(3-chloro-4-methylsulfanyl-phenyl)-3-(2-hydroxy-cyclopentyl)-N-(2(R)-hydroxy-1(R)-methyl-2(R)-phenyl-ethyl)-N-methyl-propionamide (0.82 g, 93.0%) as a white foam: EI-HRMS m/e calcd for $C_{25}H_{32}ClNO_3S$ $(M+Na)^+$ 484.1684. found 484.1674.

A mixture of 2(R)-(3-chloro-4-methylsulfanyl-phenyl)-3-(2-hydroxy-cyclopentyl)-N-(2(R)-hydroxy-1(R)-methyl-2(R)-phenyl-ethyl)-N-methyl-propionamide (3.63 g, 7.85 mmol), N-methylmorpholine N-oxide (2.76 g, 23.5 mmol), and powdered molecular sieves (7.85 g) in methylene chloride (15.7 mL) at 25° C. was treated with tetrapropylammonium perrhuthenate (276 mg, 0.78 mmol). The resulting mixture was stirred at 25° C. for 20 min. At this time, the reaction was filtered through a pad of silica (ethyl acetate as eluent). The filtrate was concentrated in vacuo. Flash chromatography (Merck Silica gel 60, 230-400 mesh, 75/25 ethyl acetate/hexanes) afforded 2(R)-(3-chloro-4-methylsulfanyl-phenyl)-N-methyl-N-(1(R)-methyl-2-oxo-2(R)-phenyl-ethyl)-3-(2-oxo-cyclopentyl)-propionamide (2.75 g, 76.5%) as a white foam: EI-HRMS m/e calcd for $C_{25}H_{28}ClNO_3S(M^+)$ 457.1478. found 457.1489.

A solution of 2(R)-(3-chloro-4-methylsulfanyl-phenyl)-N-methyl-N-(1(R)-methyl-2-oxo-2(R)-phenyl-ethyl)-3-(2-oxo-cyclopentyl)-propionamide (2.75 g, 6.0 mmol) in dioxane (9.38 mL) was treated with an 18M aqueous hydrochloric acid solution (9.38 mL). The reaction was then heated to 120° C. for 18 h. At this time, the reaction was cooled to 25° C., diluted with water (100 mL), and extracted with a 90/10 methylene chloride/methanol solution 3×100 mL). The organics were dried over sodium sulfate, filtered, and concentrated in vacuo. Flash chromatography (Merck Silica gel 60, 230-400 mesh, ethyl acetate) afforded 2(R)-(3-chloro-4-methylsulfanyl-phenyl)-3-(2-oxo-cyclopentyl)-propionic acid (1.54 g, 82%) as a yellow oil: EI-HRMS m/e calcd for $C_{15}H_{17}ClO_3S$ $(M^+)$ 312.0587. found 312.0581.

A solution of 2(R)-(3-chloro-4-methylsulfanyl-phenyl)-3-(2-oxo-cyclopentyl)-propionic acid (683.2 mg, 2.18 mmol), formic acid (2.47 mL, 65.5 mmol), and water (0.41 mL) cooled to 0° C. was treated with a 30% aqueous hydrogen peroxide solution (1.11 mL, 10.9 mmol). The reaction was stirred at 0° C. for 1 h. At this time, the reaction was treated with a saturated aqueous sodium sulfite solution. The resulting solution was poured into water (50 mL) and was then extracted into methylene chloride 3×50 mL). The organics were dried over sodium sulfate, filtered, and concentrated in vacuo to afford 2(R)-(3-chloro-4-methanesulfunyl-phenyl)-3-(2-oxo-cyclopentyl)-propionic acid (724 mg, 100%) as a white foam: EI-HRMS m/e calcd for $C_{15}H_{17}ClO_4S$ $(M+Na)^+$ 351.0428. found 351.0433.

A solution of potassium permanganate (101 mg, 0.64 mmol) in water (1.83 mL) was treated with a solution of 2(R)-(3-chloro-4-methanesulfanyl-phenyl)-3-(2-oxo-cyclopentyl)-propionic acid (191.5 mg, 0.58 mmol) in methanol (5.8 mL). The reaction was stirred at 25° C. for 1 h. At this time, the reaction was diluted with methanol and then was filtered through a pad of celite. The filtrate was concentrated in vacuo and was azeotroped with acetonitrile. Flash chromatography (Merck Silica gel 60, 230-400 mesh, 90/10 methylene chloride/methanol with glacial acetic acid) afforded 2(R)-(3-chloro-4-methanesulfonyl-phenyl)-3-(2-oxo-cyclopentyl)-propionic acid (87 mg, 43%) as an off-white foam: EI-HRMS m/e calcd for $C_{15}H_{17}ClO_5S$ $(M-H_2O)^+$ 326.0379. found 326.0378.

A solution of 2(R)-(3-chloro-4-methanesulfonyl-phenyl)-3-(2-oxo-cyclopentyl)-propionic acid (125 mg, 0.36 mmol) in methylene chloride (3.62 mL) cooled to 0° C. was treated with a 2.0M solution of oxalyl chloride in methylene chloride (0.20 mL, 0.39 mmol) and a few drops of N,N-dimethylformamide. The reaction mixture was stirred at 0° C. for 10 min and at 25° C. for 20 min. The reaction mixture was then treated with a solution of 2-aminopyrazine (76 mg, 0.80 mmol) and pyridine (0.06 mL, 0.80 mmol) in tetrahydrofurane (1.81 mL). This solution was stirred at 25° C. for 1 h. At this time, the reaction was concentrated in vacuo. Flash chromatography (Merck Silica gel 60, 230-400 mesh, 75/25 ethyl acetate/hexanes) afforded 2(R)-(3-chloro-4-methanesulfonyl-phenyl)-3-(2-oxo-cyclopentyl)-N-pyrazin- 2-yl-propionamide (77.6 mg, 50.7%) as a white foam: EI-HRMS m/e calcd for $C_{19}H_{20}ClN_3O_4S$ (M+) 421.0863. found 421.0868.

EXAMPLE 31

2(R)-(3-Chloro-4-methanesulfonyl-phenyl)-3-(2-hydroxy-cyclopentyl)-N-pyrazin-2-yl-propionamide

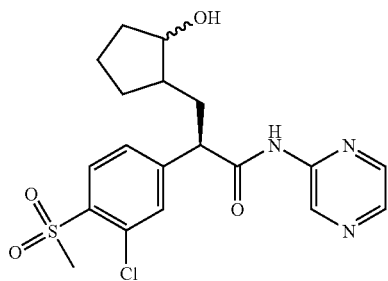

A solution of 2(R)-(3-chloro-4-methanesulfonyl-phenyl)-3-(2-oxo-cyclopentyl)-N-pyrazin-2-yl-propionamide (prepared as in Example 30, 13.5 mg, 0.03 mmol) in ethanol (0.32 mL) cooled to 0° C. was treated with sodium borohydride (1.2 mg, 0.03 mmol). The reaction mixture was stirred at 0° C. for 20 min. At this time, the reaction was diluted with water (25 mL). The layers were separated. The aqueous layer was extracted with ethyl acetate 3×30 mL). The combined organics were dried over sodium sulfate, filtered, and concentrated in vacuo. Flash chromatography (Merck Silica gel 60, 230-400 mesh, ethyl acetate) afforded 2(R)-(3-chloro-4-methanesulfonyl-phenyl)-3-(2-hydroxy-cyclopentyl)-N-pyrazin-2-yl-propionamide (10.1 mg, 75.5%) as a white foam: EIHRMS m/e calcd for $C_{19}H_{22}ClN_3O_4S$ (M+Na)+ 446.0912. found 446.0916.

EXAMPLE 32

2-(3-Chloro-4-methanesulfonyl-phenyl)-3-(2-hydroxyimino-cyclopentyl)-N-pyrazin-2-yl-propionamide

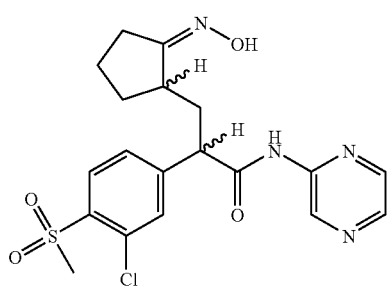

A mixture of 2(R)-(3-chloro-4-methylsulfanyl-phenyl)-3-(2-hydroxy-cyclopentyl)-N-(2(R)-hydroxy-1(R)-methyl-2(R)-phenyl-ethyl)-N-methyl-propionamide (prepared as in Example 30, 3.63 g, 7.85 mmol), N-methylmorpholine N-oxide (7.37 g, 15.95 mmol), and powdered molecular sieves (32 g) in methylene chloride (63.8 mL) at 0° C. was treated with tetrapropylammonium perrhuthenate (1.12 mg, 3.19 mmol). The resulting mixture was stirred at 0° C. for 1 h and at 25° C. for 3 h. At this time, the reaction was filtered through a pad of silica (ethyl acetate as eluent). The filtrate was concentrated in vacuo. Flash chromatography (Merck Silica gel 60, 230-400 mesh, 75/25 ethyl acetate/hexanes) afforded 2(R)-(3-chloro-4-methylsulfanyl-phenyl)-N-methyl-N-(1(R)-methyl-2-oxo-2(R)-phenyl-ethyl)-3-(2-oxo-cyclopentyl)-propionamide (5.03 g, 68.8%) and 2(R)-(3-chloro-4-methylsulfonyl-phenyl)-N-methyl-N-(1(R)-methyl-2-oxo-2(R)-phenyl-ethyl)-3-(2-oxo-cyclopentyl)-propionamide (1.29 g, 16.5%) as a white foam: EI-HRMS m/e calcd for $C_{25}H_{28}ClNO_5S$ (M+Na)+ 512.1269. found 512.1273.

A solution of 2(R)-(3-chloro-4-methylsulfonyl-phenyl)-N-methyl-N-(1(R)-methyl-2-oxo-2(R)-phenyl-ethyl)-3-(2-oxo-cyclopentyl)-propionamide (1.29 g, 2.63 mmol) in dioxane (4.43 mL) was treated with an 18M aqueous hydrochloric acid solution (4.43 mL). The reaction was then heated to 120° C. for 18 h. At this time, the reaction was cooled to 25° C., diluted with water (50 mL), and extracted with a 90/10 methylene chloride/methanol solution 3×100 mL). The organics were dried over sodium sulfate, filtered, and concentrated in vacuo. Flash chromatography (Merck Silica gel 60, 230-400 mesh, ethyl acetate) afforded racemic 2-(3-chloro-4-methylsulfonyl-phenyl)-3-(2-oxo-cyclopentyl)-propionic acid (563.3 mg, 62.1%) as a light tan foam. A solution of 2-(3-chloro-4-methanesulfonyl-phenyl)-3-(2-oxo-cyclopentyl)-propionic acid (563.3 mg, 1.6 mmol) in methylene chloride (16.4 mL) cooled to 0° C. was treated with a 2.0M solution of oxalyl chloride in methylene chloride (0.90 mL, 1.80 mmol) and a few drops of N,N-dimethylformamide. The reaction mixture was stirred at 0° C. for 10 min and at 25° C. for 20 min. The reaction mixture was then treated with a solution of 2-aminopyrazine (342 mg, 3.60 mmol) and pyridine (0.3 mL, 3.60 mmol) in tetrahydrofuran (8.2 mL). This solution was stirred at 25° C. for 18 h. At this time, the reaction was concentrated in vacuo. The residue was dissolved in methylene chloride (100 mL) and washed with a 1N aqueous hydrochloric acid solution (2×100 mL), dried over sodium sulfate, filtered, and concentrated in vacuo. Flash chromatography (Merck Silica gel 60, 230-400 mesh, 75/25 ethyl acetate/hexanes) afforded 2-(3-chloro-4-methanesulfonyl-phenyl)-3-(2-oxo-cyclopentyl)-N-pyrazin-2-yl-propionamide (198.8 mg, 28.9%) as a clear oil.

A solution of 2-(3-chloro-4-methanesulfonyl-phenyl)-3-(2-oxo-cyclopentyl)-N-pyrazin-2-yl-propionamide (99.3 mg, 0.23 mmol) in pyridine (0.69 ML) and methanol (0.69 mL) at 25° C. was treated with hydroxylamine hydrochloride (24.5 mg, 0.35 mmol). The reaction mixture was heated under reflux for 12 h. At this time, the reaction was cooled to 25° C. and was concentrated in vacuo. The resulting residue was dissolved in ethyl acetate (75 mL) and was washed with a 1N aqueous sodium hydroxide solution (1×50 mL) and a saturated aqueous sodium chloride solution (1×50 mL), dried over sodium sulfate, filtered, and concentrated in vacuo. Flash chromatography (Merck Silica gel 60, 230-400 mesh, 75/25 ethyl acetate/hexanes) afforded 2-(3-chloro-4-methanesulfonyl-phenyl)-3-(2-hydroxyimino-cyclopentyl)-N-pyrazin-2-yl-propionamide (5.6 mg, 5.4%) as a white wax: (ES)−-HRMS m/e calcd for $C_{19}H_{21}ClN_4O_4S$ (M−H)− 435.0899. found 435.0902.

EXAMPLE 33

2-(3-Chloro-4-methanesulfonyl-phenyl)-3-(2-methoxyimino-cyclopentyl)-N-pyrazin-2-yl-propionamide

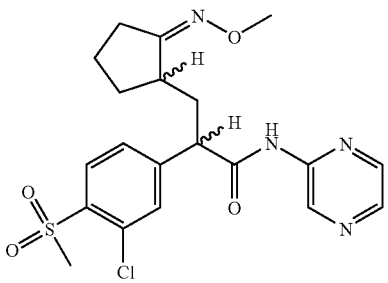

A solution of 2-(3-chloro-4-methanesulfonyl-phenyl)-3-(2-oxo-cyclopentyl)-N-pyrazin-2-yl-propionamide (prepared as in Example 32, 99.5 mg, 0.23 mmol) in pyridine (0.69 mL) and methanol (0.69 mL) at 25° C. was treated with methoxyamine hydrochloride (30 mg, 0.35 mmol). The reaction mixture was heated under reflux for 12 h. At this time, the reaction was cooled to 25° C. and was concentrated in vacuo. The resulting residue was dissolved in ethyl acetate (75 mL) and was washed with a 1N aqueous sodium hydroxide solution (1×50 mL) and a saturated aqueous sodium chloride solution (1×50 mL), dried over sodium sulfate, filtered, and concentrated in vacuo. Flash chromatography (Merck Silica gel 60, 230-400 mesh, 75/25 ethyl acetate/hexanes) afforded 2-(3-chloro-4-methanesulfonyl-phenyl)-3-(2-methoxyimino-cyclopentyl)-N-pyrazin-2-yl-propionamide (92.7 mg, 87.2%) as a white wax: mp 74-76° C.; FAB-HRMS m/e calcd for $C_{20}H_{23}ClN_4O_4S$ (M+Na)$^+$ 473.1021. found 473.1024.

EXAMPLE 34

2-(3,4-Dichloro-phenyl)-3-(2,2-difluoro-cyclopentyl)-N-thiazol-2-yl-propionamide

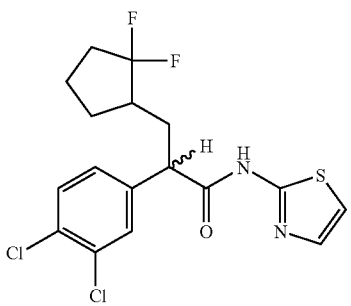

A mixture of 2-(3,4-dichloro-phenyl)-3-(2-hydroxy-cyclopentyl)-propionic acid methyl ester (prepared as in Example 25, 408.5 mg, 1.28 mmol), N-methylmorpholine N-oxide (679 mg, 5.79 mmol), and powdered molecular sieves (1.29 g) in methylene chloride (2.6 mL) at 25° C. was treated with tetrapropylammonium perrhuthenate (45 mg, 0.12 mmol). The resulting mixture was stirred at 25° C. for 2 h. At this time, the reaction was filtered through a pad of celite (ethyl acetate as eluent). The filtrate was concentrated in vacuo. Flash chromatography (Merck Silica gel 60, 230-400 mesh, 75/25 hexanes/ethyl acetate) afforded 2-(3,4-dichloro-phenyl)-3-(2-oxo-cyclopentyl)-propionic acid methyl ester (278.2 mg, 68.5%) as a clear oil: EI-HRMS m/e calcd for $C_{15}H_{16}C_{12}O_3$ (M$^+$) 314.0476. found 314.0476.

A solution of 2-(3,4-dichloro-phenyl)-3-(2-oxo-cyclopentyl)-propionic acid methyl ester (270 mg, 0.85 mmol) in methylene chloride (0.43 mL) was treated with diethylaminosulfur trifluoride (0.17 mL, 1.28 mmol). The resulting mixture was heated at 60° C. for 18 h. At this time, the reaction was cooled to 25° C. and was diluted with water (50 mL). This solution was extracted into methylene chloride 3×30 mL). The organics were dried over sodium sulfate, filtered, and concentrated in vacuo. Flash chromatography (Merck Silica gel 60, 230-400 mesh, 75/25 hexanes/ethyl acetate) afforded 2-(3,4-dichloro-phenyl)-3-(2,2-difluoro-cyclopentyl)-propionic acid methyl ester (278.2 mg, 68.5%) as a light tan oil: EI-HRMS m/e calcd for $C_{15}H_{16}Cl_2F_2O_2$ (M$^+$) 336.0495. found 336.0510.

A mixture of 2-(3,4-dichloro-phenyl)-3-(2,2-difluoro-cyclopentyl)-propionic acid methyl ester (265 mg, 0.73 mmol) and 2-aminothiazole (18 mg, 0.18 mmol) in a solution of magnesium methoxide in methanol (7.4 wt. %, 0.28 iL, 0.19 mmol) was heated to 110° C. for 18 h. At this time, the reaction mixture was cooled to 25° C. and then concentrated in vacuo. Flash chromatography (Merck Silica gel 60, 230-400 mesh, 50/50 hexanes/ethyl acetate) afforded 2-(3,4-dichloro-phenyl)-3-(2,2-difluoro-cyclopentyl)-N-thiazol-2-yl-propionamide (8.3 mg, 23%) as a yellow oil: EI-HRMS m/e calcd for $C_{17}H_{16}F_2Cl_2N_2OS$ (M+H)$^+$ 405.0402. found 405.0407.

EXAMPLE 35

1-[2-(3,4-Dichloro-phenyl)-3-(3-hydroxy-cyclopentyl)-propionyl]-3-methyl-urea

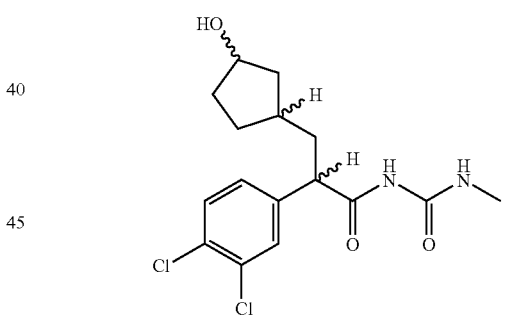

A solution of 3-iodomethyl-cyclopentanone (12.84 g, 57.31 mmol, prepared according to J. Org Chem. 1981, 46, 2412-2414) in methanol (143 ML) was cooled to 0° C. and then slowly treated with sodium borohydride powder (2.38 g, 63.04 mmol). The resulting reaction mixture was stirred at 0° C. for 40 min and then slowly quenched with water (100 mL). The reaction mixture was then concentrated in vacuo to remove methanol. The resulting aqueous residue was extracted with diethyl ether 3×100 mL). The combined organic extracts were dried over magnesium sulfate, filtered, and concentrated in vacuo. Flash chromatography (Merck Silica gel 60, 70-230 mesh, 100% methylene chloride) afforded 3-iodomethyl-cyclopentanol (7.71 g, 59%) as a green liquid: EI-HRMS m/e calcd for $C_6H_{11}IO$ (M$^+$) 225.9855. found 225.9856.

A solution of 3-iodomethyl-cyclopentanol (7.71 g, 34.10 mmol) in methylene chloride (171 mL) was treated with 3,4-dihydro-2H-pyran (4.7 ml, 51.16 mmol) and pyridiniump-toluenesulfonate (857.1 mg, 3.41 mmol). The resulting reaction mixture was stirred at 25° C. for 24 h. The reaction mixture was then washed with a saturated aqueous sodium chloride solution (1×200 mL). The organic layer was dried over magnesium sulfate, filtered, and concentrated in vacuo. Flash chromatography (Merck Silica gel 60, 70-230 mesh, 19/1 petroleum ether/diethyl ether) afforded 2-(3-iodomethyl-cyclopentyloxy)-tetrahydropyran (7.91 g, 75%) as a yellow oil: EI-HRMS m/e calcd for $C_{11}H_{19}IO_2$ (M+) 310.0430. found 310.0433.

A solution of freshly prepared lithium diisopropylamide (23 mL of a 0.31M stock solution, 7.13 mmol) cooled to −78° C. was treated with (3,4-dichloro-phenyl)-acetic acid methyl ester (prepared as in Example 1, 1.42 g, 6.48 mmol) in tetrahydrofuran/1,3-dimethyl-3,4,5,6-tetrahydro-2(1H)-pyrimidinone (16.15 mL, 3:1). The resulting solution was stirred at −78° C. for 45 min. A solution of 2-(3-iodomethyl-cyclopentyloxy)-tetrahydropyran (2.21 g, 7.13 mmol) in 1,3-dimethyl-3,4,5,6-tetrahydro-2(1H)-pyrimidinone (1 mL) was then added. The reaction mixture was stirred at −78° C. for 2 h. The reaction was then warmed to 25° C. and was stirred at 25° C. for 18 h. The reaction mixture was then quenched by the dropwise addition of a saturated aqueous ammonium chloride solution (10 mL). This mixture was poured into water (100 mL) and extracted with methylene chloride 3×50 mL). The organics were washed with a saturated aqueous lithium chloride solution (1×100 mL), dried over sodium sulfate, filtered, and concentrated in vacuo. Flash chromatography (Merck Silica gel 60, 230-400 mesh, 70/30 hexanes/ethyl acetate) afforded 2-(3,4-dichloro-phenyl)-3-[3-(tetrahydro-pyran-2-yloxy)-cyclopentyl]-propionic acid methyl ester (2.12 g, 81.6%) as a clear oil: EI-HRMS m/e calcd for $C_{20}H_{26}Cl_2O_4$ (M+Na)+ 423.1106. found 423.1093.

2-(3,4-Dichloro-phenyl)-3-[3-(tetrahydro-pyran-2-yloxy)-cyclopentyl]-propionic acid methyl ester (1.60 mg, 3.98 mmol) and methylurea (443 mg, 5.98 mmol) in a solution of magnesium methoxide in methanol (7.4 wt. %, 11.4 mL, 7.97 mmol) was heated under reflux at 100° C. for 18 h. The reaction mixture was then concentrated in vacuo and filtered through a plug of celite (100% ethyl acetate as eluent). Flash chromatography (Merck Silica gel 60, 230-400 mesh, 50/50 hexanes/ethyl acetate) afforded 1-{2-(3,4-dichloro-phenyl)-3-[3-(tetrahydro-pyran-2-yloxy)-cyclopentyl]-propionyl}-3-methyl-urea (160.6 mg, 9.1%) as a white solid: mp 62-65° C.; FAB-HRMS m/e calcd for $C_{21}H_{28}Cl_2N_2O_4$ (M+Na)+ 465.1324. found 465.1324.

A solution of 1-{2-(3,4-dichloro-phenyl)-3-[3-(tetrahydro-pyran-2-yloxy)-cyclopentyl]-propionyl}-3-methyl-urea (150.7 mg, 0.33 mmol) in ethanol (3.4 mL) was treated with pyridinium p-toluenesulfonate (8.54 mg, 0.03 mmol). The reaction mixture was heated to 60° C. for 18 h. At this time, the reaction was concentrated in vacuo. Flash chromatography (Merck Silica gel 60, 230-400 mesh, 80/20 methylene chloride/methanol) afforded 1-[2-(3,4-dichloro-phenyl)-3-(3-hydroxy-cyclopentyl)-propionyl]-3-methyl-urea (102.2 mg, 83.7%) as a white solid: mp 82-84° C.; FAB-HRMS m/e calcd for $C_{16}H_{20}Cl_2N_2O_3$ (M+H)+ 359.0929. found 359.0936.

EXAMPLE 36

2-(3,4-Dichloro-phenyl)-3-(3-hydroxy-cyclopentyl)-N-thiazol-2-yl-propionamide

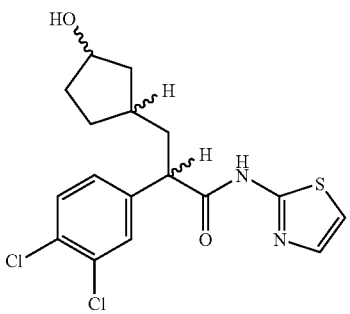

A solution of 2-(3,4-dichloro-phenyl)-3-[3-(tetrahydro-pyran-2-yloxy)-cyclopentyl]-propionic acid methyl ester (prepared as in Example 35, 1.03 g, 2.57 mmol) in methanol (6.4 mL) was treated with Amberlyst® 15 ion exchange resin (77 mg). The resulting reaction mixture was stirred at 25° C. for 16 h and then was heated at 45° C. for 1 h. The reaction mixture was allowed to cool to 25° C., and the resin was then filtered off and then washed well with ethyl acetate. The filtrate was concentrated in vacuo to afford 2-(3,4-dichloro-phenyl)-3-(3-hydroxy-cyclopentyl)-propionic acid methyl ester (807.7 mg, 99%) as a yellow oil which was used without further purification.

A mixture of 2-(3,4-dichloro-phenyl)-3-(3-hydroxy-cyclopentyl)-propionic acid methyl ester (25 mg, 0.08 mmol) and 2-aminothiazole (9.4 mg, 0.09 mmol) in a solution of magnesium methoxide in methanol (7.4 wt. %, 0.22 mL, 0.15 mmol) was heated to 110° C. for 18 h. At this time, the reaction mixture was cooled to 25° C. and then filtered through a pad of celite (methylene chloride as eluent). The filtrate was washed with a 1N aqueous hydrochloric acid solution. The organics were dried over sodium sulfate, filtered and then concentrated in vacuo. Flash chromatography (Merck Silica gel 60, 230-400 mesh, 75/25 ethyl acetate/hexanes) afforded 2-(3,4-dichloro-phenyl)-3-(3-hydroxy-cyclopentyl)-N-thiazol-2-yl-propionamide (16.4 mg, 54%) as light tan oil: EI-HRMS m/e calcd for $C_{17}H_{18}Cl_2N_2O_2S$ (M+H)+ 385.0537. found 385.0542.

EXAMPLE 37

3-(3-Hydroxy-cyclopentyl)-2-(4-methanesulfonyl-phenyl)-N-thiazol-2-yl-propionamide

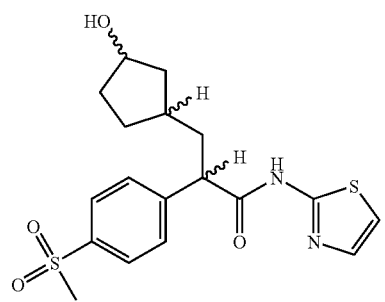

A solution of diisopropylamine (810 μL, 5.78 mmol) in dry tetrahydrofuran (4.5 mL) and 1,3-dimethyl-3,4,5,6-tetrahydro-2(1H)-pyrimidinone (1.5 mL) cooled to −78° C. was treated with a 2.5M solution of n-butyllithium in hexanes (2.3 mL, 5.78 mmol). The reaction mixture was stirred at −78° C. for 30 min and then treated with a solution of (4-methanesulfonyl-phenyl)-acetic acid methyl ester (prepared as in Example 8, 1.10 g, 4.82 mmol) in dry tetrahydrofuran (4.5 mL) and 1,3-dimethyl-3,4,5,6-tetrahydro-2 (1H)-pyrimidinone (1.5 mL). The resulting reaction mixture was allowed to stir at −78° C. for 1 h and then the reaction mixture was treated with a solution of 2-(3-iodomethyl-cyclopentyloxy)-tetrahydropyran (prepared as in Example 35, 1.94 g, 6.26 mmol) in a small amount of dry tetrahydrofuran. The reaction mixture was stirred at −78° C. for 10 min and then allowed to warm to 25° C., where it was stirred for 3 d. The reaction mixture was quenched with water (50 mL) and then concentrated in vacuo to remove tetrahydrofuran. The aqueous residue was further diluted with water (100 mL) and then extracted with ethyl acetate 3×100 mL). The combined organic extracts were dried over magnesium sulfate, filtered, and concentrated in vacuo. Flash chromatography (Merck Silica gel 60, 70-230 mesh, 7/3 hexanes/ethyl acetate) afforded the 2-(4-methanesulfonyl-phenyl)-3-[3-(tetrahydropyran-2-yloxy)-cyclopentyl]-propionic acid methyl ester (1.07 g, 54%) as a yellow oil: FAB-HRMS m/e calcd for $C_{21}H_{30}O_6S$ (M+H)$^+$ 411.1841. found 411.1851.

2-Aminothiazole (259 mg, 2.58 mmol) and 2-(4-methanesulfonyl-phenyl)-3-[3-(tetrahydropyran-2-yloxy)-cyclopentyl]-propionic acid methyl ester (1.06 g, 2.58 mmol) were treated with a solution of magnesium methoxide in methanol (7.4 wt. %, 14.76 mL, 10.32 mmol). The reaction mixture was then concentrated in vacuo to approximately one-half the volume of methanol. The resulting reaction mixture was heated under reflux for 24 h. The reaction mixture was allowed to cool to 25° C. and then filtered through a pad of celite. The pad of celite was washed well with ethyl acetate until the washings indicated the absence of product by thin layer chromatography. The filtrate was then washed with a saturated aqueous sodium chloride solution, dried over magnesium sulfate, filtered, and concentrated in vacuo. Flash chromatography (Merck Silica gel 60, 230-400 mesh, 1/2 hexanes/ethyl acetate) afforded 2-(4-methanesulfonyl-phenyl)-3-[3-(tetrahydropyran-2-yloxy)-cyclopentyl]-N-thiazol-2-yl-propionamide (494 mg, 40%) as a yellow foam: mp 68-70° C. (foam to gel); FAB-HRMS m/e calcd for $C_{23}H_{30}N_2O_5S_2$ (M+H)$^+$ 479.1674. found 479.1666.

A solution of 2-(4-methanesulfonyl-phenyl)-3-[3-(tetrahydropyran-2-yloxy)-cyclopentyl]-N-thiazol-2-yl-propionamide (450 mg, 0.94 mmol) in ethanol (9.4 mL) was treated with pyridinium p-toluenesulfonate (24 mg, 0.094 mmol). The resulting reaction mixture was heated at 60° C. for 4 h. The reaction mixture was allowed to cool to 25° C. and then concentrated in vacuo. The resulting yellow residue was diluted with ethyl acetate (100 mL) and then washed with a saturated aqueous sodium chloride solution. The organic layer was dried over magnesium sulfate, filtered, and concentrated in vacuo. Flash chromatography (Merck Silica gel 60, 230-400 mesh, 1/3 to 1/7 hexanes/ethyl acetate) afforded the 3-(3-hydroxy-cyclopentyl)-2-(4-methanesulfonyl-phenyl)-N-thiazol-2-yl-propionamide (318 mg, 86%) as a white foam: mp 69-72° C.; FAB-HRMS m/e calcd for $C_{18}H_{22}N_2O_4S_2$ (M+H)$^+$ 395.1099. found 395.1091.

EXAMPLE 38

2(R)-(3-Chloro-4-methanesulfonyl-phenyl)-3-(3-hydroxy-cyclopentyl)-N-pyrazin-2-yl-propionamide

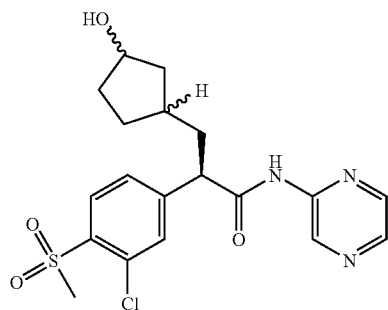

A solution of 1,1,1,3,3,3-hexamethyldisilazane (3.75 mL, 17.24 mmol) in freshly distilled tetrahydrofuran (50 mL) was treated slowly with a 2.3M solution of n-butyllithium in hexanes (7.0 mL, 16.1 mmol) at −45° C. The resulting reaction solution was stirred at −40° C. for 45 min and then treated slowly with a solution of 2-(3-chloro-4-methylsulfanyl-phenyl)-N-[2(R)-hydroxy-1(R)-methyl-2(R)-phenyl-ethyl]-N-methyl-acetamide (prepared as in Example 30, 2.5 g, 6.87 mmol) in tetrahydrofuran (10 mL) via a cannula. A yellow solution was obtained, and the reaction was allowed to warm to 0° C., where it was stirred for 30 min. This reaction solution was cooled to −50° C. and treated with 1,3-dimethyl-3,4,5,6-tetrahydro-2(1H)-pyrimidinone (5 mL) followed by the dropwise addition of a solution of 2-(3-iodomethyl-cyclopentyloxy)-tetrahydropyran (prepared as in Example 35, 3.2 g, 10.3 mmol) in tetrahydrofuran (10 mL). After the addition, the reaction solution was warmed to 0° C., where it was stirred for 2 h, and then warmed to 25° C., where it was stirred for an additional 2 h. The reaction solution was diluted with methylene chloride (100 mL) and washed with a saturated aqueous sodium chloride solution (100 mL). The organic layer was separated, dried over magnesium sulfate, filtered, and concentrated in vacuo. Flash chromatography (Merck Silica gel 60, 70-230 mesh, 40-60% ethyl acetate/hexanes) afforded 2(R)-(3-chloro-4-methylsulfanyl-phenyl)-N-(2(R)-hydroxy-1(R)-methyl-2(R)-phenyl-ethyl)-N-methyl-3-[3-(tetrahydro-pyran-2-yloxy)-cyclopentyl]-propionamide (3.4 g, 90.7%) as a white solid.

A solution of 2(R)-(3-chloro-4-methylsulfanyl-phenyl)-N-(2(R)-hydroxy-1(R)-methyl-2(R)-phenyl-ethyl)-N-methyl-3-[3-(tetrahydro-pyran-2-yloxy)-cyclopentyl]-propionamide (0.96 g, 1.758 mmol) in dioxane (20 mL) was treated with a 9N aqueous sulfuric acid solution (1.5 mL). The resulting reaction solution was heated under reflux for 15 h. In another flask, a solution of 2(R)-(3-chloro-4-methylsulfanyl-phenyl)-N-(2(R)-hydroxy-1(R)-methyl-2 (R)-phenyl-ethyl)-N-methyl-3-[3-(tetrahydro-pyran-2-yloxy)-cyclopentyl]-propionamide (1 g, 1.83 mmol) in dioxane (20 mL) and a 9N aqueous sulfuric acid solution (1.5 mL) was heated under reflux for 7 h. The two reactions were combined, diluted with methylene chloride (100 mL), and washed with a saturated aqueous sodium chloride solution (100 mL). The organic layer was separated, dried over magnesium sulfate, filtered, and concentrated in vacuo. Flash chromatography (Merck Silica gel 60, 70-230 mesh, 8-10% methanol/methylene chloride) afforded 2(R)-(3-chloro-4-methylsulfanyl-phenyl)-3-(3-hydroxy-cyclopentyl)-propionic acid (496 mg 43.9%) as an off-white foam.

A solution of 2(R)-(3-chloro-4-methylsulfanyl-phenyl)-3-(3-hydroxy-cyclopentyl)-propionic acid (350 mg, 1.11 mmol) in formic acid (35 mL) was treated with a 30% aqueous hydrogen peroxide solution (1 mL, 7.89 mmol) at 25° C. The mixture was then allowed to stir at 25° C. overnight. The solvent was evaporated in vacuo. The resulting residue was azeotroped with toluene to remove water and then co-evaporated with N,N-dimethylformamide to remove formic acid to afford crude 2(R)-(3-chloro-4-methanesulfonyl-phenyl)-3-(3-formyloxy-cyclopentyl)-propionic acid (430 mg, 103%) as an off-white solid.

A solution of 2(R)-(3-chloro-4-methanesulfonyl-phenyl)-3-(3-formyloxy-cyclopentyl)-propionic acid (380 mg, 1.01 mmol) in toluene (10 mL) at 0° C. was treated with N,N-dimethylformamide (0.008 mL) followed by a 2.0M solution of oxalyl chloride in methylene chloride (0.75 mL). The reaction mixture was allowed to stir at 0° C. for 30 min and at 25° C. for 1.5 h. It appeared that a thick oil in the bottom of the reaction flask never solubilized. Additional methylene chloride (10 mL) was added at 25° C. followed by N;N-dimethylformamide (0.002 mL) and oxalyl chloride (0.3 mL). The reaction mixture was stirred at 25° C. for an additional 45 min and then concentrated in vacuo. The residue was dissolved in dry tetrahydrofuran (5 mL) and cooled to 0° C. This cold solution was then treated with a solution of 2-aminopyrazine (142 mg, 1.5 mmol) and pyridine (0.121 mL, 1.5 mmol) in dry tetrahydrofuran (5 mL) via a cannula. The resulting reaction mixture was stirred at 0° C. for 1 h and then diluted with methylene chloride (100 mL). The organic layer was successively washed with a 1M aqueous citric acid solution (2×100 mL), a saturated sodium bicarbonate solution 1×100 mL), and a saturated sodium chloride solution 1×100 mL). The organics were dried over magnesium sulfate, filtered, and concentrated in vacuo to afford formic acid 3-[2(R)-(3-chloro-4-methanesulfonyl-phenyl)-2-(pyrazin-2-ylcarbamoyl)-ethyl]-cyclopentyl ester (375 mg, 82%) as an off-white solid.

To a solution of formic acid 3-[2(R)-(3-chloro-4-methanesulfonyl-phenyl)-2-(pyrazin-2-ylcarbamoyl)-ethyl]-cyclopentyl ester (375 mg, 0.83 mmol) in methanol (50 mL) at 0° C. was bubbled ammonia gas for 15 min. The resulting reaction solution was stirred at 0° C. for 15 min. The solvent was removed in vacuo. Flash chromatography (Merck Silica gel 60, 70-230 mesh, 1-5% methanol/methylene chloride) afforded 2(R)-(3-chloro-4-methanesulfonyl-phenyl)-3-(3-hydroxy-cyclopentyl)-N-pyrazin-2-yl-propionamide (260 mg, 62.5%) as an off-white solid.

EXAMPLE 39

2-(3,4-Dichloro-phenyl)-3-(3-methoxy-cyclopentyl)-N-thiazol-2-yl-propionamide

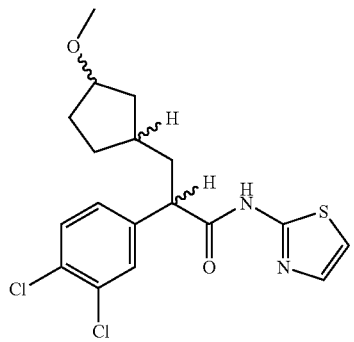

A solution of 2-(3,4-dichloro-phenyl)-3-(3-hydroxy-cyclopentyl)-propionic acid methyl ester (prepared as in Example 36, 194.1 mg, 0.61 mmol), silver carbonate (320.6 mg, 1.16 mmol), silver tetrafluoroborate (131.0 mg, 0.67 mmol), and iodomethane (72 μL, 1.16 mmol) in acetonitrile (6.1 mL) was stirred at 25° C. for 48 h. The resulting reaction mixture was then heated under reflux for 24 h. The reaction mixture was then filtered through a pad of celite, and the celite pad was washed well with ethyl acetate. The filtrate was concentrated in vacuo. Flash chromatography (Merck Silica gel 60, 230-400 mesh, 10% ethyl acetate/hexanes) afforded 2-(3,4-dichloro-phenyl)-3-(3-methoxy-cyclopentyl)-propionic acid methyl ester (68.8 mg, 34%) as a yellow oil which was used without further purification.

2-(3,4-Dichloro-phenyl)-3-(3-methoxy-cyclopentyl)-propionic acid methyl ester (118.3 mg, 0.36 mmol) and 2-aminothiazole (35.8 mg, 0.36 mmol) were treated with a solution of magnesium methoxide in methanol (7.4 wt. % , 2.6 mL, 1.79 mmol). The resulting reaction mixture was then heated under reflux for 30 h. The reaction mixture was allowed to cool to 25° C. and then filtered through celite. The celite was thoroughly washed with ethyl acetate, and the filtrate was concentrated in vacuo. Flash chromatography (Merck Silica gel 60, 230-400 mesh, 40% ethyl acetate/hexanes) afforded the 2-(3,4-dichloro-phenyl)-3-(3-methoxy-cyclopentyl)-N-thiazol-2-yl-propionamide (9.6 mg, 7%) as a white glass: (ES)$^+$-HRMS m/e calcd for $C_{18}H_{20}Cl_2N_2O_2S$ (M+H)$^+$ 399.0696. found 399.0700.

EXAMPLE 40

Acetic acid 3-[2-(3,4-dichloro-phenyl)-2-(thiazol-2-ylcarbamoyl)-ethyl]-cyclopentyl ester

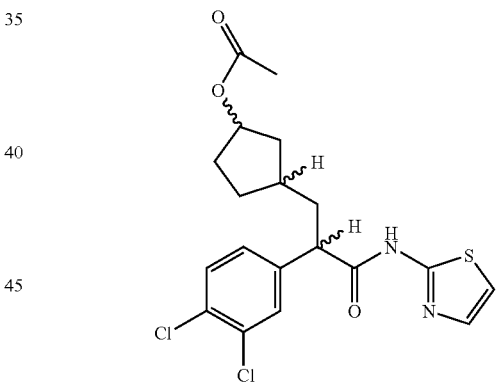

A solution of 2-(3,4-dichloro-phenyl)-3-(3-hydroxy-cyclopentyl)-N-thiazol-2-yl-propionamide (prepared as in Example 36, 147.8 mg, 0.38 mmol) and acetic anhydride (72 μL, 0.77 mmol) in pyridine (2 mL) and methylene chloride (1 mL) was stirred at 25° C. for 20 h. The resulting reaction mixture was concentrated in vacuo. Since the reaction did not go to completion, the residue was re-dissolved in pyridine (1.8 mL) and acetic anhydride (1.4 mL, 14.84 mmol) and then stirred at 25° C. for an additional 7 h. The reaction mixture was concentrated in vacuo and then diluted with ethyl acetate (50 mL). The organic layer was washed with a 1N aqueous hydrochloric acid solution 3×50 mL), water (50 mL), and a saturated aqueous sodium chloride solution (50 mL), dried over sodium sulfate, filtered, and concentrated in vacuo. Flash chromatography (Merck Silica gel 60, 230-400 mesh, 35% ethyl acetate/hexanes) afforded acetic acid 3-[2-(3,4-dichloro-phenyl)-2-(thiazol-2-ylcarbamoyl)-ethyl]-cyclopentyl ester (80.8 mg, 49%) as a white solid: mp 49-52° C.; (ES)+-HRMS m/e calcd for $C_{19}H_{20}Cl_2N_2O_3S$ (M+H)+ 427.0645. found 427.0648.

EXAMPLE 41

2-(3,4-Dichloro-phenyl)-3-(3-fluoro-cyclopentyl)-N-thiazol-2-yl-propionamide

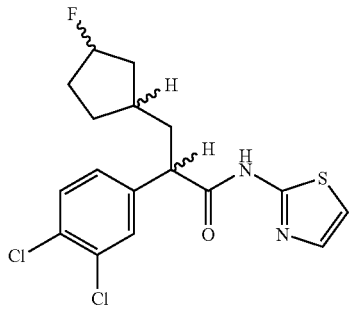

A solution of 2-(3,4-dichloro-phenyl)-3-(3-hydroxy-cyclopentyl)-propionic acid methyl ester (prepared as in Example 36, 180 mg, 0.56 mmol) in methylene chloride (0.28 mL) was treated with diethylaminosulfur trifluoride (0.11 mL, 0.85 mmol). The resulting mixture was stirred at 25° C. for 18 h. At this time, the reaction was diluted with water (50 mL). This solution was extracted with methylene chloride 3×30 mL). The organics were dried over sodium sulfate, filtered, and concentrated in vacuo. Flash chromatography (Merck Silica gel 60, 230-400 mesh, 50/50 hexanes/ethyl acetate) afforded 2-(3,4-dichloro-phenyl)-3-(3-fluoro-cyclopentyl)-propionic acid methyl ester (71.2 mg, 39.3%) as a light yellow oil.

A mixture of 2-(3,4-dichloro-phenyl)-3-(3-fluoro-cyclopentyl)-propionic acid methyl ester (70 mg, 0.24 mmol) and 2-aminothiazole (26.3 mg, 0.26 mmol) in a solution of magnesium methoxide in methanol (7.4 wt. % , 0.63 mL, 0.43 mmol) was heated to 110° C. for 18 h. At this time, the reaction mixture was cooled to 25° C. and then concentrated in vacuo. Flash chromatography (Merck Silica gel 60, 230-400 mesh, 70/30 hexanes/ethyl acetate) afforded 2-(3, 4-dichloro-phenyl)-3-(3-fluoro-cyclopentyl)-N-thiazol-2-yl-propionamide (2.3 mg, 2.7%) as a light yellow oil: EI-HRMS m/e calcd for $C_{17}H_{17}Cl_2N_2OS$ (M+H)+ 387.0496. found 387.0499.

EXAMPLE 42

1-[2-(3,4-Dichloro-phenyl)-3-(3-oxo-cyclopentyl)-propionyl]-3-methyl-urea

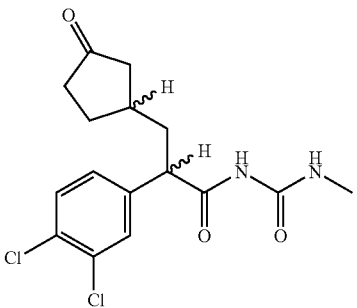

A solution of 1-[2-(3,4-dichloro-phenyl)-3-(3-hydroxy-cyclopentyl)-propionyl]-3-methyl-urea (prepared as in Example 35, 60.5 mg, 0.17 mmol) in methylene chloride (1.68 mL) was treated with pyridinium chlorochromate (20 wt. % on basic alumina, 218 mg, 0.20 mmol). The reaction mixture was stirred at 25° C. for 4 h. At this time, the reaction was filtered through a plug of celite (ethyl acetate as eluent). The filtrate was concentrated in vacuo. Flash chromatography (Merck Silica gel 60, 230-400 mesh, 90/10 methylene chloride/methanol) afforded 1-[2-(3,4-dichloro-phenyl)-3-(3-oxo-cyclopentyl)-propionyl]-3-methyl-urea (45.8 mg, 76.1%) as a white solid: mp 70-74° C.; FAB-HRMS m/e calcd for $C_{16}H_{18}Cl_2N_2O_3$ (M+H)+ 357.0773. found 357.0768.

EXAMPLE 43

2-(3,4-Dichloro-phenyl)-3-(3-oxo-cyclopentyl)-N-thiazol-2-yl-propionamide

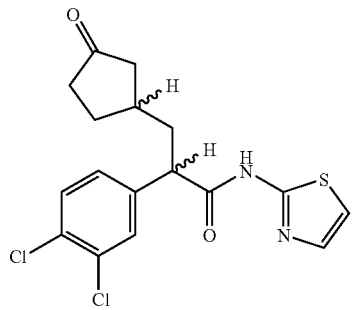

A solution of 3-iodomethyl-cyclopentanone (prepared as in Example 35, 23.47 g, 0.10 mol), 1,3-propanediol (39.86 g, 0.52 mol), trimethyl orthoformate (13.61 g, 0.1257 mol), and p-toluenesulfonic acid monohydrate in benzene (524 mL) was heated under reflux for 6 h. The reaction was cooled to 25° C., diluted with water (1 L), and extracted with diethyl ether (2×400 mL). The organic layers were dried over magnesium sulfate, filtered, and concentrated in vacuo. Flash chromatography (Merck Silica gel 60, 70-230 mesh, 15% diethyl ether/petroleum ether) afforded 2-iodomethyl-6,10-dioxa-spiro[4.5]decane (18.77 g, 63%) as a yellow oil.

A solution of diisopropylamine (2.5 mL, 17.80 mmol) in dry tetrahydrofuran (26 mL) and 1,3-dimethyl-3,4,5,6-tetrahydro-2(1H)-pyrimidinone (8 mL) was cooled to −78° C. under nitrogen and then treated with a 2.5M solution of n-butyllithium in hexanes (7.1 mL, 17.80 mmol). The reaction mixture was stirred at −78° C. for 45 min and then treated dropwise with a solution of (3,4-dichloro-phenyl)-acetic acid methyl ester (prepared as in Example 1, 3.00 g, 13.69 mmol) in dry tetrahydrofuran (26 mL) and 1,3-dimethyl-3,4,5,6-tetrahydro-2(1H)-pyrimidinone (8 mL). The reaction mixture turned dark yellow in color and was allowed to stir at −78° C. for 10 min and then at 0° C. for 30 min. The reaction mixture was then cooled to −78° C., at which time, a solution of 2-iodomethyl-6,10-dioxa-spiro [4.5]decane (5.79 g, 20.54 mmol) in dry tetrahydrofuran (13 mL) and 1,3-dimethyl-3,4,5,6-tetrahydro-2(1H)-pyrimidinone (8 mL) was added dropwise. The reaction mixture stirred at −78° C. for 15 min, and was then allowed to warm to 25° C., where it was stirred for 20 h. The reaction mixture was quenched with a saturated aqueous ammonium chloride solution (100 mL) and then concentrated in vacuo to remove tetrahydrofuran. The aqueous residue was extracted with ethyl acetate (2×150 mL). The combined organic extracts were washed with a saturated aqueous lithium chloride solution (2×200 mL), water (200 mL) and a saturated aqueous sodium chloride solution (200 mL), dried over sodium sulfate, filtered, and concentrated in vacuo. Flash chromatography (Merck Silica gel 60, 230-400 mesh, 15% ethyl acetate/hexanes) afforded 2-(3,4-dichloro-phenyl)-3-(6,10-dioxa-spiro[4.5]dec-2-yl)-propionic acid methyl ester (3.92 g, 77%) as a yellow oil.

2-(3,4-Dichloro-phenyl)-3-(6,10-dioxa-spiro[4.5]dec-2-yl)-propionic acid methyl ester (1.00 g, 2.68 mmol) was treated with a solution of magnesium methoxide in methanol (7.4 wt. %, 19 mL, 13.39 mmol), The reaction mixture was then treated with 2-aminothiazole (348.7 mg, 3.48 mmol). The resulting reaction mixture was then heated under reflux for 28 h. The reaction mixture was allowed to cool to 25° C. and then filtered through celite. The celite was thoroughly washed with ethyl acetate, and the filtrate was concentrated in vacuo. Flash chromatography (Merck Silica gel 60, 230-400 mesh, 25-50% ethyl acetate/hexanes) afforded crude 2-(3,4-dichloro-phenyl)-3-(6,10-dioxa-spiro[4.5]dec-2-yl)-N-thiazol-2-yl-propionamide (768.5 mg) as a yellow oil which was used without further purification.

A solution of crude 2-(3,4-dichloro-phenyl)-3-(6,10-dioxa-spiro[4.5]dec-2-yl)-N-thiazol-2-yl-propionamide (768.5 mg, 1.74 mmol) in tetrahydrofuran (8.7 mL) and a 5% aqueous hydrochloric acid solution (3.9 mL) was stirred at 25° C. for 64 h. The resulting reaction solution was concentrated in vacuo to remove tetrahydrofuran and then diluted with ethyl acetate (100 mL). The organic layer was washed with a 1% aqueous hydrochloric acid solution (50 mL), water (50 mL) and a saturated aqueous sodium chloride solution (50 mL), dried over sodium sulfate, filtered, and concentrated in vacuo. Flash chromatography (Merck Silica gel 60, 230-400 mesh, 50% ethyl acetate/hexanes) afforded 2-(3,4-dichloro-phenyl)-3-(3-oxo-cyclopentyl)-N-thiazol-2-yl-propionamide (481.9 mg, 47% over 2 steps) as a white solid: mp 146-148° C.; (ES)$^+$-HRMS m/e calcd for $C_{17}H_{16}C_{12}N_2O_2S$ (M+H)$^+$ 383.0383. found 383.0385.

EXAMPLE 44

2-(4-Methanesulfonyl-phenyl)-3-(3-oxo-cyclopentyl)-N-thiazol-2-yl-propionamide

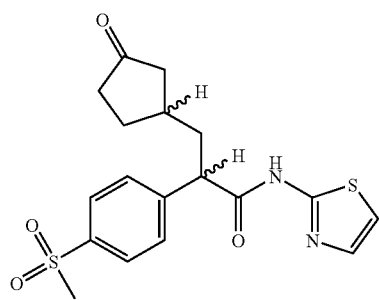

A solution of 3-(3-hydroxy-cyclopentyl)-2-(4-methanesulfonyl-phenyl)-N-thiazol-2-yl-propionamide (prepared as in Example 37, 155 mg, 0.393 mmol) in methylene chloride (3 mL) was treated with pyridinium chlorochromate (20 wt. % on basic alumina, 508 mg, 0.471 mmol). The resulting reaction mixture was stirred at 25° C. for 3 h, at which time, thin layer chromatography indicated a small amount of the 3-(3-hydroxy-cyclopentyl)-2-(4-methanesulfonyl-phenyl)-N-thiazol-2-yl-propionamide. The reaction mixture was then treated with an additional amount of pyridinium chlorochromate (20 wt. % on basic alumina, 127 mg, 0.118 mmol). The reaction mixture was allowed to stir at 25° C. for 1 h and then filtered through a pad of celite. The pad of celite was washed well with ethyl acetate until the washings indicated the absence of product by thin layer chromatography. The filtrate was then concentrated in vacuo. Flash chromatography (Merck Silica gel 60, 230-400 mesh, 1/3 hexanes/ethyl acetate to 100% ethyl acetate) afforded 2-(4-methanesulfonyl-phenyl)-3-(3-oxo-cyclopentyl)-N-thiazol-2-yl-propionamide (46 mg, 30%) as a white foam: mp 94-97° C.; FAB-HRMS m/e calcd for $C_{18}H_{20}N_2O_4S_2$ (M+H)$^+$ 393.0943. found 393.0948.

EXAMPLE 45

2-(3-Chloro-4-methanesulfonyl-phenyl)-3-(3-oxo-cyclopentyl)-N-pyrazin-2-yl-propionamide

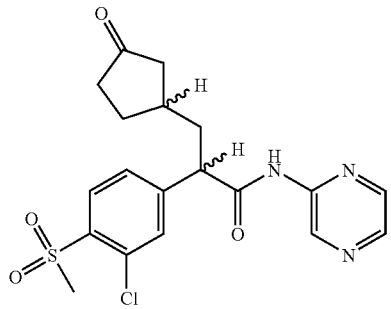

A solution of diisopropylamine (1.9 mL, 13.64 mmol) in dry tetrahydrofuran (19.5 mL) and 1,3-dimethyl-3,4,5,6-tetrahydro-2(1H)-pyrimidinone (6.5 mL) cooled to −78° C. under nitrogen was treated with a 2.5M solution of n-butyllithium in hexanes (5.5 mL, 13.64 mmol). The reaction mixture was stirred at −78° C. for 45 min and then treated dropwise with a solution of (3-chloro-4-methylsulfanyl-phenyl)-acetic acid methyl ester (prepared as in Example 4, 2.42 g, 10.49 mmol) in dry tetrahydrofuran (19.5 mL) and 1,3-dimethyl-3,4,5,6-tetrahydro-2(1H)-pyrimidinone (6.5 mL). The reaction mixture turned bright yellow. The reaction mixture was allowed to stir at −78° C. for 15 min, then at 0° C. for an additional 30 min, and then re-cooled to −78° C. At this point, a solution of 2-iodomethyl-6,10-dioxa-spiro [4.5]decane (prepared as in Example 43, 3.85 g, 13.64 mmol) in dry tetrahydrofuran (10 ML) and 1,3-dimethyl-3, 4,5,6-tetrahydro-2(1H)-pyrimidinone (3 mL) was added dropwise. The reaction mixture stirred at −78° C. for 30 min and was then allowed to warm to 25° C., where it was stirred for 24 h. The reaction mixture was concentrated in vacuo to remove tetrahydrofuran. The aqueous residue was diluted with ethyl acetate (200 mL), and the organic layer was washed with a saturated aqueous lithium chloride solution (2×200 mL), water (200 mL), and a saturated aqueous sodium chloride solution. The organic layer was dried over magnesium sulfate, filtered, and concentrated in vacuo. Flash chromatography (Merck Silica gel 60, 230-400 mesh, 25% ethyl acetate/hexanes) afforded the 2-(3-chloro-4-methylsulfanyl-phenyl)-3-(6,10-dioxa-spiro[4.5]dec-2-yl)-propionic acid methyl ester (2.27 g, 56%) as a yellow oil: EI-HRMS m/e calcd for $C_{19}H_{25}ClO_4S$ (M)$^+$ 384.1162. found 384.1181.

A solution of 2-(3-chloro-4-methylsulfanyl-phenyl)-3-(6,10-dioxa-spiro[4.5]dec-2-yl)-propionic acid methyl ester (1.18 g, 3.07 mmol) in methylene chloride (8 mL) cooled to 0° C. was slowly treated with a mixture of 3-chloroperoxybenzoic acid (~70%, 1.51 g based on 70%, 6.13 mmol) and sodium bicarbonate (1.03 g, 12.26 mmol) in methylene chloride (8 mL). The thick reaction mixture was diluted with methylene chloride (8 mL) and was then allowed to warm to 25° C., where it was stirred for 4 h. The reaction mixture was diluted with methylene chloride (200 mL) and water (200 mL). The organic phase was cooled down to 0° C. and then slowly treated with a saturated aqueous sodium bisulfite solution (200 mL). The organic layer was washed with a saturated aqueous sodium bicarbonate solution (100 mL), water (100 mL), and a saturated aqueous sodium chloride solution (100 mL), dried over sodium sulfate, filtered, and concentrated in vacuo. Flash chromatography (Merck Silica gel 60, 70-230 mesh, 50% ethyl acetate/hexanes) afforded 2-(3-chloro-4-methanesulfonyl-phenyl)-3-(6,10-dioxa-spiro [4.5]dec-2-yl)-propionic acid methyl ester (1.22 g, 95%) as a colorless oil: EI-HRMS m/e calcd for $C_{19}H_{25}ClO_6S$ $(M)^+$ 416.1060. found 416.1054.

A solution of 2-(3-chloro-4-methanesulfonyl-phenyl)-3-(6,10-dioxa-spiro[4.5]dec-2-yl)-propionic acid methyl ester (1.21 g, 2.90 mmol) in tetrahydrofuran (14.5 mL) was treated with a 5% aqueous hydrochloric acid solution (6.4 mL) and stirred at 25° C. for 29 h. The reaction was then concentrated in vacuo to remove tetrahydrofuran. The resulting aqueous residue was diluted with water (200 mL) and extracted with ethyl acetate (2×100 mL). The combined organic layers were dried over sodium sulfate, filtered, and concentrated in vacuo. Flash chromatography (Merck Silica gel 60, 70-230 mesh, 50% ethyl acetate/hexanes) afforded 2-(3-chloro-4-methanesulfonyl-phenyl)-3-(3-oxo-cyclopentyl)-propionic acid methyl ester (1.03 g, 99%) as a colorless oil: EI-HRMS m/e calcd for $C_{16}H_{19}ClO_5S$ $(M)^+$ 358.0642. found 358.0630.

A solution of 2-(3-chloro-4-methanesulfonyl-phenyl)-3-(3-oxo-cyclopentyl)-propionic acid methyl ester (1.02 g, 2.84 mmol) in methanol (7.1 mL) was treated with a 1N aqueous sodium hydroxide solution (6.0 µL, 6.0 mmol). The reaction mixture was stirred at 25° C. for 16 h. The reaction mixture was then concentrated in vacuo to remove methanol. The resulting aqueous residue was diluted with water (100 mL) and acidified to pH=3 with a 1N aqueous hydrochloric acid solution then extracted with ethyl acetate (2×150 mL). The combined organic layers were washed with a saturated aqueous sodium chloride solution (100 mL), dried over sodium sulfate, filtered, and concentrated in vacuo. The resulting yellow oily solid was triturated with ethyl acetate/petroleum ether to afford 2-(3-chloro-4-methanesulfonyl-phenyl)-3-(3-oxo-cyclopentyl)-propionic acid (800.0 mg, 82%) as a white solid: mp 164-167° C.; $(ES)^+$-HRMS m/e calcd for $C_{15}H_{17}ClO_5S$ $(M+H)^+$ 345.0558. found 345.0561.

A solution of 2-(3-chloro-4-methanesulfonyl-phenyl)-3-(3-oxo-cyclopentyl)-propionic acid (594.8 mg, 1.725 mmol) in methylene chloride (8.6 mL) and N,N-dimethylformamide (2 drops) cooled to 0° C. was treated with oxalyl chloride (226 µL, 2.587 mmol). The reaction mixture was stirred at 0° C. for 15 min and then stirred at 25° C. for 2 h. The reaction mixture was concentrated in vacuo to afford a red oil. This red oil was dissolved in tetrahydrofuran (4.03 mL), cooled to 0° C., and then slowly treated with a solution of 2-aminopyrazine (246.1 mg, 2.587 mmol) and pyridine (209 µL, 2.587 mmol) in tetrahydrofuran (4.3 mL). The resulting reaction mixture was stirred at 0° C. for 15 min and then stirred at 25° C. for 2 h. The reaction mixture was quenched with a 1N aqueous citric acid solution (20 mL) and then extracted with ethyl acetate (2×100 mL). The combined organic layers were washed with a saturated aqueous sodium bicarbonate solution (2×100 mL) and a saturated aqueous sodium chloride solution (100 mL), dried over sodium sulfate, filtered, and concentrated in vacuo. Flash chromatography (Merck Silica gel 60, 230-400 mesh, 80% ethyl acetate/hexanes) afforded 2-(3-chloro-4-methanesulfonyl-phenyl)-3-(3-oxo-cyclopentyl)-N-pyrazin-2-yl-propionamide (207.3 mg, 28%) as a pale yellow foam: mp 93-96° C. (foam to gel); $(ES)^+$-HRMS m/e calcd for $C_{19}H_{20}ClN_3O_4S$ $(M+H)^+$422.0936. found 422.0938.

EXAMPLE 46

2(R)-(3-Chloro-4-methanesulfonyl-phenyl)-3-(3-oxo-cyclopentyl)-N-pyrazin-2-yl-propionamide

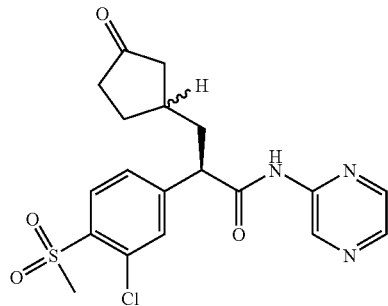

A solution of 2(R)-(3-chloro-4-methanesulfonyl-phenyl)-3-(3-hydroxy-cyclopentyl)-N-pyrazin-2-yl-propionamide (prepared as in Example 38, 60 mg, 0.142 mmol) in methylene chloride (10 mL) was treated with Dess-Martin periodinane (132.5 mg, 0.312 mmol). The reaction mixture was stirred at 25° C. for 2 h. The reaction mixture was then diluted with methylene chloride (10 mL) and washed with a 1M aqueous citric acid solution (10 mL). The pH of the aqueous layer was adjusted to 5. The aqueous layer was then extracted with methylene chloride (20 mL). The combined organic layers were dried over magnesium sulfate, filtered, and concentrated in vacuo. Flash chromatography (Merck Silica gel 60, 70-230 mesh, 50-100% ethyl acetate/hexanes) afforded 2(R)-(3-chloro-4-methanesulfonyl-phenyl)-3-(3-oxo-cyclopentyl)-N-pyrazin-2-yl-propionamide (45 mg, 75%) as an off-white solid.

EXAMPLE 47

2(R)-(3-Chloro-4-methanesulfonyl-phenyl)-3-((S)-3-oxo-cyclopentyl)-N-pyrazin-2-yl-propionamide

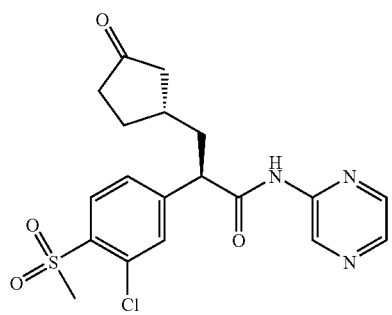

Step 1

A solution of (S,S)-hydrobenzoin (10.0 g, 46.7 mmol), pyridinium p-toluene sulfonate (1.4 g, 5.6 mmol), 2-cyclopentene-1-one (20 mL, 238.7 mmol) and cyclohexane (200 mL) was heated under reflux for 4 h with a Dean-Stark trap to remove water formed during the reaction. The mixture was then cooled in an ice bath for 20 min, and the insolubles were filtered off through filter aid. The resulting solution was washed with a 10% aqueous potassium bicarbonate solution (2×25 mL) and water (2×25 mL), and then dried over anhydrous sodium sulfate. The dried solution was passed through a pad of silica gel 60 (26 g of 230-400 mesh). The pad was further eluted with additional hexanes (475 mL). The resulting solution was concentrated in vacuo to afford 2(S),3(S)-diphenyl-1,4-dioxa-spiro[4.4]non-6-ene (10.55 g, 81%) as a white solid.

Step 2

A solution of 1,2-dichloroethane (85 mL) and diethyl zinc (6.5 mL, 63.4 mmol) cooled to −15° C. under a nitrogen atmosphere was treated with iodochloromethane (8.9 mL, 122 mmol), via syringe, at such a rate as to allow the temperature to rise to −7° C. (over about 5 min). The mixture was stirred with cooling for an additional 15 min at −7° C. to −13° C. until there was no further exotherm. The reaction was then stirred at ~0° C. for 10 min, then re-cooled to −35° C. At this time, a solution of 2(S),3(S)-diphenyl-1,4-dioxa-spiro[4.4]non-6-ene (8.5 g, 30.5 mmol) in 1,2-dichloroethane (51 mL) was added via syringe over 10 min. The reaction temperature increased to −26° C. during the addition. The reaction was then stirred at −26° C. for 30 min. At this time, the reaction was re-cooled to −35° C. and a 10% aqueous potassium bicarbonate solution (17 mL) was added dropwise while maintaining the temperature below −12° C. The cooling bath was then removed, and the reaction was allowed to warm to 25° C., where it was stirred for 1.5 h. The liquid was decanted, and the white pasty residue was slurried with tert-butyl methyl ether (2×100 ml). The supernatants were decanted, and the combined organic solution was washed with a 10% aqueous potassium bicarbonate solution (2×100 mL) and a 20% aqueous sodium chloride solution 1×100 mL), and then dried over anhydrous sodium sulfate. The solvent was removed in vacuo to give 1(R),5(S)-bicyclo[3.1.0]hexan-2-spiro-2'-(4(S),5(S)-diphenyl dioxolane) (8.91 g, 99%) as a white solid. HPLC (Chiralpak AD-RH, 150×5 mm, 220 nm, 0.5 cc/min, 80 min, mobile phase 5 ethanol/5 methanol/4 water, $R_t$ 1(R),5(S)=20.24 min, 1(S), 5(R)=27.83 min) indicated 87 area % purity and 91% de.

Step 3

A mixture of 1(R),5(S)-bicyclo[3.1.0]hexan-2-spiro-2'-(4(S),5(S)-diphenyl dioxolane (2.51 g, 8.58 mmol) and anhydrous potassium carbonate (2.99 g, 21.6 mmol) in methylene chloride (25 mL) was cooled to −8° C. under nitrogen and then was treated with trimethyl silyl iodide (1.52 mL, 10.7 mmol) via syringe over 7 min. The reaction was stirred for 1 h at −6° C. to −8° C. At this time, a 30% aqueous sodium thiosulfate solution (25 mL, 30 mmol) was added to the cold reaction over 5 min. When the exotherm subsided, the bath was removed, and the reaction was stirred for 1.5 h at 25° C. The layers were separated, and the aqueous phase was extracted with methylene chloride (25 mL). The combined extracts were washed with water (2×25 mL), dried over anhydrous sodium sulfate, and concentrated in vacuo to give a crude product (3.34 g, 92.7%) as a white solid. Flash chromatography (Merck Silica gel 60, 230-400 mesh, 2% ethyl ether/petroleum ether) afforded 7(R)-iodomethyl-2(S),3(S)-diphenyl-1,4-dioxa-spiro[4.4]nonane (2.445 g, 67.7%) as a white solid.

Step 4

A solution of 1,1,1,3,3,3-hexamethyldisilazane (3.18 mL, 15.05 mmol) in tetrahydrofuran (20 mL) cooled to −20° C. was treated with a 2.5M solution of n-butyllithium in hexanes (5.8 mL, 14.5 meq) over 10 min at such a rate as to keep the temperature below −15° C. The mixture was stirred for an additional 5 min. The cold reaction mixture was then treated with a solution of 2-(3-chloro-4-methylsulfanyl-phenyl)-N-(2(R)-hydroxy-1 (R)-methyl-2-phenyl-ethyl)-N-methylacetamide (prepared as in Example 30, 2.77 g, 7.61 mmol) in tetrahydrofuran (22 mL) via syringe over 8 min, at such a rate as to keep the temperature below -15° C. The reaction was then slowly allowed to warm to −7° C. over 20 min and then a solution of 7(R)-iodomethyl-2(S),3(S)-diphenyl-1,4-dioxa-spiro[4.4]nonane (2.42 g, 5.76 mmol) and 1,3-dimethyl-3,4,5,6-tetrahydro-2(1H)-pyrimidinone (1.7 mL, 14.1 mmol) in tetrahydrofuran (10 mL) was added over 6 min. An exotherm increased the temperature to −4° C. during the addition. The reaction was allowed to warm to 0° C., where it was stirred for an additional 3 h. At this time, the reaction was poured into a mixture of toluene (70 mL) and a 20% aqueous ammonium chloride solution (50 mL, 187 mmol) and was then stirred vigorously. The organic layer was separated and re-washed with a 20% aqueous ammonium chloride solution (50 mL, 187 mmol). The organic layer was dried over anhydrous sodium sulfate, and concentrated in vacuo to give 2(R)-(3-chloro-4-methylsulfanyl-phenyl)-3-(2(S),3 (S)-diphenyl-1,4-dioxa-spiro [4.4] non-7(S)-yl)-N-(2(R)-hydroxy-1(R)-methyl-2-phenyl-ethyl)-N-methyl-propionamide (3.86 g) as an overweight brown semi-solid. Flash chromatography (Merck Silica gel 60, 230-400 mesh, 1/1 hexanes/ethyl acetate) afforded 2(R)-(3-chloro-4-methylsulfanyl-phenyl)-3-(2(S),3(S)-diphenyl-1,4-dioxa-spiro[4.4]non-7(S)-yl)-N-(2(R)-hydroxy-1(R)-methyl-2-phenyl-ethyl)-N-methylpropionamide as a yellow foam (2.28 g, 60.4%).

Step 5

A mixture of 2(R)-(3-chloro-4-methylsulfanyl-phenyl)-3-(2(S),3(S)-diphenyl-1,4-dioxa-spiro[4.4]non-7(S)-yl)-N-(2(R)-hydroxy-1 (R)-methyl-2-phenyl-ethyl)-N-methyl-propionamide (2.28 g, 3.47 mmol), 1,4-dioxane (4.56 mL), and a 9N aqueous sulfuric acid solution (4.5 mL) was heated under reflux for 18 h. At this time, the reaction was cooled to 5° C. and diluted with water (12 mL). The aqueous portion was decanted. The resulting viscous oil was dissolved in tert-butyl methyl ether (30 mL), washed with water 3×10 mL), and dried over anhydrous sodium sulfate. The combined aqueous phases were back-extracted with ethyl acetate (20 mL). The combined organics were washed with water 3×10 mL), dried over anhydrous sodium sulfate, and concentrated in vacuo to afford the crude product (1.76 g) as an overweight, brown semi-solid. This material was recrystallized in 1:1 ethyl acetate:hexanes to afford 2(R)-(3-chloro-4-methylsulfanyl-phenyl)-3-((S)-3-oxo-cyclopenyl)-propionic acid (422.1 mg, 38.8%) as an off-white solid. HPLC (Zorbax XDB-C8 150×5 mm, 20-100% acetonitrile/water over 20 min, 20 min run, 220 nm, 1 cc/min $R_t$=10.3 min) indicated 98.5 area % purity, and HPLC (Chiralpak AD-RH, 150×5 mm, 70% ethanol/water, 30 min run, 230 nm, 0.5 cc/min, $R_t$ of 2(R), 3(S)=15.2 min; 2(R), 3(R)=22.1 min) showed 90% de.

Step 6

A solution of 2(R)-(3-chloro-4-methylsulfanyl-phenyl)-3-((S)-3-oxo-cyclopenyl)-propionic acid (189 mg, 0.598 mmol) and acetone (5 mL) stirred at 25° C. was treated with a 0.05M solution of dimethyl dioxirane in acetone (26 mL, 1.3 mmol. After 1 h, the volatiles were removed in vacuo to afford 2(R)-(3-chloro-4-methanesulfonyl-phenyl)-3-((S)-3-oxo-cyclopentyl)-propionic acid (172.4 mg, 83%) as a white solid.

Step 7

A mixture of 2(R)-(3-chloro-4-methanesulfonyl-phenyl)-3-((S)-3-oxo-cyclopentyl)-propionic acid (544 mg, 1.58 mmol), methylene chloride (7 mL), toluene (5 mL), and a catalytic amount of N,N-dimethylformamide (10 μL, 0.13 mmol) under nitrogen was treated with oxalyl chloride (1.4 mL, 16.3 mmol). The reaction was stirred for 1 h (gas evolution). At this time, the reaction was then partially evaporated in vacuo at 25° C. to remove excess oxalyl chloride. The residue was co-evaporated with toluene (2×4 mL) and concentrated in vacuo to about 4 mL. The resulting brown slurry was added via a cannula over 15 min to a mixture of 2-aminopyrazine (189 mg, 1.99 mmol), methylene chloride (4 mL), and pyridine (170 μL, 2.1 mmol) cooled to −10° C. The reaction was allowed to warm to 25° C., where it was stirred for 18 h. At this time, the reaction was quenched with water (700 μL) followed by a 1M aqueous citric acid solution (5 ml, 5 mmol). The reaction then was diluted with ethyl acetate (40 ml) and a 1M aqueous citric acid solution (20 mL), mixed well, and the phases were separated. The organic phase was washed with a 1M aqueous citric acid solution 3×5 mL). The combined aqueous phases were back-extracted with ethyl acetate (30 mL). The combined organic phases were washed with a 10% aqueous potassium bicarbonate solution 3×25 mL), dried over anhydrous sodium sulfate, filtered, and concentrated in vacuo to afford a crude product (506.6 mg, 76%) as a brown foam. Flash chromatography (Merck Silica gel 60, 230-400 mesh, ethyl acetate) afforded 2(R)-(3-chloro-4-methanesulfonyl-phenyl)-3-((S)-3-oxo-cyclopentyl)-N-pyrazin-2-yl-propionamide (442 mg, 66%) as a tan foam. HPLC (Zorbax XDB-C8 150×5 mm, 20-100% acetonitrile/water over 20 min, 20 min run, 220 nm, 1 cc/min $R_t$=7.7 min) indicated 95.3 area % purity, and HPLC (Chiralpak AD-RH, 150×5 mm, 5 ethanol/5 methanol/4 water, 60 min run, 220 nm, 0.5 cc/min, $R_t$ of 2(R), 3(S)=25.2 min; 2(R), 3(R) =39.2 min) showed 90.5% de.

EXAMPLE 48

2(R)-(3-Chloro-4-methanesulfonyl-phenyl)-3-((R)-3-oxo-cyclopentyl)-N-pyrazin-2-yl-propionamide

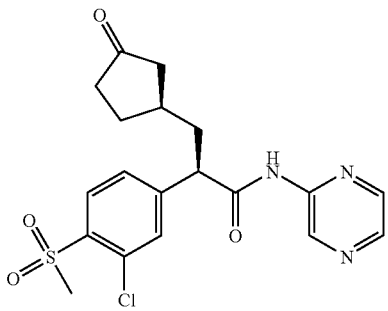

2(R)-(3-Chloro-4-methanesulfonyl-phenyl)-3-((R)-3-oxo-cyclopentyl)-N-pyrazin-2-yl-propionamide was prepared in a similar manner as 2(R)-(3-chloro-4-methanesulfonyl-phenyl)-3-((S)-3-oxo-cyclopentyl)-N-pyrazin-2-yl-propionamide (Example 47) starting with (R,R)-hydrobenzoin (Wang, Z.-M.; Sharpless, K. B. *J. Org. Chem.* 1994, 59, 8302).

Step 1

2(R),3(R)-diphenyl-1,4-dioxa-spiro[4.4]non-6-ene was similarly obtained from 2-cyclopentene-1-one and (R,R)-hydrobenzoin in toluene in 91.5% yield as a white solid.

Step 2

1(S),5(R)-bicyclo[3.1.0]hexan-2-spiro-2′-(4(R),5(R)-diphenyl dioxolane) was similarly obtained from 2(R),3(R)-diphenyl-1,4-dioxa-spiro[4.4]non-6-ene in 68% yield after crystallization from pentane. HPLC (Zorbax XDB-C8 150×5 mm, 5-100% acetonitrile/water + 0.1% trifluoroacetic acid, $R_t$ 18.0 min) indicated 96.5 area % purity.

Step 3

7(S)-iodomethyl-2(R),3(R)-diphenyl-1,4-dioxa-spiro[4.4]nonane was similarly obtained from 1(S),5(R)-bicyclo[3.1.0]hexan-2-spiro-2′-(4(R),5(R)-diphenyl dioxolane) at 25° C. in 71.7% yield as a white solid.

Step 4

2(R)-(3-chloro-4-methylsulfanyl-phenyl)-3-(2(R),3(R)-diphenyl-1,4-dioxa-spiro[4.4]non-7(R)-yl)-N-(2(R)-hydroxy-1(R)-methyl-2-phenyl-ethyl)-N-methylpropionamide was similarly obtained from 7(S)-iodomethyl-2(R),3(R)-diphenyl-1,4-dioxa-spiro[4.4]nonane in 65% yield.

Step 5

2(R)-(3-chloro-4-methylsulfanyl-phenyl)-3-((R)-3-oxo-cyclopenyl)-propionic acid was similarly obtained from 2(R)-(3-chloro-4-methylsulfanyl-phenyl)-3-(2(R),3(R)-diphenyl-1,4-dioxa-spiro[4.4]non-7(R)-yl)-N-(2(R)-hydroxy-1(R)-methyl-2-phenyl-ethyl)-N-methylpropionamide in 72% yield as a yellow foam.

Step 6

2(R)-(3-chloro-4-methanesulfonyl-phenyl)-3-((R)-3-oxo-cyclopentyl)-propionic acid was similarly obtained from 2(R)-(3-chloro-4-methylsulfanyl-phenyl)-3-((R)-3-oxo-cyclopenyl)-propionic acid in 90% yield as a white solid.

Step 7

2(R)-(3-chloro-4-methanesulfonyl-phenyl)-3-((R)-3-oxo-cyclopentyl)-N-pyrazin-2-yl-propionamide was similarly obtained from 2(R)-(3-chloro-4-methanesulfonyl-phenyl)-3-((R)-3-oxo-cyclopentyl)-propionic acid in 43% yield as a white foam. HPLC (Chiralpak AD-RH, 150×5 mm, 5 ethanol/5 methanol/4 water, 60 min run, 220 nm, 0.5 cc/min, $R_t$ of 2(R),3(S)=25.4 min; 2(R),3(R)=38.9 min) indicated 95.9 area % purity and >99% de.

EXAMPLE 49

N-(5-Bromo-pyrazin-2-yl)-2-(3-chloro-4-methanesulfonyl-phenyl)-3-(3-oxo-cyclopentyl)-propionamide

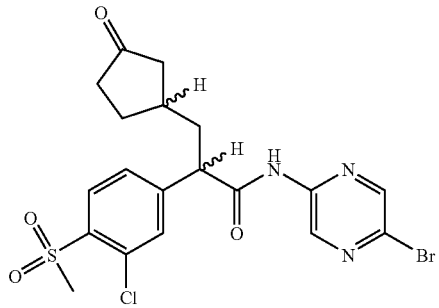

A solution of 2-(3-chloro-4-methanesulfonyl-phenyl)-3-(3-oxo-cyclopentyl)-propionic acid (prepared as in Example 45, 1.05 g, 3.04 mmol) and N,N-dimethylformamide (5 drops) in methylene chloride (10 mL) cooled to 0° C. was treated with oxalyl chloride (0.39 mL, 4.57 mmol). The reaction mixture was stirred at 0° C. for 1 h and then at 25° C. for 1 h. The solution was then concentrated in vacuo, and the orange-brown gel was dissolved in methylene chloride (5 mL). The resulting solution was added dropwise via an addition funnel at 0° C. to a solution of 2-amino-5-bromopyrazine (0.79 g, 4.57 mmol, prepared according to *Tetrahedron* 1988, 44, 2977-2983) in methylene chloride (5 mL) and pyridine (0.37 mL, 4.57 mmol). The reaction mixture was stirred at 0° C. for 30 min and then at 25° C. for 3 h. The reaction mixture was quenched with a 1N aqueous citric acid solution (10 mL) and stirred for 15 min. The reaction was then diluted with a 1N aqueous citric acid solution (50 mL) and ethyl acetate (75 mL). The organic layer was washed with a saturated aqueous sodium bicarbonate solution (50 mL), water (50 mL), and a saturated aqueous sodium chloride solution (50 mL), dried over magnesium sulfate, filtered, and concentrated in vacuo. Biotage chromatography (FLASH 40M, Silica, 50% ethyl acetate/hexanes) afforded N-(5-bromo-pyrazin-2-yl)-2-(3-chloro-4-methanesulfonyl-phenyl)-3-(3-oxo-cyclopentyl)-propionamide (0.622 g, 41%) as a yellow-orange foam: mp 97-103° C. (foam to gel); (ES)$^+$-HRMS m/e calcd for $C_{19}H_{19}BrClN_3O_4S$ (M+H)$^+$ 500.0041. found 500.0048.

EXAMPLE 50

2-(3,4-Dichloro-phenyl)-3-(3-hydroxyimino-cyclopentyl)-N-thiazol-2-yl-propionamide

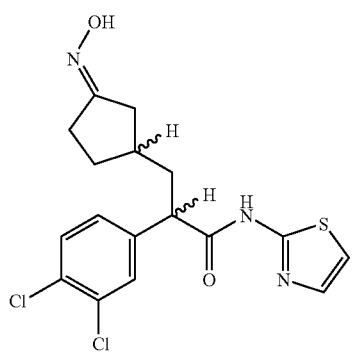

A solution of the 2-(3,4-dichloro-phenyl)-3-(3-oxo-cyclopentyl)-N-thiazol-2-yl-propionamide (prepared as in Example 43, 144.6 mg, 0.38 mmol) and hydroxylamine hydrochloride (39.7 mg, 0.57 mmol) in methanol (1.1 mL) and pyridine (1.1 mL) was heated under reflux for 3 h. The reaction mixture was allowed to cool to 25° C. and then was concentrated in vacuo. The resulting residue was diluted with ethyl acetate (75 mL). The organic layer was washed with a 1N aqueous hydrochloric acid solution (75 mL) and a saturated aqueous sodium chloride solution (75 mL), dried over sodium sulfate, filtered, and concentrated in vacuo. Flash chromatography (Merck Silica gel 60, 70-230 mesh, 70% ethyl acetate/hexanes) afforded 2-(3,4-dichloro-phenyl)-3-(3-hydroxyimino-cyclopentyl)-N-thiazol-2-yl-propionamide (138.9 mg, 92%) as a white foam: mp 98-101° C. (foam to gel); (ES)$^+$-HRMS m/e calcd for $C_{17}H_{17}Cl_2N_3O_2S$ (M+H)$^+$ 398.0492. found 398.0496.

EXAMPLE 51

2-(3-Chloro-4-methanesulfonyl-phenyl)-3-(3-hydroxyimino-cyclopentyl)-N-pyrazin-2-yl-propionamide

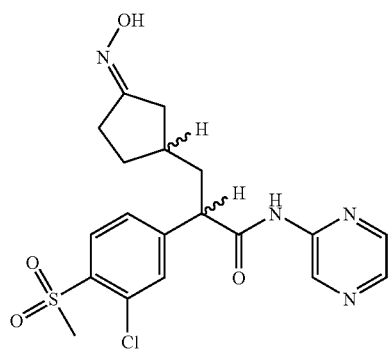

A solution of 2-(3-chloro-4-methanesulfonyl-phenyl)-3-(3-oxo-cyclopentyl)-N-pyrazin-2-yl-propionamide (prepared as in Example 45, 121.9 mg, 0.29 mmol) and hydroxylamine hydrochloride (30.4 mg, 0.43 mmol) in methanol (0.85 mL) and pyridine (0.85 mL) was heated under reflux for 5 h. The reaction mixture was allowed to cool to 25° C. and was then concentrated in vacuo. The resulting residue was diluted with water (50 mL) and extracted with ethyl acetate (50 mL). The organic layer was washed with a 1N aqueous hydrochloric acid solution (2×50 mL) and a saturated aqueous sodium chloride solution (50 mL), dried over sodium sulfate, filtered, and concentrated in vacuo. Flash chromatography (Merck Silica gel 60, 70-230 mesh, 80-100% ethyl acetate/hexanes) afforded 2-(3-chloro-4-methanesulfonyl-phenyl)-3-(3-hydroxyimino-cyclopentyl)-N-pyrazin-2-yl-propionamide (68.8 mg, 55%) as a white solid: mp 205-207° C.; (ES)$^+$-HRMS m/e calcd for $C_{19}H_{21}ClN_4O_4S$ (M+H)$^+$ 437.1045. found 437.1048.

EXAMPLE 52

N-(5-Bromo-pyrazin-2-yl)-2-(3-chloro-4-methanesulfonyl-phenyl)-3-(3-hydroxyimino-cyclopentyl)-propionamide

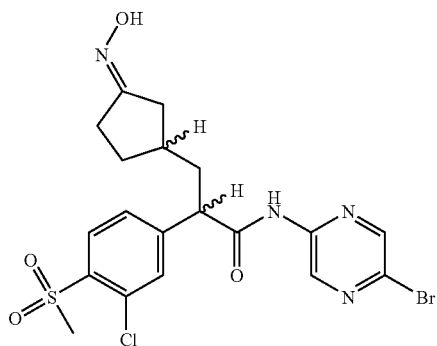

A solution of N-(5-bromo-pyrazin-2-yl)-2-(3-chloro-4-methanesulfonyl-phenyl)-3-(3-oxo-cyclopentyl)-propionamide (prepared as in Example 49, 190 mg, 0.38 mmol) and hydroxylamine hydrochloride (40 mg, 0.57 mmol) in methanol (0.90 mL) and pyridine (0.90 mL) was heated under reflux for 3 h. The reaction mixture was allowed to cool to 25° C. and was then concentrated in vacuo. The resulting residue was diluted with water (50 mL) and extracted with ethyl acetate (50 mL). The organic layers were washed with a 1N aqueous hydrochloric acid solution (50 mL) and a saturated aqueous sodium chloride solution, dried over magnesium sulfate, filtered, and concentrated in vacuo. Biotage chromatography (FLASH 40S, Silica, 75% ethyl acetate/hexanes) afforded the N-(5-bromo-pyrazin-2-yl)-2-(3-chloro-4-methanesulfonyl-phenyl)-3-(3-hydroxyimino-cyclopentyl)-propionamide (150 mg, 77%) as a yellow foam: mp 100-106° C.; (ES)$^+$-HRMS m/e calcd for $C_{19}H_{20}BrClN_4O_4S$ (M+H)$^+$ 515.0150. found 515.0154.

EXAMPLE 53

2-(3,4-Dichloro-phenyl)-3-(3-methoxyimino-cyclopentyl)-N-thiazol-2-yl-propionamide

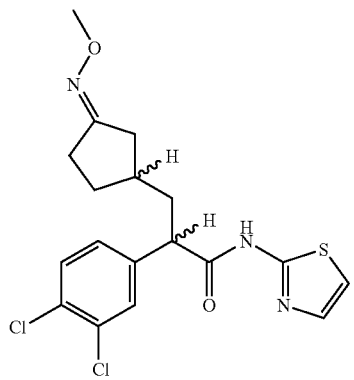

A solution of the 2-(3,4-dichloro-phenyl)-3-(3-oxo-cyclopentyl)-N-thiazol-2-yl-propionamide (prepared as in Example 43, 159.9 mg, 0.41 mmol) and methoxyamine hydrochloride (52.3 mg, 0.62 mmol) in methanol (1.2 mL) and pyridine (1.2 mL) was heated under reflux for 3.5 h. The reaction mixture was allowed to cool to 25° C. and then concentrated in vacuo. The resulting residue was diluted with ethyl acetate (75 mL), washed with a 1N aqueous hydrochloric acid solution (75 mL) and a saturated aqueous sodium chloride solution (75 mL), dried over sodium sulfate, filtered, and concentrated in vacuo. Flash chromatography (Merck Silica gel 60, 230-400 mesh, 50% ethyl acetate/hexanes) afforded 2-(3,4-dichloro-phenyl)-3-(3-methoxyimino-cyclopentyl)-N-thiazol-2-yl-propionamide (168.2 mg, 98%) as a white foam: mp 69-72° C. (foam to gel); (ES)$^+$-HRMS m/e calcd for $C_{18}H_{19}Cl_2N_3O_2S$ (M+H)$^+$ 412.0648. found 412.0652.

EXAMPLE 54

2-(3-Chloro-4-methanesulfonyl-phenyl)-3-(3-methoxyimino-cyclopentyl)-N-pyrazin-2-yl-propionamide

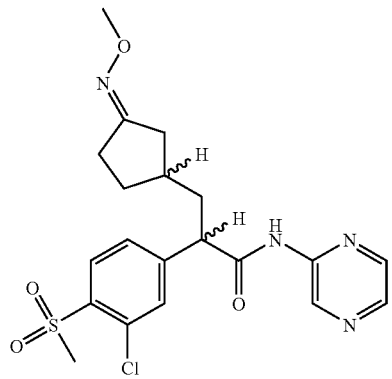

A solution of 2-(3-chloro-4-methanesulfonyl-phenyl)-3-(3-oxo-cyclopentyl)-N-pyrazin-2-yl-propionamide (prepared as in Example 45, 73.5 mg, 0.17 mmol) and methoxyamine hydrochloride (21.8 mg, 0.26 mmol) in methanol (512 μL) and pyridine (512 μL) was heated under reflux for 5 h. The reaction mixture was allowed to cool to 25° C. and was then concentrated in vacuo. The resulting residue was diluted with water (50 mL) and extracted with ethyl acetate (2×50 mL). The organic layers were washed with a saturated aqueous sodium chloride solution (50 mL), dried over sodium sulfate, filtered, and concentrated in vacuo. Flash chromatography (Merck Silica gel 60, 70-230 mesh, 70% ethyl acetate/hexanes) afforded 2-(3-chloro-4-methanesulfonyl-phenyl)-3-(3-methoxyimino-cyclopentyl)-N-pyrazin-2-yl-propionamide (61.2 mg, 78%) as a white foam: mp 85-87° C.; (ES)$^+$-HRMS m/e calcd for $C_{20}H_{23}ClN_4O_4S$ (M+H)$^+$ 451.1202. found 451.1207.

EXAMPLE 55

N-(5-Bromo-pyrazin-2-yl)-2-(3-chloro-4-methanesulfonyl-phenyl)-3-(3-methoxyimino-cyclopentyl)-propionamide

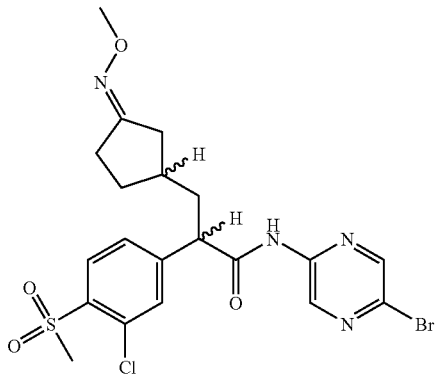

A solution of N-(5-bromo-pyrazin-2-yl)-2-(3-chloro-4-methanesulfonyl-phenyl)-3-(3-oxo-cyclopentyl)-propionamide (prepared as in Example 49, 190 mg, 0.38 mmol) and methoxyamine hydrochloride (48 mg, 0.57 mmol) in methanol (0.90 mL) and pyridine (0.90 mL) was heated under reflux for 3 h. The reaction mixture was allowed to cool to 25° C. and then was concentrated in vacuo. The resulting residue was diluted with water (50 mL) and extracted with ethyl acetate (50 mL). The organic layers were washed with a 1N aqueous hydrochloric acid solution (50 mL) and a saturated aqueous sodium chloride solution (50 mL), dried over magnesium sulfate, filtered, and concentrated in vacuo. Biotage chromatography (FLASH 40S, Silica, 50% ethyl acetate/hexanes) afforded the N-(5-bromo-pyrazin-2-yl)-2-(3-chloro-4-methanesulfonyl-phenyl)-3-(3-methoxyimino-cyclopentyl)-propionamide (61.2 mg, 78%) as a yellow foam: mp 91-97° C.; (ES)$^+$-HRMS m/e calcd for $C_{20}H_{22}BrClN_4O_4S$ (M+H)$^+$ 529.0307. found 529.0310.

EXAMPLE 56

2-(3,4-Dichloro-phenyl)-3-(3,3-difluoro-cyclopentyl)-N-thiazol-2-yl-propionamide

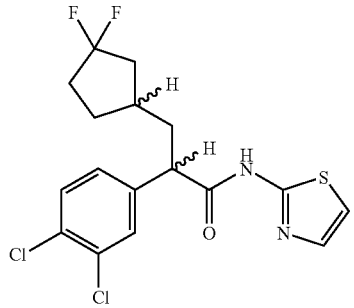

A mixture of 2-(3,4-dichloro-phenyl)-3-(3-hydroxy-cyclopentyl)-propionic acid methyl ester (prepared as in Example 36, 356.4 mg, 1.12 mmol), N-methylmorpholine N-oxide (197 mg, 1.68 mmol), and powdered molecular sieves (1.12 g) in methylene chloride (2.25 mL) at 25° C. was treated with tetrapropylammonium perrhuthenate (20 mg, 0.05 mmol). The resulting mixture was stirred at 25° C. for 30 min. At this time, the reaction was filtered through a pad of celite (ethyl acetate as eluent). The filtrate was concentrated in vacuo. Flash chromatography (Merck Silica gel 60, 230-400 mesh, 75/25 hexanes/ethyl acetate) afforded 2-(3,4-dichloro-phenyl)-3-(3-oxo-cyclopentyl)-propionic acid methyl ester (261.3 mg, 73.8%) as a clear oil: EI-HRMS m/e calcd for $C_{15}H_{16}Cl_2O_3$ (M+Na)$^+$ 337.0370. found 337.0371.

A solution of 2-(3,4-dichloro-phenyl)-3-(2-oxo-cyclopentyl)-propionic acid methyl ester (261.3 mg, 0.83 mmol) in methylene chloride (0.41 mL) was treated with diethylaminosulfur trifluoride (0.16 mL, 1.24 mmol). The resulting mixture was heated at 60° C. for 18 h. At this time, the reaction was cooled to 25° C. and was diluted with water (50 mL). This solution was extracted into methylene chloride 3×30 mL). The organics were dried over sodium sulfate, filtered, and concentrated in vacuo. Flash chromatography (Merck Silica gel 60, 230-400 mesh, 90/10 hexanes/ethyl acetate) afforded 2-(3,4-dichloro-phenyl)-3-(3,3-difluoro-cyclopentyl)-propionic acid methyl ester (79.4 mg, 28.4%) as a yellow oil.

A mixture of 2-(3,4-dichloro-phenyl)-3-(3,3-difluoro-cyclopentyl)-propionic acid methyl ester (75 mg, 0.22 mmol) and 2-aminothiazole (27 mg, 0.26 mmol) in a solution of magnesium methoxide in methanol (7.4 wt. %, 0.63 mL, 0.44 mmol) was heated to 110° C. for 18 h. At this time, the reaction mixture was cooled to 25° C. and then concentrated in vacuo. Flash chromatography (Merck Silica gel 60, 230-400 mesh, 70/30 hexanes/ethyl acetate) afforded 2-(3,4-dichloro-phenyl)-3-(3,3-difluoro-cyclopentyl)-N-thiazol-2-yl-propionamide (44.2 mg, 49%) as an off-white solid: mp 154-156° C.; FAB-HRMS m/e calcd for $C_{17}H_{16}F_2Cl_2N_2OS$ (M+H)$^3$ 405.0402. found 405.0404.

EXAMPLE 57

2-(3-Chloro-4-methanesulfonyl-phenyl)-3-(3-hydroxy-3-methyl-cyclopentyl)-N-pyrazin-2-yl-propionamide

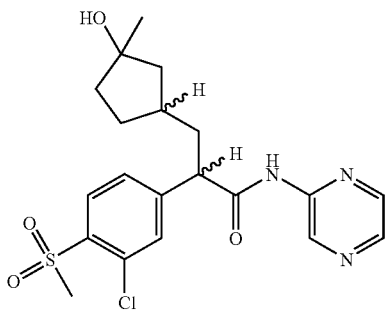

3.0M solution of methylmagnesium bromide in ether (2.53 mL, 7.59 mmol) cooled to 0° C. was treated dropwise with a solution of 2-(3-chloro-4-methanesulfonyl-phenyl)-3-(3-oxo-cyclopentyl)-N-pyrazin-2-yl-propionamide (prepared as in Example 45, 0.10 g, 0.237 mmol) in tetrahydrofuran (1 mL). The resulting solution was stirred at 0° C. for 30 min, quenched with a saturated aqueous ammonium chloride solution (3 mL), and partitioned between a saturated aqueous ammonium chloride solution (20 mL) and ethyl acetate (25 mL). The aqueous layer was extracted with ethyl acetate (25 mL). The combined organic layers were dried over magnesium sulfate, filtered, and concentrated in vacuo. Biotage chromatography (FLASH 40S, Silica, 80% ethyl acetate/hexanes) afforded 2-(3-chloro-4-methanesulfonyl-phenyl)-3-(3-hydroxy-3-methyl-cyclopentyl)-N-pyrazin-2-yl-propionamide (37 mg, 35%) as a yellow foam: mp 78-84° C. (foam to gel); (ES)$^+$-HRMS m/e calcd for $C_{20}H_{24}ClN_3O_4S$ (M+H)$^+$ 438.1249. found 438.1254.

EXAMPLE 58

2-(3-Chloro-4-methanesulfonyl-phenyl)-3-(4-oxocyclohexyl)-N-pyrazin-2-yl-propionamide

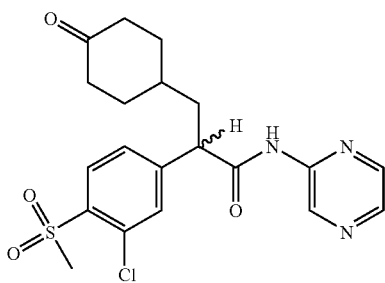

A solution of 4-cyclohexanonecarboxylic acid ethyl ester (5.00 g, 29.38 mmol) and ethylene glycol (2.13 mL, 38.19 mmol) in toluene (150 mL) was heated in a Dean-Stark trap at reflux for 1 h and was then treated with p-toluenesulfonic acid monohydrate (56.74 mg, 0.294 mmol). The reaction solution was heated an additional 30 min at reflux, cooled to 25° C., and concentrated in vacuo. The resulting oil was dissolved in ethyl acetate (200 mL), washed with water (2×50 mL), dried over magnesium sulfate, filtered, and concentrated in vacuo to afford pure 1,4-dioxa-spiro[4.5]decane-8-carboxylic acid ethyl ester (6.25 g, 99.3%) as a colorless oil.

A solution of 1,4-dioxa-spiro[4.5]decane-8-carboxylic acid ethyl ester (2.00 g, 9.33 mmol) in tetrahydrofuran (40 mL) at 0° C. was treated dropwise with a 1.0M solution of lithium aluminum hydride in tetrahydrofuran (10.0 mL, 10.0 mmol). The reaction mixture was stirred at 0° C. for 30 min and was then quenched by the dropwise addition of ethyl acetate. The reaction was then diluted with a saturated aqueous ammonium chloride solution (25 mL) and extracted with ethyl acetate 3×25 mL). The combined organic extracts were dried over sodium sulfate, filtered, and concentrated in vacuo to afford pure (1,4-dioxa-spiro[4.5]dec-8-yl)-methanol (1.60 g, 99.9%) as a colorless oil.

A solution of (1,4-dioxa-spiro[4.5]dec-8-yl)-methanol (1.60 g, 9.29 mmol) in methylene chloride (50 mL) was treated with 4-(dimethylamino)pyridine (1.26 g, 10.22 mmol) and p-toluenesulfonyl chloride (1.86 g, 9.75 mmol). The reaction mixture was stirred at 25° C. for 2 h, and was then washed with a saturated aqueous sodium bicarbonate solution (1×25 mL). The organic layer was dried over magnesium sulfate, filtered, and concentrated in vacuo. The resulting oil was dissolved in acetone (30 mL) and treated with sodium iodide (4.73 g, 31.53 mmol). The reaction was heated under reflux for 2 h, cooled to 25° C., and then concentrated in vacuo. The resulting residue was suspended in ethyl acetate (50 mL), washed with water (2×15 mL), dried over magnesium sulfate, filtered, and concentrated in vacuo. Biotage chromatography (FLASH 40S, Silica, 19/1 hexanes/ethyl acetate) afforded 8-iodomethyl-1,4-dioxa-spiro[4.5]decane (2.32 g, 88.6%) as a colorless oil.

A solution of diisopropylamine (0.23 mL, 1.63 mmol) in dry tetrahydrofuran (5.0 mL) cooled to −78° C. under nitrogen was treated with a 2.5M solution of n-butyllithium in hexanes (0.65 mL, 1.63 mmol). The reaction mixture was stirred at −78° C. for 30 min and then treated dropwise with a solution of (3-chloro-4-methylsulfanyl-phenyl)-acetic acid methyl ester (prepared as in Example 4, 340 mg, 1.48 mmol) in dry tetrahydrofuran (3.0 mL) and 1,3-dimethyl-3,4,5,6-tetrahydro-2(1H)-pyrimidinone (1.0 mL). The reaction mixture turned dark in color and was allowed to stir at −78° C. for 1 h, at which time, a solution of 8-iodomethyl-1,4-dioxa-spiro[4.5]decane (500 mg, 1.78 mmol) in a small amount of dry tetrahydrofuran was added dropwise. The reaction mixture was allowed to warm to 25° C., where it was stirred for 24 h. The reaction mixture was quenched with a saturated aqueous ammonium chloride solution and then concentrated in vacuo to remove tetrahydrofuran. The aqueous residue was acidified using a 10% aqueous hydrochloric acid solution. The resulting aqueous layer was extracted with ethyl acetate (2×100 mL). The combined organic extracts were dried over sodium sulfate, filtered, and concentrated in vacuo. Biotage chromatography (FLASH 40S Silica 8/2 hexanes/ethyl acetate) afforded the 2-(3-chloro-4-methylsulfanyl-phenyl)-3-(1,4-dioxa-spiro[4.5]dec-8-yl)-propionic acid methyl ester (315 mg, 55%) as a yellow viscous oil: EI-HRMS m/e calcd for $C_{19}H_{25}ClO_4S$ (M+) 384.1162. found 384.1169.

A solution of 2-(3-chloro-4-methylsulfanyl-phenyl)-3-(1,4-dioxa-spiro[4.5]dec-8-yl)-propionic acid methyl ester (746 mg, 1.93 mmol) in methylene chloride (22 mL) cooled to 0° C. was treated dropwise with a pre-mixed solution of 3-chloroperoxybenzoic acid (70% grade, 955 mg, 3.86 mmol) and sodium bicarbonate (652 mg, 7.72 mmol) in methylene chloride (11 mL). The reaction mixture was stirred at 25° C. for 4.5 h, after which time, the reaction mixture was diluted with methylene chloride (100 mL) and washed with water (100 mL). The organic phase was cooled to 0° C. and successively washed with a 10% aqueous sodium sulfite solution (100 mL), a saturated aqueous sodium bicarbonate solution (100 mL), and a 50% aqueous sodium chloride solution (100 mL). The combined organic extracts were dried over sodium sulfate, filtered, and concentrated in vacuo. Biotage chromatography (FLASH 40S Silica, 6/4 hexanes/ethyl acetate) afforded 2-(3-chloro-4-methylsulfonyl-phenyl)-3-(1,4-dioxa-spiro[4.5]dec-8-yl)-propionic acid methyl ester (680 mg, 84%) as a colorless gum: EI-HRMS m/e calcd for $C_{19}H_{25}ClO_{64}S$ (M+Na)+ 439.0953. found 439.0957.

A solution of 2-(3-chloro-4-methylsulfonyl-phenyl)-3-(1,4-dioxa-spiro[4.5]dec-8-yl)-propionic acid methyl ester (667 mg, 1.60 mmol) in acetone (15 mL) was treated with a 10% aqueous hydrochloric acid solution (1.8 mL). The reaction mixture was stirred at 25° C. for 24 h. The reaction mixture was then diluted with water (50 mL) and extracted with ethyl acetate (100 mL). The organic layer was dried over sodium sulfate, filtered, and concentrated in vacuo to afford pure 2-(3-chloro-4-methylsulfonyl-phenyl)-3-(4-oxo-cyclohexyl)-propionic acid methyl ester (600 mg, 100%) as a colorless gum which was used without further purification: EI-HRMS m/e calcd for $C_{17}H_{21}ClO_5S$ (M+Na)+ 395.0690. found 395.0692.

A solution of 2-(3-chloro-4-methylsulfonyl-phenyl)-3-(4-oxo-cyclohexyl)-propionic acid methyl ester (590 mg, 1.58 mmol) in methanol (7.0 mL) and water (3.0 mL) was treated with lithium hydroxide (980 mg, 31.6 mmol). The reaction mixture was stirred at 25° C. for 2 h and then concentrated in vacuo to remove methanol. The remaining aqueous layer was diluted with water (25 mL) and washed with ethyl acetate (2×50 mL). The aqueous layer was then acidified to pH=3 with a 1N aqueous hydrochloric acid solution and was extracted with ethyl acetate (2×50 mL). The combined organic layers were washed with a saturated aqueous sodium chloride solution (1×50 mL), dried over sodium sulfate, filtered, and concentrated in vacuo to afford pure 2-(3-chloro-4-methylsulfonyl-phenyl)-3-(4-oxo-cyclohexyl)-propionic acid (550 mg, 97%) as a colorless gum: EI-HRMS m/e calcd for $C_{16}H_{19}ClO_5S$ (M+Na)+ 381.0534. found 381.0537.

A solution of 2-(3-chloro-4-methylsulfonyl-phenyl)-3-(4-oxo-cyclohexyl)-propionic acid (267 mg, 0.75 mmol) in methylene chloride (10 mL) was treated with N,N-dimethylformamide (3 drops) and then cooled to 0° C. The reaction mixture was then treated with a 2.0M solution of oxalyl chloride in methylene chloride (0.45 mL, 0.90 mmol). The reaction mixture was stirred at 25° C. for 30 min and then concentrated in vacuo to remove solvents and excess oxalyl chloride. The resulting residue was re-dissolved in dry tetrahydrofuran (10 mL) and was treated dropwise with a solution of 2-aminopyrazine (143 mg, 1.50 mmol) in tetrahydrofuran (10 mL) and pyridine (0.30 mL, 3.75 mmol). The resulting reaction mixture was stirred at 25° C. for 2 h. The reaction mixture was then diluted with a 1N aqueous citric acid solution (25 mL) and concentrated to remove tetrahydrofuran. The remaining aqueous residue was then extracted with a 3/2 solution of chloroform/methanol (2×25 mL). The combined organic extracts were dried over sodium sulfate, filtered, and concentrated in vacuo. Biotage chromatography (FLASH 40S, Silica, 3/2 hexanes/ethyl acetate) afforded 2-(3-chloro-4-methanesulfonyl-phenyl)-3-(4-oxo-cyclohexyl)-N-pyrazin-2-yl-propionamide (266 mg, 81%) as an off-white foam: EI-HRMS m/e calcd for $C_{20}H_{22}ClN_3O_4S$ (M+H)+ 436.1093. found 436.1099.

EXAMPLE 59

N-(5-Bromo-pyrazin-2-yl)-2-(3-chloro-4-methanesulfonyl-phenyl)-3-(4-oxo-cyclohexyl)-propionamide

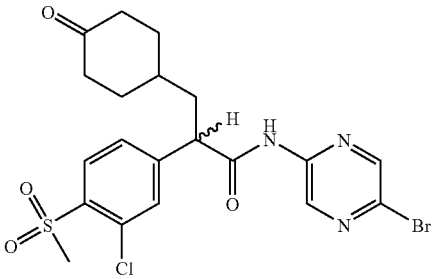

A solution of 2-(3-chloro-4-methylsulfonyl-phenyl)-3-(4-oxo-cyclohexyl)-propionic acid (prepared as in Example 58, 267 mg, 0.75 mmol) in methylene chloride (10 mL) was treated with N,N-dimethylformamide (3 drops) and then cooled to 0° C. The reaction mixture was then treated with a 2.1 M solution of oxalyl chloride in methylene chloride (0.45 mL, 0.90 mmol). The reaction mixture was stirred at 25° C. for 30 min and then concentrated in vacuo to remove solvents and excess oxalyl chloride. The resulting residue was re-dissolved in dry tetrahydrofuran (10 mL) and was treated dropwise with a solution of 2-amino-5-bromopyrazine (261 mg, 1.50 mmol, prepared according to *Tetrahedron* 1988, 44, 2977-2983) in tetrahydrofuran (10 mL) and pyridine (0.30 mL, 3.75 mmol). The resulting reaction mixture was stirred at 25° C. for 2 h. The reaction mixture was then diluted with a 1N aqueous citric acid solution (25 mL) and then concentrated to remove tetrahydrofuran. The remaining aqueous residue was then extracted with a 3/2 solution of chloroform/methanol (2×25 mL). The combined organic extracts were dried over sodium sulfate, filtered, and concentrated in vacuo. Biotage chromatography (FLASH 40M, Silica, 35/65 hexanes/ethyl acetate) afforded N-(5-bromo-pyrazin-2-yl)-2-(3-chloro-4-methanesulfonyl-phenyl)-3-(4-oxo-cyclohexyl)-propionamide (193 mg, 50%) as a yellow foam: EI-HRMS m/e calcd for $C_{20}H_{21}BrClN_3O_4S$ (M+H)$^+$ 514.0198. found 514.0200.

EXAMPLE 60

N-(5-Bromo-pyrazin-2-yl)-2(R)-(3-chloro-4-methanesulfonyl-phenyl)-3-(4-oxo-cyclohexyl)-propionamide

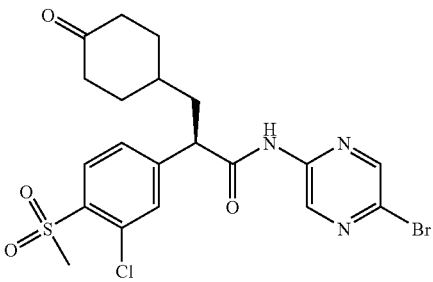

A mixture of (3-chloro-4-methylsulfanyl-phenyl)-acetic acid (prepared as in Example 4, 10.48 g, 48.4 mmol) and potassium carbonate (20.1 g, 145.1 mmol) in acetone (65 mL) was cooled to −10° C. The pale yellow slurry was then treated dropwise with trimethylacetyl chloride (6.25 mL, 50.8 mmol) while maintaining the temperature below −10° C. The resulting reaction mixture was stirred at −10° C. for 15 min and then allowed to warm to 0° C., where it was stirred for 10 min. The reaction mixture was re-cooled to −10° C. and then treated with (1R,2R)-(−)-pseudoephedrine (11.99 g, 72.5 mmol), resulting in an exotherm. The reaction mixture was stirred at −10° C. for 10 min and then warmed to 25° C., where it was stirred for 1 h. At this time, the reaction mixture was then quenched with water (50 mL) and then extracted with ethyl acetate (1×100 mL). The organic layer was washed with water (2×40 mL). The aqueous layers were combined and back-extracted with ethyl acetate (2×50 mL). The combined organic layers were dried over magnesium sulfate, filtered, and concentrated in vacuo. The crude material was recrystallized from ethyl acetate (45 mL) and hexanes (80 mL) to afford 2-(3-chloro-4-methylsulfanyl-phenyl)-N-[2(R)-hydroxy-1(R)-methyl-2(R)-phenyl-ethyl]-N-methyl-acetamide (13.75 g, 78%) as a light yellow solid: mp 111.5-112.9° C.; $[\alpha]^{23}_{589}$=−97.2° (c=0.104, chloroform); FAB-HRMS m/e calcd for $C_{19}H_{22}ClNSO_2$ (M+H)$^+$ 364.1138. found 364.1142.

A solution of 1,1,1,3,3,3-hexamethyldisilazane (9.73 mL, 46.07 mmol) in tetrahydrofuran (35 mL) cooled to −78° C. was treated with a 2.5M solution of n-butyllithium in hexanes (18.00 mL, 45.0 mmol). The reaction mixture was stirred at −78° C. for 15 min and then slowly treated with a solution of 2-(3-chloro-4-methylsulfanyl-phenyl)-N-[2(R)-hydroxy-1(R)-methyl-2(R)-phenyl-ethyl]-N-methyl-acetamide (6.45 g, 17.72 mmol) in tetrahydrofuran (35 mL) while maintaining the temperature below −65° C. The resulting yellow-orange reaction mixture was stirred at −78° C. for 15 min and then allowed to warm to 0° C., where it was stirred for 20 min. The reaction mixture was then re-cooled to −78° C. and then treated with a solution of 8-iodomethyl-1,4-dioxa-spiro[4.5]decane (prepared as in Example 58, 10.00 g, 35.4 mmol) in 1,3-dimethyl-3,4,5,6-tetrahydro-2(1H)-pyrimidinone (3.0 mL) and tetrahydrofuran (10 mL) The resulting reaction mixture was stirred at −78° C. for 30 min and then allowed to warm to 25° C., where it was stirred for 16 h. The reaction mixture was diluted with ethyl acetate (100 mL) and then was washed with a saturated aqueous ammonium chloride solution 1×50 mL). The aqueous layer was then extracted with ethyl acetate (2×50 mL). The combined organic layers were washed with a saturated aqueous sodium chloride solution (I × 50 mL), dried over sodium sulfate, filtered, and concentrated in vacuo. The resulting material was then re-dissolved in ethyl acetate. This organic phase was washed with a 10% aqueous sulfuric acid solution (2×100 mL) and a 10% aqueous sodium bicarbonate solution (2×100 mL), dried over magnesium sulfate, filtered, and concentrated in vacuo. Flash chromatography (Merck Silica gel 60, 70-230 mesh, 2/3 hexanes/ethyl acetate to 1/4 hexanes/ethyl acetate) afforded the 2(R)-(3-chloro-4-methylsulfanyl-phenyl)-3-(1,4-dioxa-spiro[4.5]dec-8-yl)-N-(2 (R)-hydroxy-1(R)-methyl-2(R)-phenyl-ethyl)-N-methyl-propionamide (9.11 g, 99.0%) as a white foam: $[\alpha]^{23}_{589}$=−79.49° (c=0.39, chloroform); EI-HRMS m/e calcd for $C_{28}H_{36}ClNO_4S$ (M+H)$^+$ 518.2127. found 518.2123.

A solution of 2(R)-(3-chloro-4-methylsulfanyl-phenyl)-3-(1,4-dioxa-spiro[4.5]dec-8-yl)-N-(2(R)-hydroxy-1(R)-methyl-2(R)-phenyl-ethyl)-N-methyl-propionamide (6.30 g, 12.16 mmol) in methylene chloride (70 mL) cooled to 0° C. was treated dropwise with a pre-mixed solution of 3-chloroperoxybenzoic acid (70%, 6.00 g, 24.32 mmol) and sodium bicarbonate (4.09 g, 48.64 mmol) in methylene chloride (70 mL) over a 10 min period. The resulting mixture was allowed to warm to 25° C., where it was stirred for 2 h. The reaction mixture was diluted with methylene chloride (100 mL), re-cooled to 0° C., and treated dropwise with an additional solution of 3-chloroperoxybenzoic acid (70%, 3.00 g, 12.16 mmol) and sodium bicarbonate (2.05 g, 24.32 mmol) in methylene chloride (35 mL). The resulting mixture was allowed to warm to 25° C., where it was stirred for 2 h. The reaction mixture was then diluted with methylene chloride (1 L), washed with water 1×500 mL), cooled to 0° C., and then washed sequentially with a saturated aqueous sodium bisulfite solution 1×500 mL), a saturated aqueous sodium bicarbonate solution 1×500 mL), and a saturated aqueous sodium chloride solution 1×500 mL). The combined organic extracts were dried over magnesium sulfate and concentrated in vacuo. The resulting white foam was then dissolved in dioxane (40 mL), treated with a 9N aqueous sulfuric acid solution (40 mL), and heated at 105° C. for 16 h. The reaction mixture was then cooled to 0° C. with an ice bath, and the product was precipitated by adding water (500 mL). The suspension was stirred at 0° C. until the supernatant, which was initially turbid, became clear and light yellow in color. The solid was filtered off and dried by suction. The solid material was dissolved in hot glacial acetic acid (40 mL), and the hot solution was treated with water (25 mL) to initiate crystallization. The mixture was allowed to cool to 25° C. and then treated with an additional amount of water (50 mL). After stirring at 25° C. for 1 h, the solid was collected by filtration. The solid was dried in a high vacuum desiccator with phosphorus pentoxide to afford 2(R)-(3-chloro-4-methanesulfonyl-phenyl)-3-(4-oxo-cyclohexyl)-propionic acid (4.10 g, 94%) as an off-white solid: mp 129-131° C.; $[\alpha]^{23}_{589}$=–42.22° (c=0.36, chloroform); EI-HRMS m/e calcd for $C16H_{19}ClO_5S$ (M+Na)$^+$ 381.0534. found 381.0536.

A solution of 2(R)-(3-chloro-4-methanesulfonyl-phenyl)-3-(4-oxo-cyclohexyl)-propionic acid (200 mg, 0.56 mmol) and triphenylphosphine (195 mg, 0.73 mmol) in methylene chloride (4.0 mL) cooled to 0° C. was treated with N-bromosuccinimide (128 mg, 0.73 mmol) in small portions. After the complete addition of N-bromosuccinimide, the reaction mixture was allowed to warm to 25° C. over 30 min. The bright orange reaction mixture was then treated with 2-amino-5-bromopyrazine (200 mg, 1.12 mmol, prepared according to *Tetrahedron* 1988, 44, 2977-2983) and 2,6-lutidine (0.28 mL, 2.24 mmol). The resulting reaction mixture was stirred at 25° C. for 4 h. The reaction mixture was then diluted with methylene chloride (25 mL) and was successively washed with a 10% aqueous hydrochloric acid solution 1×20 mL), a saturated aqueous sodium bicarbonate solution 1×20 mL) and water 1×20 mL), dried over sodium sulfate, filtered, and concentrated in vacuo. Biotage chromatography (FLASH 40S, Silica, 65/35 hexanes/ethyl acetate eluted to 4/6 hexanes/ethyl acetate) afforded N-(5-bromo-pyrazin-2-yl)-2(R)-(3-chloro-4-methanesulfonyl-phenyl)-3-(4-oxo-cyclohexyl)-propionamide (120 mg, 42%) as an off-white foam: $[\alpha]^{23}_{589}$=–24.6° (c=0.50, chloroform); EI-HRMS m/e calcd for $C_{20}H_{21}BrClN_3O_4S$ (M+Na)$^+$ 536.0017. found 536.0022.

EXAMPLE 61

2(R)-(3-Chloro-4-methanesulfonyl-phenyl)-N-(5-chloro-pyrazin-2-yl)-3-(4-oxo-cyclohexyl)-propionamide

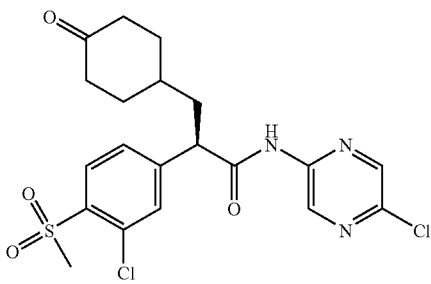

A solution of 2-aminopyrazine (23.86 g, 0.2509 mol) in methylene chloride (420 mL) was cooled to 0° C. and then treated with N-chlorosuccinimide (33.50 g, 0.2509 mol). The reaction mixture was stirred at 0° C. for 24 h. The resulting dark reaction mixture was diluted with water (500 mL) and then concentrated in vacuo to remove methylene chloride. The aqueous layer was continuously extracted with ethyl acetate until product was absence from the aqueous layer as determined by thin layer chromatography. The combined organic layers were dried over sodium sulfate, filtered, and concentrated in vacuo. Flash chromatography (Merck Silica gel 60, 70-230 mesh, 25% ethyl acetate/hexanes) afforded 2-amino-5-chloropyrazine (2.66 g, 8.2%) as a yellow solid: mp 126-128° C.; EI-HRMS m/e calcd for $C_4H_4ClN_3$ (M$^+$) 129.0094. found 129.0090.

A solution of 2(R)-(3-chloro-4-methanesulfonyl-phenyl)-3-(4-oxo-cyclohexyl)-propionic acid (prepared as in Example 60, 200 mg, 0.56 mmol) and triphenylphosphine (192 mg, 0.73 mmol) in methylene chloride (4.0 mL) cooled to 0° C. was treated with N-bromosuccinimide (128 mg, 0.73 mmol) in small portions. After the complete addition of N-bromosuccinimide, the reaction mixture was allowed to warm to 25° C. over 30 min. The bright orange reaction mixture was then treated with 2-amino-5-chloropyrazine (145 mg, 1.12 mmol) and 2,6-lutidine (0.28 mL, 2.24 mmol). The resulting reaction mixture was stirred at 25° C. for 4 h. The reaction mixture was then diluted with methylene chloride (25 mL) and was successively washed with a 10% aqueous hydrochloric acid solution 1×20 mL), a saturated aqueous sodium bicarbonate solution 1×20 mL) and water 1×20 mL), dried over sodium sulfate, filtered, and concentrated in vacuo. Biotage chromatography (FLASH 40S, Silica, 13/7 hexanes/ethyl acetate to 2/3 hexanes/ethyl acetate) afforded 2(R)-(3-chloro-4-methanesulfonyl-phenyl)-N-(5-chloro-pyrazin-2-yl)-3-(4-oxo-cyclohexyl)-propionamide (137 mg, 52%) as a light yellow foam: $[\alpha]^{23}_{589}$=–27.35° (c=0.49, chloroform); EI-HRMS m/e calcd for $C_{20}H_{21}Cl_2N_3O_4S$ (M+H)$^+$ 470.0703. found 470.0705.

EXAMPLE 62

2(R)-(3-Chloro-4-methanesulfonyl-phenyl)-N-(5-methyl-pyrazin-2-yl)-3-(4-oxo-cyclohexyl)-propionamide

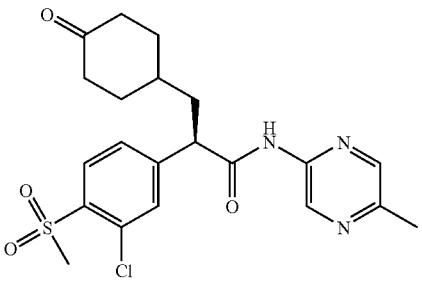

A mixture of 5-methylpyrazine-2-carboxylic acid (2.76 g, 20 mmol) and oxalyl chloride (1.83 mL, 2.66 g, 21 mmol) in methylene chloride (40 mL) was treated with N,N-dimethylformamide (0.5 mL), and the mixture was stirred at 25° C. for 1 h. The mixture was filtered, and the filtrate was concentrated in vacuo to give an oily solid. The solid was dissolved in acetone (120 mL) at 0° C. and then sodium azide (1.03 g, 20 mmol) in water (50 mL) was added dropwise. After the addition was complete, stirring was continued at 0° C. for 30 min. The mixture was then poured into ice cold water (100 mL) and extracted with methylene chloride 3×100 mL). The combined organic extracts were washed with water 1×100 mL), a mixture of a saturated aqueous sodium bicarbonate solution and a saturated aqueous sodium chloride solution (1:1, 1×100 mL), and dried over anhydrous sodium sulfate. The mixture was filtered and concentrated in vacuo to give 5-methyl-pyrazine-2-carbonyl azide (1.46 g, 45%) as a tan solid. The 5-methyl-pyrazine-2-carbonyl azide (500 mg, 3.07 mmol) was combined with benzyl alcohol (0.63 mL, 663 mg, 6.14 mmol) at 25° C. The mixture was then slowly heated on an oil bath to 90° C., upon which gas was violently evolved. The oil bath temperature was maintained until gas evolution ceased. The oil bath temperature was raised to 120° C. and stirring was continued for 10 min at that temperature. The mixture was cooled and triturated with diethyl ether/hexanes (1:4) to give (5-methylpyrazin-2-yl)-carbamic acid phenyl ester (438 mg, 58%) as a yellow solid. The (5-methylpyrazin-2-yl)-carbamic acid phenyl ester (500 mg, 2.2 mmol) and 10% palladium on carbon (212 mg) were mixed in ethanol (30 mL). The reaction vessel was flushed with hydrogen, and the mixture was stirred at 25° C. for 1 h under hydrogen (1 atm). The excess hydrogen was evacuated from the reaction vessel, and the mixture was filtered through a pad of celite. Concentration of the filtrate in vacuo gave 2-amino-5-methylpyrazine (183 mg , 76%) as a tan solid which was used without further purification.

A solution of 2(R)-(3-chloro-4-methanesulfonyl-phenyl)-3-(4-oxo-cyclohexyl)-propionic acid (prepared as in Example 60, 263 mg, 0.73 mmol) and triphenylphosphine (250 mg, 0.95 mmol) in methylene chloride (5.0 mL) cooled to 0° C. was treated with N-bromosuccinimide (167 mg, 0.95 mmol) in small portions. After the complete addition of N-bromosuccinimide, the reaction mixture was allowed to warm to 25° C. over 30 min. The bright orange reaction mixture was then treated with 2-amino-5-methylpyrazine (160 mg, 1.46 mmol) and 2,6-lutidine (0.36 mL, 2.92 mmol). The resulting reaction mixture was stirred at 25° C. for 4 h. The reaction mixture was then diluted with methylene chloride (25 mL) and was successively washed with a 10% aqueous hydrochloric acid solution 1×20 mL), a saturated aqueous sodium bicarbonate solution 1×20 mL) and water 1×20 mL), dried over sodium sulfate, filtered, and concentrated in vacuo. Biotage chromatography (FLASH 40S, Silica, 65/35 hexanes/ethyl acetate to 3/7 hexanes/ethyl acetate) afforded 2(R)-(3-chloro-4-methanesulfonyl-phenyl)-N-(5-methyl-pyrazin-2-yl)-3-(4-oxo-cyclohexyl)-propionamide (158 mg, 48%) as a white foam: $[\alpha]^{23}_{589}=-41.52°$ (c=0.33, chloroform); EI-HRMS m/e calcd for $C_{20}H_{21}Cl_2N_3O_4S$ (M+H)$^+$ 450.1249. found 450.1253.

EXAMPLE 63

2(R)-(3-Chloro-4-methanesulfonyl-phenyl)-N-(5-chloro-pyridin-2-yl)-3-(4-oxo-cyclohexyl)-propionamide

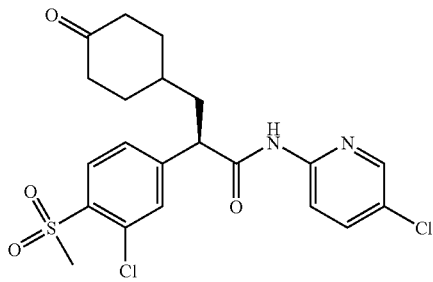

A solution of 2(R)-(3-chloro-4-methanesulfonyl-phenyl)-3-(4-oxo-cyclohexyl)-propionic acid (prepared as in Example 60, 300 mg, 0.84 mmol) and triphenylphosphine (288 mg, 1.09 mmol) in methylene chloride (6.0 mL) cooled to 0° C. was treated with N-bromosuccinimide (192 mg, 1.09 mmol) in small portions. After the complete addition of N-bromosuccinimide, the reaction mixture was allowed to warm to 25° C. over 30 min. The bright orange reaction mixture was then treated with 2-amino-5-chloropyridine (220 mg, 1.68 mmol) and 2,6-lutidine (0.42 mL, 3.36 mmol). The resulting reaction mixture was stirred at 25° C. for 4 h. The reaction mixture was then diluted with methylene chloride (25 mL) and was successively washed with a 10% aqueous hydrochloric acid solution 1×20 mL), a saturated aqueous sodium bicarbonate solution 1×20 mL) and water 1×20 mL), dried over sodium sulfate, filtered, and concentrated in vacuo. Biotage chromatography (FLASH 40S, Silica, 65/35 hexanes/ethyl acetate to 1/1 hexanes/ethyl acetate) afforded 2(R)-(3-chloro-4-methanesulfonyl-phenyl)-N-(5-chloro-pyridin-2-yl)-3-(4-oxo-cyclohexyl)-propionamide (265mg, 67%) as a white foam: $[\alpha]^{23}_{589}=-35.71°$ (c=0.35, chloroform); EI-HRMS m/e calcd for $C_{21}H_{22}Cl_2N_2O_4S$ (M+H)$^+$ 469.0750. found 469.0754.

EXAMPLE 64

2(R)-(3-Chloro-4-methanesulfonyl-phenyl)-N-(5-methyl-pyridin-2-yl)-3-(4-oxo-cyclohexyl)-propionamide

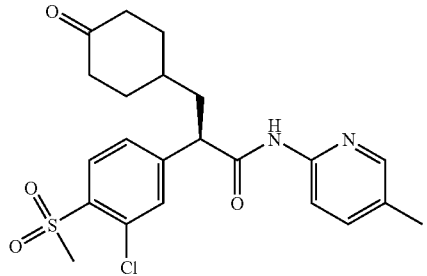

A solution of 2(R)-(3-chloro-4-methanesulfonyl-phenyl)-3-(4-oxo-cyclohexyl)-propionic acid (prepared as in Example 60, 300 mg, 0.84 mmol) and triphenylphosphine (288 mg, 1.09 mmol) in methylene chloride (6.0 mL) cooled to 0° C. was treated with N-bromosuccinimide (192 mg, 1.09 mmol) in small portions. After the complete addition of N-bromosuccinimide, the reaction mixture was allowed to warm to 25° C. over 30 min. The bright orange reaction mixture was then treated with 2-amino-5-picoline (182 mg, 1.68 mmol) and 2,6-lutidine (0.42 mL, 3.36 mmol). The resulting reaction mixture was stirred at 25° C. for 4 h. The reaction mixture was then diluted with methylene chloride (25 mL) and was successively washed with a 10% aqueous hydrochloric acid solution 1×20 mL), a saturated aqueous sodium bicarbonate solution 1×20 mL) and water 1×20 mL), dried over sodium sulfate, filtered, and concentrated in vacuo. Biotage chromatography (FLASH 40S, Silica, 65/35 hexanes/ethyl acetate to 4/6 hexanes/ethyl acetate) afforded 2(R)-(3-chloro-4-methanesulfonyl-phenyl)-N-(5-methyl-pyridin-2-yl)-3-(4-oxo-cyclohexyl)-propionamide (231 mg, 61%) as a white foam: $[\alpha]^{23}_{589}=-26.22°$ (c=0.45, chloroform); EI-HRMS m/e calcd for $C_{22}H_{25}ClN_2O_4S$ (M+H)$^+$ 449.1297. found 449.1302.

EXAMPLE 65

2-(3-Chloro-4-methanesulfonyl-phenyl)-3-(4-hydroxyimino-cyclohexyl)-N-pyrazin-2-yl-propionamide

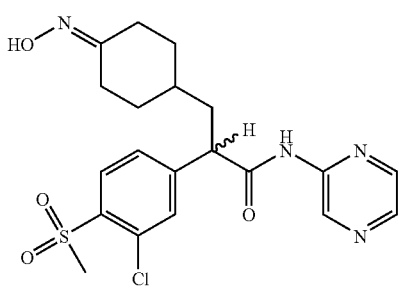

A solution of hydroxylamine hydrochloride (19 mg, 0.27 mmol) in methanol (0.5 mL) and pyridine (0.5 mL) was treated with 2-(3-chloro-4-methanesulfonyl-phenyl)-3-(4-oxo-cyclohexyl)-N-pyrazin-2-yl-propionamide (prepared as in Example 58, 80 mg, 0.18 mmol). The reaction mixture was heated under reflux for 2 h, cooled to 25° C., and concentrated in vacuo to remove methanol. The resulting residue was suspended in ethyl acetate (10 mL), washed with water 1×5 mL), dried over magnesium sulfate, filtered, and concentrated in vacuo. Biotage chromatography (FLASH 12M, Silica, 35/65 hexanes/ethyl acetate to 1/1 hexanes/ethyl acetate) afforded 2-(3-chloro-4-methanesulfonyl-phenyl)-3-(4-hydroxyimino-cyclohexyl)-N-pyrazin-2-yl-propionamide (65 mg, 80%) was a white foam: EI-HRMS m/e calcd for $C_{20}H_{23}ClN_4O_4S$ (M+H)$^+$ 451.1202. found 451.1206.

EXAMPLE 66

N-(5-Bromo-pyrazin-2-yl)-2-(3-chloro-4-methanesulfonyl-phenyl)-3-(4-hydroxyimino-cyclohexyl)-propionamide

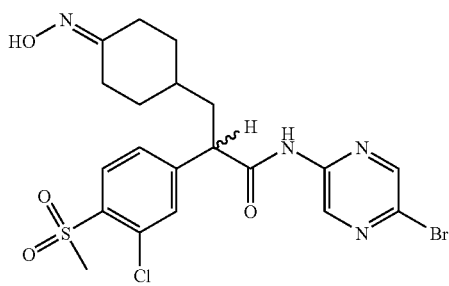

A solution of hydroxylamine hydrochloride (13 mg, 0.18 mmol) in methanol (0.5 mL) and pyridine (0.5 mL) was treated with N-(5-bromo-pyrazin-2-yl)-2-(3-chloro-4-methanesulfonyl-phenyl)-3-(4-oxo-cyclohexyl)-propionamide (prepared as in Example 59, 62 mg, 0.12 mmol). The reaction mixture was heated under reflux for 2 h, cooled to 25° C., and concentrated in vacuo to remove methanol. The resulting residue was suspended in ethyl acetate (10 mL), washed with water 1×5 mL), dried over magnesium sulfate, filtered, and concentrated in vacuo. Biotage chromatography (FLASH 12M, Silica, 3/7 hexanes/ethyl acetate eluted to 8/2 hexanes/ethyl acetate) afforded the N-(5-bromo-pyrazin-2-yl)-2-(3-chloro-4-methanesulfonyl-phenyl)-3-(4-hydroxyimino-cyclohexyl)-propionamide (51 mg, 80%) as a white foam: EI-HRMS m/e calcd for $C_{20}H_{22}BrClN_4O_4S$ (M+H)$^+$ 529.0307. found 529.0308.

EXAMPLE 67

N-(5-Bromo-pyrazin-2-yl)-2(R)-(3-chloro-4-methanesulfonyl-phenyl)-3-(4-hydroxyimino-cyclohexyl)-propionamide

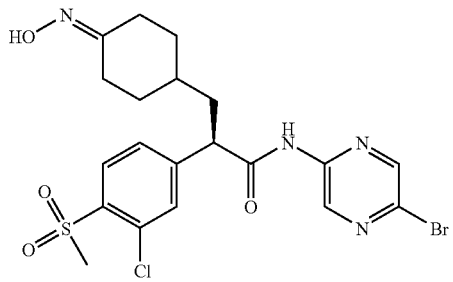

A solution of hydroxylamine hydrochloride (7.0 mg, 0.099 mmol) in methanol (0.2 mL) and 2,6-lutidine (0.2 mL) was treated with N-(5-bromo-pyrazin-2-yl)-2(R)-(3-chloro-4-methanesulfonyl-phenyl)-3-(4-oxo-cyclohexyl)-propionamide (prepared as in Example 60, 34 mg, 0.066 mmol). The reaction mixture was stirred at 25° C. for 30 min and was then concentrated in vacuo to remove methanol. The resulting residue was suspended in ethyl acetate (10 mL), washed with water 1×5 mL), dried over magnesium sulfate, filtered, and concentrated in vacuo. Biotage chromatography (FLASH 12M, Silica, 65/35 hexanes/ethyl acetate to 2/3 hexanes/ethyl acetate) afforded the N-(5-bromo-pyrazin-2-yl)-2(R)-(3-chloro-4-methanesulfonyl-phenyl)-3-(4-hydroxyimino-cyclohexyl)-propionamide (30 mg, 85.8%) was a white foam: $[\alpha]^{23}_{589}$=−21.43° (c=0.35, chloroform); EI-HRMS m/e calcd for $C_{20}H_{22}BrClN_4O_4S$ (M+H)$^+$ 529.0307. found 529.0314.

EXAMPLE 68

2(R)-(3-Chloro-4-methanesulfonyl-phenyl)-N-(5-chloro-pyrazin-2-yl)-3-(4-hydroxyimino-cyclohexyl)-propionamide

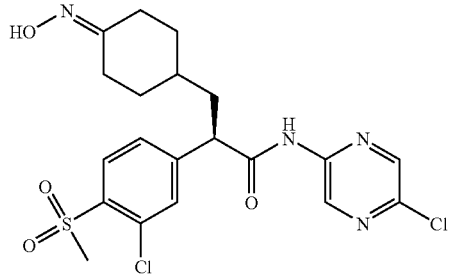

A solution of hydroxylamine hydrochloride (7.0 mg, 0.099 mmol) in methanol (0.2 mL) and 2,6-lutidine (0.2 mL)

was treated with 2(R)-(3-chloro-4-methanesulfonyl-phenyl)-N-(5-chloro-pyrazin-2-yl)-3-(4-oxo-cyclohexyl)-propionamide (prepared as in Example 61, 31 mg, 0.066 mmol). The reaction mixture was stirred at 25° C. for 30 min and was then concentrated in vacuo to remove methanol. The resulting residue was suspended in ethyl acetate (10 mL), washed with water 1×5 mL), dried over magnesium sulfate, filtered, and concentrated in vacuo. Biotage chromatography (FLASH 12S, Silica, 13/7 hexanes/ethyl acetate to 2/3 hexanes/ethyl acetate) afforded 2(R)-(3-chloro-4-methanesulfonyl-phenyl)-N-(5-chloro-pyrazin-2-yl)-3-(4-hydroxyimino-cyclohexyl)-propionamide (30 mg, 93.7%) was a white foam: $[\alpha]^{23}_{589}=-23.24°$ (c=0.37, chloroform); EI-HRMS m/e calcd for $C_{20}H_{22}Cl_2N_4O_4S$ (M+H)$^+$ 485.0812. found 485.0822.

EXAMPLE 69

2(R)-(3-Chloro-4-methanesulfonyl-phenyl)-3-(4-hydroxyimino-cyclohexyl)-N-(5-methyl-pyrazin-2-yl)-propionamide

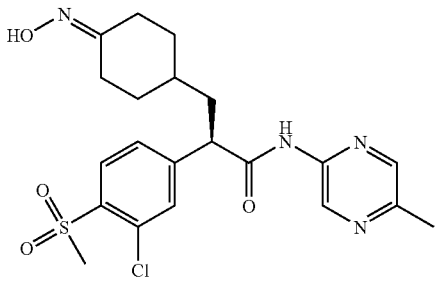

A solution of hydroxylamine hydrochloride (17.0 mg, 0.24 mmol) in methanol (0.5 mL) and 2,6-lutidine (0.5 mL) was treated with 2(R)-(3-chloro-4-methanesulfonyl-phenyl)-N-(5-methyl-pyrazin-2-yl)-3-(4-oxo-cyclohexyl)-propionamide (prepared as in Example 62, 34 mg, 0.066 mmol). The reaction mixture was stirred at 25° C. for 30 min and was then concentrated in vacuo to remove methanol. The resulting residue was suspended in ethyl acetate (10 mL), washed with water 1×5 mL), dried over magnesium sulfate, filtered, and concentrated in vacuo. Biotage chromatography (FLASH 12M, Silica, 65/35 hexanes/ethyl acetate to ethyl acetate) afforded 2(R)-(3-chloro-4-methanesulfonyl-phenyl)-3-(4-hydroxyimino-cyclohexyl)-N-(5-methyl-pyrazin-2-yl)-propionamide (75 mg, 100%) was a white foam: $[\alpha]^{23}_{589}=-30.0°$ (c=0.32 chloroform); EI-HRMS m/e calcd for $C_{21}H_{25}ClN_4O_4S$ (M+H)$^+$ 465.1358. found 465.1365.

EXAMPLE 70

2(R)-(3-Chloro-4-methanesulfonyl-phenyl)-N-(5-chloro-pyridin-2-yl)-3-(4-hydroxyimino-cyclohexyl)-propionamide

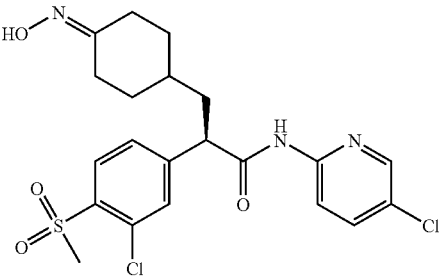

A solution of hydroxylamine hydrochloride (26.0 mg, 0.36 mmol) in methanol (0.7 mL) and 2,6-lutidine (0.7 mL) was treated with 2(R)-(3-chloro-4-methanesulfonyl-phenyl)-N-(5-chloro-pyridin-2-yl)-3-(4-oxo-cyclohexyl)-propionamide (prepared as in Example 63, 114 mg, 0.24 mmol). The reaction mixture was stirred at 25° C. for 30 min and was then concentrated in vacuo to remove methanol. The resulting residue was suspended in ethyl acetate (10 mL), washed with water 1×5 mL), dried over magnesium sulfate, and concentrated in vacuo. Biotage chromatography (FLASH 40S, Silica, 65/35 hexanes/ethyl acetate to 2/8 hexanes/ethyl acetate) afforded 2(R)-(3-chloro-4-methanesulfonyl-phenyl)-N-(5-chloro-pyridin-2-yl)-3-(4-hydroxyimino-cyclohexyl)-propionamide (105 mg, 90%) was a white powder: $[\alpha]^{23}_{589}=-23.03°$ (c=0.33 chloroform); EI-HRMS m/e calcd for $C_{21}H_{23}Cl_2N_3O_4S$ (M+H)$^+$ 484.0859. found 484.0862.

EXAMPLE 71

2(R)-(3-Chloro-4-methanesulfonyl-phenyl)-3-(4-hydroxyimino-cyclohexyl)-N-(5-methyl-pyridin-2-yl)-propionamide

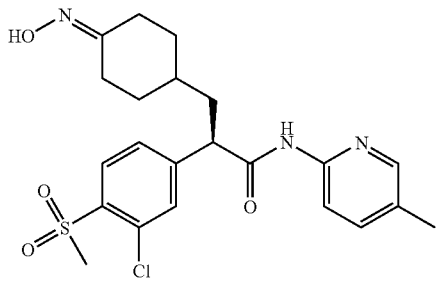

Solution of hydroxylamine hydrochloride (26.0 mg, 0.36 mmol) in methanol (0.7 mL) and 2,6-lutidine (0.7 mL) was treated with 2(R)-(3-chloro-4-methanesulfonyl-phenyl)-N-(5-methyl-pyridin-2-yl)-3-(4-oxo-cyclohexyl)-propionamide (prepared as in Example 64, 105 mg, 0.23 mmol). The reaction mixture was stirred at 25° C. for 30 min and was then concentrated in vacuo to remove methanol. The resulting residue was suspended in ethyl acetate (10 mL), washed with water 1×5 mL), dried over magnesium sulfate, and concentrated in vacuo. Biotage chromatography (FLASH 40S, Silica, 65/35 hexanes/ethyl acetate to 2/8 hexanes/ethyl acetate) afforded 2(R)-(3-chloro-4-methanesulfonyl-phenyl)-3-(4-hydroxyimino-cyclohexyl)-N-(5-methyl-pyridin-2-yl)-propionamide (67 mg, 63%) was a white foam; $[\alpha]^{23}_{589}=-7.84°$ (c=0.37 chloroform); EI-HRMS m/e calcd for $C_{22}H_{26}ClN_3O_4S$ (M+H)$^+$ 464.1406. found 464.1409.

EXAMPLE 72

2-(3-Chloro-4-methanesulfonyl-phenyl)-3-(4-methoxyimino-cyclohexyl)-N-pyrazin-2-yl-propionamide

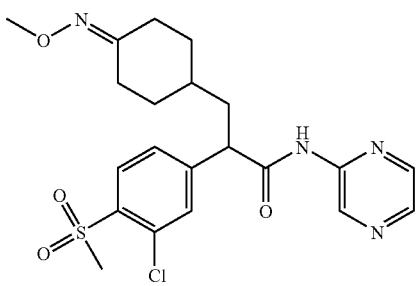

A solution of methoxylamine hydrochloride (23 mg, 0.27 mmol) in methanol (0.5 mL) and pyridine (0.5 mL) was treated with 2-(3-chloro-4-methanesulfonyl-phenyl)-3-(4-oxo-cyclohexyl)-N-pyrazin-2-yl-propionamide (prepared as in Example 58, 80 mg, 0.18 mmol). The reaction mixture was heated under reflux for 2 h, cooled to 25° C., and concentrated in vacuo to remove methanol. The resulting residue was suspended in ethyl acetate (10 mL), washed with water 1×5 mL), dried over magnesium sulfate, filtered, and concentrated in vacuo. Biotage chromatography (FLASH 12M, Silica, 35/65 hexanes/ethyl acetate) afforded 2-(3-chloro-4-methanesulfonyl-phenyl)-3-(4-methoxyimino-cyclohexyl)-N-pyrazin-2-yl-propionamide (68 mg, 81%) was a white foam: EI-HRMS m/e calcd for $C_{21}H_{25}ClN_4O_4S$ (M+H)$^+$ 465.1358. found 465.1364.

EXAMPLE 73

N-(5-Bromo-pyrazin-2-yl)-2-(3-chloro-4-methanesulfonyl-phenyl)-3-(4-methoxyimino-cyclohexyl)-propionamide

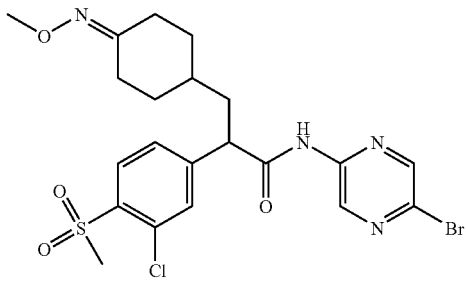

A solution of methoxylamine hydrochloride (16 mg, 0.18 mmol) in methanol (0.5 mL) and pyridine (0.5 mL) was treated with N-(5-bromo-pyrazin-2-yl)-2-(3-chloro-4-methanesulfonyl-phenyl)-3-(4-oxo-cyclohexyl)-propionamide (prepared as in Example 59, 62 mg, 0.12 mmol). The reaction mixture was heated under reflux for 2 h, cooled to 25° C., and concentrated in vacuo to remove methanol. The resulting residue was suspended in ethyl acetate (10 mL), washed with water 1×5 mL), dried over magnesium sulfate, filtered, and concentrated in vacuo. Biotage chromatography (FLASH 12M, Silica, 7/3 hexanes/ethyl acetate eluted to 4/6 hexanes/ethyl acetate) afforded the N-(5-bromo-pyrazin-2-yl)-2-(3-chloro-4-methanesulfonyl-phenyl)-3-(4-methoxyimino-cyclohexyl)-propionamide (51 mg, 80%) as a white foam: EI-HRMS m/e calcd for $C_{21}H_{24}BrClN_4O_4S$ (M+H)$^+$ 543.0463. found 543.0464.

BIOLOGICAL ACTIVITY EXAMPLES

Example A

In Vitro Glucokinase Activity

Glucokinase Assay: Glucokinase (GK) was assayed by coupling the production of glucose-6-phosphate to the generation of NADH with glucose-6-phosphate dehydrogenase (G6PDH, 0.75-1 k units/mg; Boehringer Mannheim, Indianapolis, Id.) from *Leuconostoc mesenteroides* as the coupling enzyme (Scheme 2). Recombinant Scheme 2

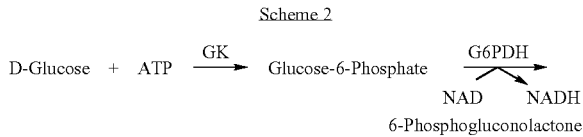

Human liver GK1 was expressed in *E. coli* as a glutathione S-transferase fusion protein (GST-GK) [Liang et al, 1995] and was purified by chromatography over a glutathione-Sepharose 4B affinity column using the procedure provided by the manufacturer (Amersham Pharmacia Biotech, Piscataway, N.J.). Previous studies have demonstrated that the enzymatic properties of native GK and GST-GK are essentially identical (Liang et al, 1995; Neet et al., 1990).

The assay was conducted at 25° C. in a flat bottom 96-well tissue culture plate from Costar (Cambridge, Mass.) with a final incubation volume of 120 µL. The incubation mixture contained: 25 mM Hepes buffer (pH, 7.1), 25 mM KCl, 5 mM D-glucose, 1 mM ATP, 1.8 mM NAD, 2 mM $MgCl_2$, 1 µM sorbitol-6-phosphate, 1 mM dithiothreitol, test drug or 10% DMSO, 1.8 unit/ml G6PDH, and GK (see below). All organic reagents were >98% pure and were from Boehringer Mannheim with the exceptions of D-glucose and Hepes that were from Sigma Chemical Co, St Louis, Mo. Test compounds were dissolved in DMSO and were added to the incubation mixture minus GST-GK in a volume of 12 µl to yield a final DMSO concentration of 10%. This mix was pre-incubated in the temperature controlled chamber of a SPECTRAmax 250 microplate spectrophotometer (Molecular Devices Corporation, Sunnyvale, Calif.) for 10 minutes to allow temperature equilibrium and then the reaction was started by the addition of 20 µl GST-GK.

After addition of enzyme, the increase in optical density (OD) at 340 mn was monitored over a 10 minute incubation period as a measure of GK activity. Sufficient GST-GK was added to produce an increase in $OD_{340}$ of 0.08 to 0.1 units over the 10 minute incubation period in wells containing 10% DMSO, but no test compound. Preliminary experiments established that the GK reaction was linear over this period of time even in the presence of activators that produced a 5-fold increase in GK activity. The GK activity in control wells was compared with the activity in wells containing test GK activators, and the concentration of activator that produced a 50% increase in the activity of GK, i.e., the $SC_{1.5}$, was calculated. All of the compounds of formula I described in the Synthesis Examples had an $SC_{1.5}$ less than or equal to 30 µM.

REFERENCES

Liang, Y., Kesavan, P., Wang, L., Niswender, K., Tanizawa, Y., Permut, M. A., Magnuson, M., and Matschinsky, F. M. Variable effects of maturity-onset-diabetes-of-youth (MODY)-associated glucokinase mutations on the substrate interactions and stability of the enzyme. *Biochem. J* 309:167-173, 1995.

Neet, K., Keenan, R. P., and Tippett, P. S. Observation of a kinetic slow transition in monomeric glucokinase. *Biochemistry* 29;770-777, 1990.

Example B

In Vivo Activity

Glucokinase Activator In Vivo Screen Protocol

C57BL/6J mice are orally dosed via gavage with Glucokinase (GK) activator at 50 mg/kg body weight following a two hour fasting period. Blood glucose determinations are made five times during the six hour post-dose study period.

Mice (n=6) are weighed and fasted for a two hour period prior to oral treatment. GK activators are formulated at 6.76 mg/ml in Gelucire vehicle (Ethanol:Gelucire44/14:PEG400q.s. 4:66:30 v/w/v. Mice are dosed orally with 7.5 µl formulation per gram of body weight to equal a 50 mg/kg dose. Immediately prior to dosing, a pre dose (time zero) blood glucose reading is acquired by snipping off a small portion of the animals tail (~1 mm) and collecting 15 µt blood into a heparinized capillary tube for analysis. Following GK activator administration, additional blood glucose readings are taken at 1, 2, 4 and 6 hours post dose from the same tail wound. Results are interpreted by comparing the mean blood glucose values of six vehicle treated mice with six GK activator treated mice over the six hour study duration. Compounds are considered active when they, exhibit a statistically significant ($p \leq 0.05$) decrease in blood glucose compared to vehicle for two consecutive assay time points.

What is claimed is:

1. A compound according to formula I:

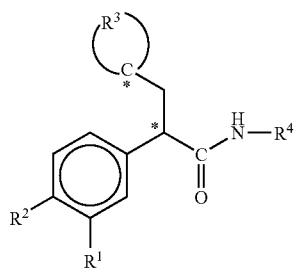

I wherein $R^1$ and $R^2$ are independently hydrogen, halo, amino, hydroxyamino, cyano, nitro, lower alkyl, —$OR^5$,

perfluoro-lower alkyl, lower alkyl thio, perfluoro-lower alkyl thio, lower alkyl sulfonyl, perfluoro-lower alkyl sulfonyl, lower alkyl sulfinyl, or sulfonamido;

$R^3$ is an unbranched heteroalkyl chain of 3-4 carbon atoms plus one oxygen or sulfur atom, wherein the chain, in combination with the carbon atom it is bonded to, forms a five- or six-membered ring, and when the chain contains an O heteroatom, the chain is unsubstituted, and when the chain contains an S heteroatom, the chain is unsubstituted or the S heteroatom member of the chain is substituted by an oxo group;

$R^4$ is

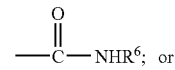

an unsubstituted or mono-substituted five- or six-membered heteroaromatic ring connected by a ring carbon atom to the amine group shown, which five- or six-membered heteroaromatic ring contains from 1 to 3 heteroatoms selected from sulfur, oxygen or nitrogen, with one heteroatom being nitrogen which is adjacent to the connecting ring carbon atom; said mono-substituted heteroaromatic ring being mono-substituted at a position on a ring carbon atom other than adjacent to said connecting carbon atom with a substituent selected from the group consisting of lower alkyl, halo, nitro, cyano, perfluoro-lower alkyl, amidooxime,

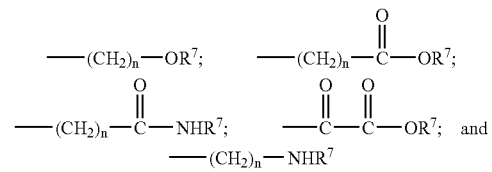

n is 0, 1, 2, 3 or 4;

$R^5$ is hydrogen, lower alkyl, or perfluoro-lower alkyl;

$R^6$ is lower alkyl; and $R^7$ is hydrogen or lower alkyl;

\* denotes a carbon atom that is asymmetric in all or most of the compounds of formula I;

or a pharmaceutically acceptable salt thereof.

2. A compound according to formula I:

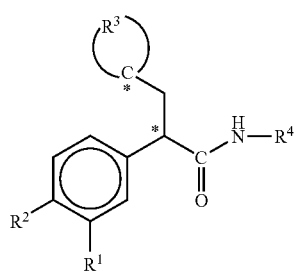

I wherein $R^1$ is hydrogen, halo, or perfluoro-lower alkyl;

$R^2$ is halo or lower alkyl sulfonyl;

$R^3$ is an unbranched heteroalkyl chain of 3-4 carbon atoms plus one oxygen or sulfur atom, wherein the chain, in combination with the carbon atom it is bonded to, forms a five- or six-membered ring, and when the chain contains an O heteroatom, the chain is unsubstituted, and when the chain contains an S heteroatom, the chain is unsubstituted or the S heteroatom member of the chain is substituted by an oxo group;

R⁴ is

an unsubstituted or mono-substituted five- or six-membered heteroaromatic ring connected by a ring carbon atom to the amine group shown, which five- or six-membered heteroaromatic ring contains from 1 or 2 heteroatoms selected from sulfur or nitrogen, with one heteroatom being nitrogen which is adjacent to the connecting ring carbon atom; said mono-substituted heteroaromatic ring being mono-substituted at a position on a ring carbon atom other than adjacent to said connecting carbon atom with a substituent selected from the group consisting of lower alkyl, lower alkoxy, halo, nitro, cyano, perfluoro-lower alkyl, amidooxime,

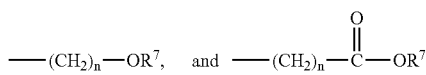

n is 0, 1, 2, 3 or 4;
R⁶ is lower alkyl and R⁷ is hydrogen or lower alkyl;
* denotes a carbon atom that is asymmetric in all or most of the compounds of formula I;
or a pharmaceutically acceptable salt thereof.

3. The compound according to claim 2, wherein

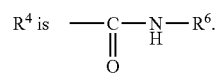

4. The compound according to claim 3, wherein R³ is a chain of 3 carbon atoms and one oxygen atom.

5. The compound according to claim 4, which is 1-[2-(3,4-Dichloro-phenyl)-3-(tetrahydro-furan-2-yl)-propionyl]-3-methyl-urea.

6. The compound according to claim 3, wherein R³ is a chain of 3 carbon atoms and one sulfur atom, wherein the chain is unsubstituted or substituted with an oxo group at the sulfur atom.

7. The compound according to claim 3, wherein R³ is a chain of 4 carbon atoms and one oxygen atom.

8. The compound according to claim 7, which is 1-[2-(3,4-Dichloro-phenyl)-3-(tetrahydro-pyran-2-yl)-propionyl]-3-methyl urea.

9. The compound according to claim 7, which is 1-[2-(4-Methanesulfonyl-phenyl)-3-(tetrahydro-pyran-2-yl)-propionyl]-3-methyl-urea.

10. The compound according to claim 3, wherein R³ is a chain of 4 carbon atoms and one sulfur atom, wherein the chain is unsubstituted or substituted with an oxo group at the sulfur atom.

11. The compound according to claim 2, wherein R⁴ is an unsubstituted or mono-substituted five- or six-membered heteroaromatic ring connected by a ring carbon atom to the amine group shown, which five- or six-membered heteroaromatic ring contains from 1 or 2 heteroatoms selected from sulfur or nitrogen, with one heteroatom being nitrogen which is adjacent to the connecting ring carbon atom; said mono-substituted heteroaromatic ring being mono-substituted at a position on a ring carbon atom other than adjacent to said connecting carbon atom with a substituent selected from the group consisting of lower alkyl, lower alkoxy, halo, nitro, cyano, perfluoro-lower alkyl, amidooxime, or

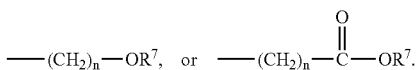

12. The compound according to claim 2, wherein R⁴ is a five-membered ring.

13. The compound according to claim 12, wherein R⁴ is an unsubstituted five-membered ring containing two heteroatoms, one each of sulfur and nitrogen.

14. The compound according to claim 13, wherein R³ is a chain of 3 carbon atoms and one oxygen atom.

15. The compound according to claim 14, which is 2-(3,4-Dichloro-phenyl)-3-(tetrahydro-furan-2-yl)-N-thiazol-2-yl-propionamide.

16. The compound according to claim 14, which is 2-(4-Methanesulfonyl-phenyl)-3-(tetrahydro-furan-2(R)-yl)-N-thiazol-2-yl-propionamide.

17. The compound according to claim 13, wherein R³ is a chain of 3 carbon atoms and one sulfur atom, wherein the chain is unsubstituted or substituted with an oxo group at the sulfur atom.

18. The compound according to claim 13, wherein R³ is a chain of 4 carbon atoms and one oxygen atom.

19. The compound according to claim 18, which is 2-(3,4-Dichloro-phenyl)-3-(tetrahydro-pyran-2-yl)-N-thiazol-2-yl-propionamide.

20. The compound according to claim 18, which is 2(R)-(3,4-Dichloro-phenyl)-3-(tetrahydro-pyran-2-yl)-N-thiazol-2-yl-propionamide.

21. The compound according to claim 18, which is 2-(4-Methanesulfonyl-phenyl)-3-(tetrahydro-pyran-2-yl)-N-thiazol-2-yl-propionamide.

22. The compound according to claim 18, which is 2-(4-Methylsulfonyl-3-trifluoromethyl-phenyl)-3-(tetrahydro-pyran-2-yl)-N-thiazole-2-yl-propionamide.

23. The compound according to claim 13, wherein R³ is a chain of 4 carbon atoms and one sulfur atom, wherein the chain is unsubstituted or substituted with an oxo group at the sulfur atom.

24. The compound according to claim 12, wherein R⁴ is a substituted five-membered ring containing two heteroatoms, one each of sulfur and nitrogen.

25. The compound according to claim 18, wherein R⁴ is a six-membered ring.

26. The compound according to claim 25, wherein R⁴ is a six-membered ring containing one heteroatom, which is nitrogen.

27. The compound according to claim 26, wherein R³ is a chain of 3 carbon atoms and one oxygen atom.

28. The compound according to claim 25, wherein R³ is a chain of 3 carbon atoms and one sulfur atom, wherein the chain is unsubstituted or substituted with an oxo group at the sulfur atom.

29. The compound according to claim 26, wherein R³ is a chain of 4 carbon atoms and one oxygen atom.

30. The compound according to claim 29, which is 6-[2-(4-Methylsulfonyl-3-trifluoromethyl-phenyl)-3-(tetrahydro-pyran-2-yl)-propionylamino]-nicotinic acid methyl ester.

31. The compound according to claim 29, which is 6-[2-(4-Methylsulfonyl-3-trifluoromethyl-phenyl)-3-(tetrahydro-pyran-2-yl)-propionylamino]-nicotinic acid.

32. The compound according to claim 29, which is N-(5-Hydroxymethyl-pyridin-2-yl)-2-(4-methylsulfonyl-3-trifluoromethyl-phenyl)-3-(tetrahydro-pyran-2-yl)-propionamide.

33. The compound according to claim 26, wherein $R^3$ is a chain of 4 carbon atoms and one sulfur atom, wherein the chain is unsubstituted or substituted with an oxo group at the sulfur atom.

34. The compound according to claim 25, wherein $R^4$ is a six-membered ring containing two heteroatoms, each of which is nitrogen.

35. The compound according to claim 34, wherein $R^3$ is a chain of 3 carbon atoms and one oxygen atom.

36. The compound according to claim 35, which is 2-(3-Chloro-4-methanesulfonyl-phenyl)-N-pyrazin-2-yl-3-(tetrahydro-furan-2(R)-yl)-propionamide.

37. The compound according to claim 35, which is 2-(4-Methanesulfonyl-3-trifluoromethyl-phenyl)-N-pyrazin-2-yl-3-(tetrahydro-furan-2(R)-yl)-propionamide.

38. The compound according to claim 35, which is 2-(3-Chloro-4-methanesulfonyl-phenyl)-N-pyrazin-2-yl-3-(tetrahydro-furan-3-yl)-propionamide.

39. The compound according to claim 34, wherein $R^3$ is a chain of 3 carbon atoms and one sulfur atom, wherein the chain is unsubstituted or substituted with an oxo group at the sulfur atom.

40. The compound according to claim 34, wherein $R^3$ is a chain of 4 carbon atoms and one oxygen atom.

41. The compound according to claim 40, which is 2-(4-Methanesulfonyl-3-trifluoromethyl-phenyl)-N-pyrazin-2-yl-3-(tetrahydro-pyran-2-yl)-propionamide.

42. The compound according to claim 40, which is 2-(3-Chloro-4-methanesulfonyl-phenyl)-N-pyrazin-2-yl-3-(tetrahydro-pyran-4-yl)-propionamide.

43. The compound according to claim 40, which is N-(5-Bromo-pyrazin-2-yl)-2-(3-chloro-4-methanesulfonyl-phenyl)-3-(tetrahydro-pyran-4-yl)-propionamide.

44. The compound according to claim 40, which is 2-(3-Chloro-4-methanesulfonyl-phenyl)-N-(5-cyano-pyrazin-2-yl)-3-(tetrahydro-pyran-4-yl)-propionamide.

45. The compound according to claim 40, which is 2-(3-Chloro-4-methanesulfonyl-phenyl)-N-[5-(N-hydroxycarbamimidoyl)-pyrazin-2-yl]-3-(tetrahydro-pyran-4-yl)-propionamide.

46. The compound according to claim 34, wherein $R^3$ is a chain of 4 carbon atoms and one sulfur atom, wherein the chain is unsubstituted or substituted with an oxo group at the sulfur atom.

47. The compound according to claim 46, which is 2-(3-Chloro-4-methanesulfonyl-phenyl)-N-pyrazin-2-yl-3-(tetrahydro-thiopyran-3 (R)-yl)-propionamide.

48. The compound according to claim 46, which is 2-(3-Chloro-4-methanesulfonyl-phenyl)-3-(1-oxo-hexahydro-1$\lambda^4$-thiopyran-3 (R)-yl)-N-pyrazin-2-yl-propionamide.

* * * * *